United States Patent
Lombardi et al.

(10) Patent No.: US 8,921,243 B2
(45) Date of Patent: Dec. 30, 2014

(54) FABRICS COMPRISING A PHOTOCATALYST TO PRODUCE SINGLET OXYGEN FROM AMBIENT OXYGEN

(76) Inventors: John L. Lombardi, Tucson, AZ (US);
Changton Chuchawin, Tucson, AZ (US)

(*) Notice: Subject to any disclaimer, the term of this patent is extended or adjusted under 35 U.S.C. 154(b) by 0 days.

(21) Appl. No.: 13/263,732

(22) PCT Filed: Apr. 7, 2010

(86) PCT No.: PCT/US2010/030304
§ 371 (c)(1),
(2), (4) Date: Jan. 23, 2012

(87) PCT Pub. No.: WO2010/118180
PCT Pub. Date: Oct. 14, 2010

(65) Prior Publication Data
US 2012/0135651 A1    May 31, 2012

Related U.S. Application Data

(63) Continuation-in-part of application No. 12/652,670, filed on Jan. 5, 2010, now Pat. No. 8,481,446.

(60) Provisional application No. 61/167,409, filed on Apr. 7, 2009.

(51) Int. Cl.
| B32B 3/00 | (2006.01) |
| B01J 31/02 | (2006.01) |
| B01J 31/18 | (2006.01) |
| C07F 7/18 | (2006.01) |
| A62D 5/00 | (2006.01) |
| B01J 31/38 | (2006.01) |
| B01J 37/02 | (2006.01) |
| B01J 35/00 | (2006.01) |
| B01D 53/88 | (2006.01) |

(52) U.S. Cl.
CPC ............... A62D 5/00 (2013.01); B01J 31/183 (2013.01); C07F 7/1836 (2013.01); *B01D 2259/802* (2013.01); *B01D 2257/91* (2013.01); B01J 31/38 (2013.01); B01J 37/0219 (2013.01); *B01J 2531/025* (2013.01); B01J 35/004 (2013.01); B01D 53/885 (2013.01); B01J 31/1815 (2013.01); *B01J 2531/31* (2013.01)
USPC ............................................. 442/59; 502/158

(58) Field of Classification Search
CPC .. A62D 5/00; B01J 2531/025; B01J 2531/31; B01J 31/1815; B01J 31/38; B01J 31/183; B01J 31/02; B01J 31/1658; B01J 31/06; D06M 13/513; D06M 2400/01
USPC ............................................. 442/59; 501/158
See application file for complete search history.

(56) References Cited

U.S. PATENT DOCUMENTS

| 4,436,715 A * | 3/1984 | Schaap et al. ................. 423/579 |
| 6,107,480 A | 8/2000 | Funken et al. |

(Continued)

FOREIGN PATENT DOCUMENTS

WO    2007114843    10/2007

OTHER PUBLICATIONS

PCT/US2010/021930—International Search Report and Written Opinion dated Apr. 20, 2010.

(Continued)

*Primary Examiner* — Peter Y Choi
*Assistant Examiner* — Vincent A Tatesure
(74) *Attorney, Agent, or Firm* — Dale F. Regelman; Quarles & Brady LLP

(57) ABSTRACT

A fabric comprising one or more photocatalysts to produce singlet oxygen from ambient oxygen. In certain embodiments, the fabric further comprises a compound to reversibly react with singlet oxygen to form an endoperoxide.

17 Claims, 7 Drawing Sheets

(56) References Cited

U.S. PATENT DOCUMENTS

| | | |
|---|---|---|
| 7,259,122 B1 | 8/2007 | Lombardi |
| 2003/0027884 A1* | 2/2003 | Kim et al. ........................ 522/81 |
| 2003/0194433 A1* | 10/2003 | Hei et al. ....................... 424/465 |
| 2005/0009724 A1 | 1/2005 | Arredondo et al. |
| 2008/0171803 A1 | 7/2008 | Lombardi |

OTHER PUBLICATIONS

PCT/US2010/021930—International Preliminary Report on Patentability dated Oct. 11, 2011.

EP10762408—Supplementary European Search Report dated Jan. 28, 2013.

* cited by examiner

FABRICS COMPRISING A PHOTOCATALYST TO PRODUCE SINGLET OXYGEN FROM AMBIENT OXYGEN

CROSS-REFERENCE TO RELATED APPLICATIONS

This application represents the national stage entry of PCT International Application No. PCT/US2012/030304 filed Apr. 7, 2010, which claims priority to U.S. Provisional Patent Application No. 61/167,409 filed Apr. 7, 2009, and U.S. Continuation-In-Part Patent Application having Ser. No. 12/652,670 filed Jan. 5, 2010, now U.S. Pat. No. 8,481,446, all of which are hereby incorporated by reference herein in their entirely for all purposes.

GOVERNMENT LICENSE RIGHTS

The U.S. Government has a paid-up license in this invention and the right in limited circumstances to require the patent owner to license others on reasonable terms as provided by the terms of "Lightweight and Low Cost Flexible Structure Textiles" U.S. Army Phase I Small Business Innovation Research Grant Contract No. DAAD16-03-C-0011.

FIELD OF THE INVENTION

The invention relates to fabrics comprising a photocatalyst to produce singlet oxygen from ambient oxygen. In certain embodiments, the fabrics further comprise a compound to react reversibly with singlet oxygen.

BACKGROUND OF THE INVENTION

Many industrial, commercial, and residential facilities use air fresheners to mitigate unpleasant odors in indoor spaces. Such air fresheners may be in the form of candles, aerosol sprays, potpourri, gels, and mechanical or heat released products. However, while such products may neutralize or otherwise cover odors, they are also associated with negative health affects. Many common air fresheners contain chemicals that can aggravate asthma and contain hazardous or toxic chemicals such as phthalates, acetone, chloromethane, acetaldehyde, and 1,4-dioxane. Thus, the health consequences of exposure to air fresheners is a growing concern.

SUMMARY OF THE INVENTION

A fabric comprising a photocatalyst to produce singlet oxygen from ambient oxygen is presented. In certain embodiments, the fabric includes a coating comprising the photocatalyst, and optionally one or more compounds to reversibly react with singlet oxygen.

Indoor accessories are presented, wherein those indoor accessories comprise a fabric comprising a photocatalyst to produce singlet oxygen from ambient oxygen is presented. In certain embodiments, the fabric includes a coating comprising the photocatalyst, and optionally one or more compounds to reversibly react with singlet oxygen. The indoor accessories are selected from the group consisting of furniture, cushions, pillows, bedding, curtains, and floor coverings.

DETAILED DESCRIPTION OF THE PREFERRED EMBODIMENTS

Figure 1A:
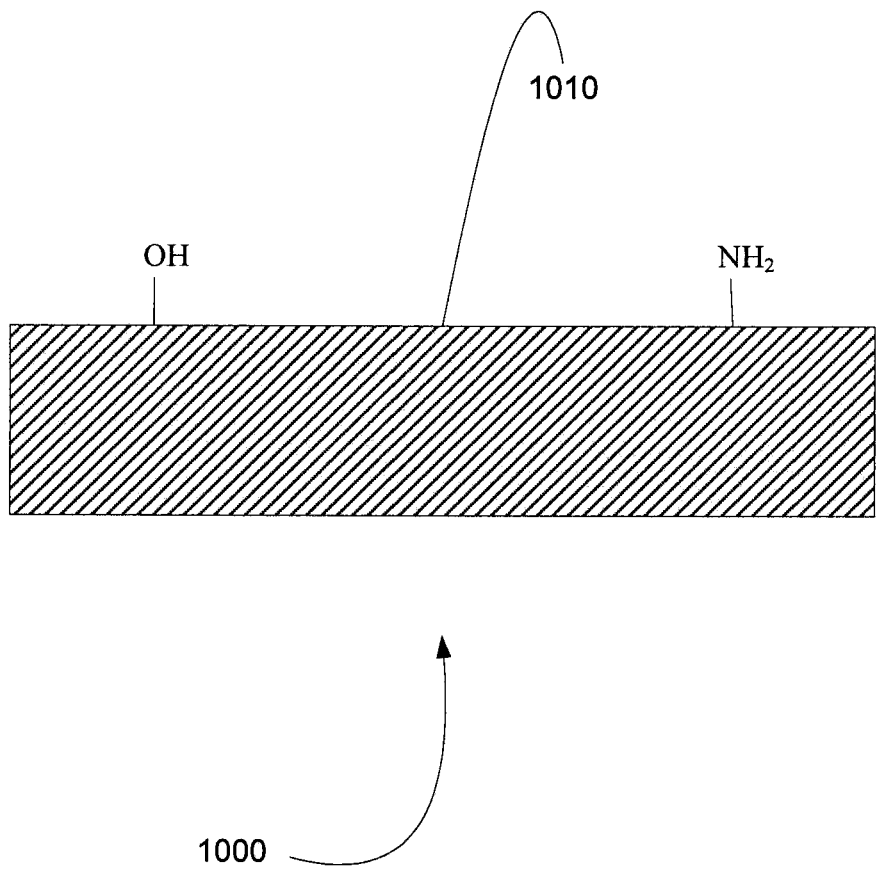
FIG. 1A is a cross-sectional view showing one surface of a fabric.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The present invention is described as including fabrics comprising a photocatalyst composition to produce singlet oxygen from ambient oxygen. This description should not be taken as limiting. Applicant's invention includes any substrate comprising a surface, wherein a photocatalyst to produce singlet oxygen from ambient oxygen is chemically attached to that surface. Other substrates include, without limitation, plastic films, glass, metal, wood, paper, and combinations thereof.

Applicant's fabric comprises a coating comprising a photocatalyst which generates a singlet oxygen from ambient oxygen, in optional combination with a singlet oxygen trap. By "singlet oxygen trap," Applicant means a compound that reacts reversibly with singlet oxygen. The use of a photocatalyst to generate singlet oxygen from ambient oxygen, in combination with a singlet oxygen trap is taught in U.S. Pat. No. 7,259,122 (the '122 patent), in the name of Lombardi, and is hereby incorporated herein by reference in its entirety.

In certain embodiments, Applicant's fabric comprises Applicant's coating composition described disposed over one or more surfaces thereof. By "fabric," Applicant means a flexible, planar material formed by weaving or felting or knitting or crocheting natural and/or synthetic fibers.

In certain embodiments, Applicant's fabric generates singlet oxygen using Reaction Scheme "A", below. Upon absorption of light, the photocatalyst undergoes electronic excitation to a singlet state followed by electron reorganization to form the excited triplet state. Triplet photocatalyst transfers energy to ambient triplet oxygen to form reactive singlet oxygen. The singlet oxygen generated ($^1O_2$), is the reactive species capable eliminating odors. In certain embodiments, the singlet oxygen oxidizes odoriferous compounds rendering those materials odor-free. In certain embodiments, the singlet oxygen oxidizes materials and/or pathogens that release one or more odoriferous compounds.

photocatalyst+light→$^1$photocatalyst→$^3$photocatalyst
$^3$photocatalyst+$^3O_2$→
photocatalyst+$^1O_2$       REACTION SCHEME "A"

In various embodiments, Applicant's fabric comprises a Photocatalyst Composition which comprises a Photocatalyst and one or more pendant silyl ester groups. Such pendant silyl ester groups facilitate formation of a stable covalent attachment of Applicant's Photocatalyst Composition to a wide variety of fabric surfaces.

In various embodiments, Applicant react a substituted Photocatalyst with one or more of silyl ester compounds 4, 5, 6, 7, and/or 8, to covalently bond one or more pendant silyl ester functionalities II to form Applicant's Photocatalyst Composition.

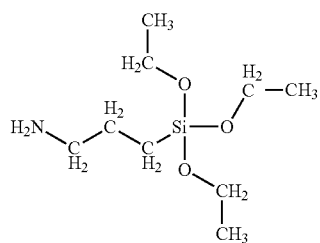

4

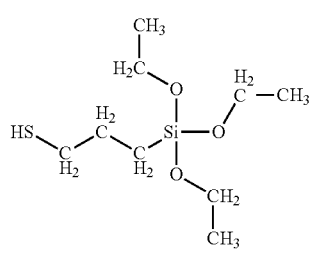

5

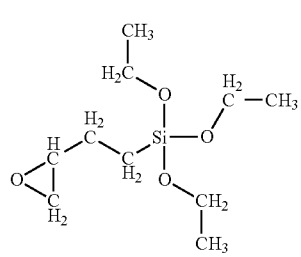

6

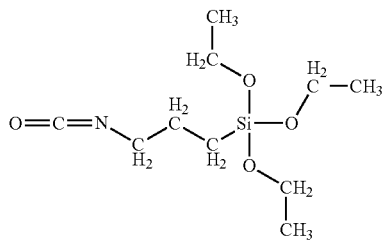

7

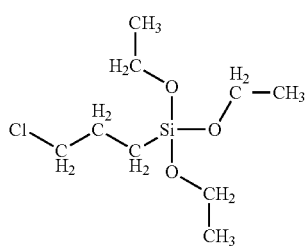

8

In various embodiments, Applicant's Photocatalyst Composition comprises a substituted photocatalyst selected from the group consisting of substituted Acetonaphthones, substituted Acetophenonse, substituted Acridines, substituted Anthracenes, substituted Anthraquinones, substituted Anthrones, substituted Azulenes, substituted Benzils, substituted Benzophenones, substituted Benzopyranones, substituted Benzoquinones, substituted Flavones, substituted Camphoroquinone, substituted Chrysenes, substituted 7-Dehydrocholesterols, substituted Ergosterols, substituted Fluorenes, substituted Fluorenones, substituted Eosins, substituted Fluoresceins, substituted Phloxines, substituted Rose Bengals, substituted Erythrosins, substituted Indoles, substituted Naphthalenes, substituted Phenanthrenes, substituted Phenazines, substituted Thionines, substituted Azures, substituted Toluidine Blue, substituted Methylene Blues, substituted Pyrenes, substituted Quinoxalines, substituted Retinols, substituted Riboflavins, substituted Rubrenes, substituted Bacteriochlorophylls, substituted Chlorophylls, substituted Pheophytins, substituted Pheophorbides, substituted Protochlorophylls, substituted Coproporphyrins, substituted Fullerenes, substituted Porphyrins, substituted Metallo Porphyrins, substituted Porphines, substituted Rubrenes, and substituted Phthalocyanines, Examples 1 through 42 summarize the preparations of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189. Examples 1-42 are presented to further illustrate to persons skilled in the art how to make and use the invention. These examples are not intended as a limitation, however, upon the scope of the invention, which is defined by the scope of the claims appended hereto.

EXAMPLE 1

Acetonaphthone CAS: 93-08-3; Φ~0.5-0.7

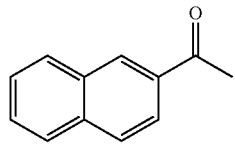

Reaction of substituted Acetonaphthone Photocatalyst 20A with aminosilyl ester 4 gives substituted Acetonaphthone Photocatalyst Composition 21. Reaction of substituted Acetonaphthone Photocatalyst 20A with mercaptosilyl ester 5 gives substituted Acetonaphthone Photocatalyst Composition 22.

Reaction of substituted Acetonaphthone Photocatalyst 20B with aminosilyl ester 4 gives substituted Acetonaphthone Photocatalyst Composition 21. Reaction of substituted Acetonaphthone Photocatalyst 20B with mercaptosilyl ester 5 gives substituted Acetonaphthone Photocatalyst Composition 22.

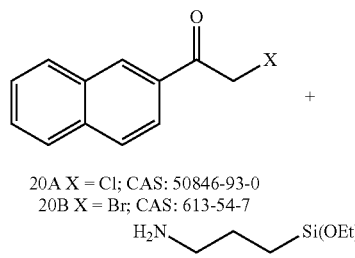

20A X = Cl; CAS: 50846-93-0
20B X = Br; CAS: 613-54-7

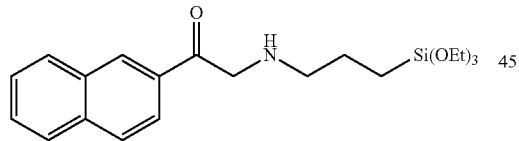

21

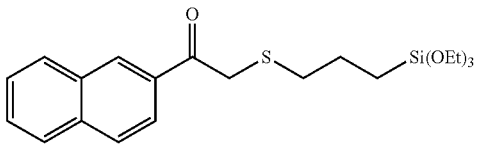

22

Reaction of substituted Acetonaphthone Photocatalyst 20C with epoxysilyl ester 6 gives substituted Acetonaphthone Photocatalyst Composition 23. Reaction of substituted Acetonaphthone Photocatalyst 20C with isocyanatosilyl ester 7 gives substituted Acetonaphthone Photocatalyst Composition 24. Reaction of substituted Acetonaphthone Photocatalyst 20C with chlorosilyl ester 7 gives substituted Acetonaphthone Photocatalyst Composition 25.

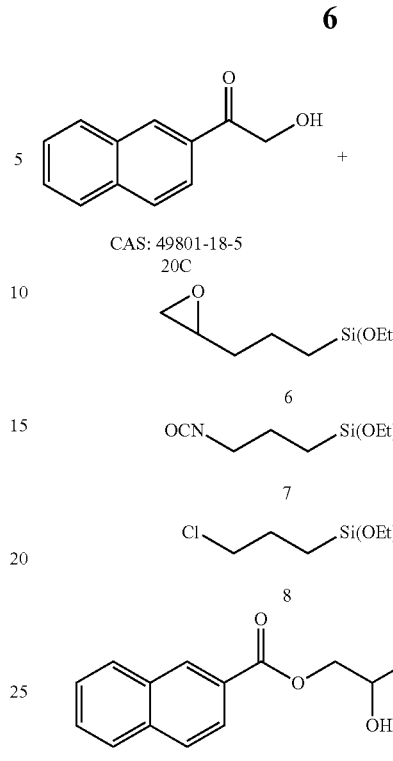

CAS: 49801-18-5
20C

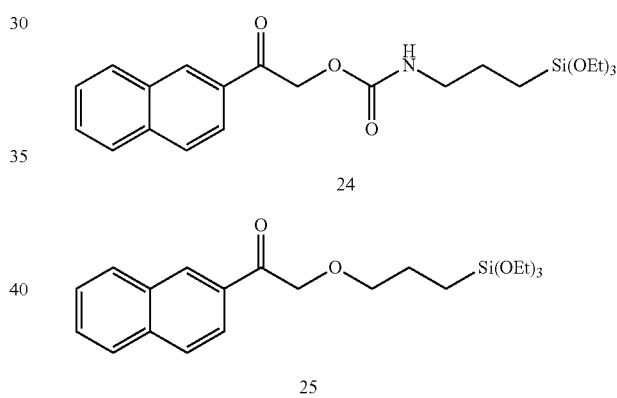

EXAMPLE 2

Acridine CAS: 260-94-6; Φ~0.8

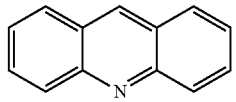 [SMILES: c1ccc2nc3ccccc3cc2c1]

Reaction of substituted Acridine photocatalyst 26A with epoxysilyl ester 6 gives substituted Acridine Photocatalyst Composition 29. Reaction of substituted photocatalyst 26A with isocyanatosilyl ester 7 gives Photocatalyst Composition 30.

Reaction of substituted photocatalyst 26B with epoxysilyl ester 6 gives Photocatalyst Composition 28. Reaction of substituted photocatalyst 26B with isocyanatosilyl ester 7 gives Photocatalyst Composition 27.

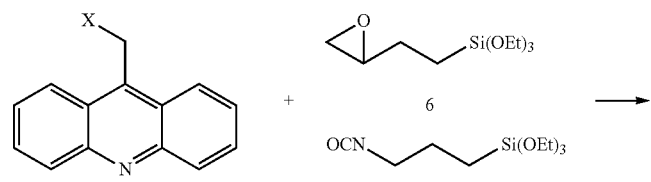
26A X = NH₂; CAS: 34273-93-3
26B X = OH; CAS: 35426-11-0
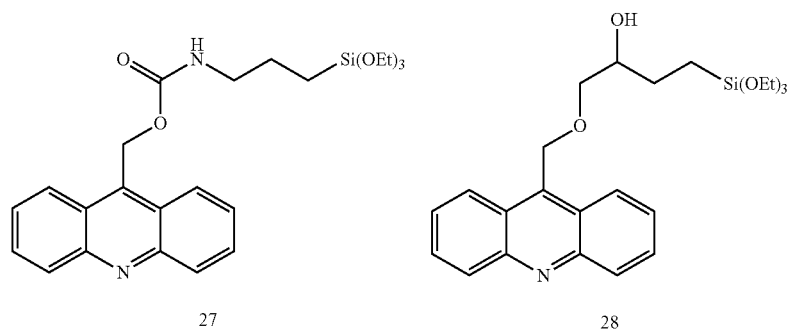
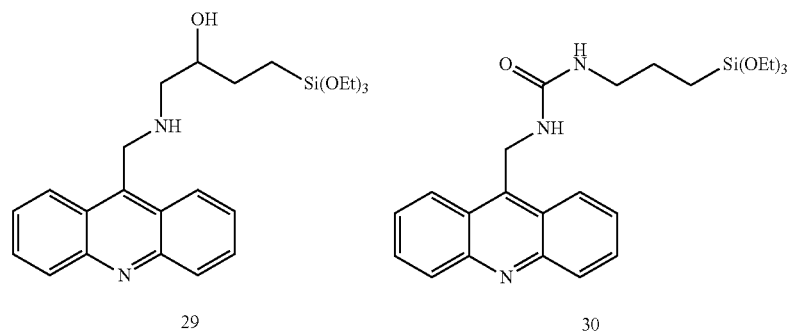
Reaction of substituted photocatalyst 31 with aminosilyl ester 4 gives Photocatalyst Composition 32. Reaction of substituted photocatalyst 31 with mercaptosilyl ester 5 gives Photocatalyst Composition 33.
-continued
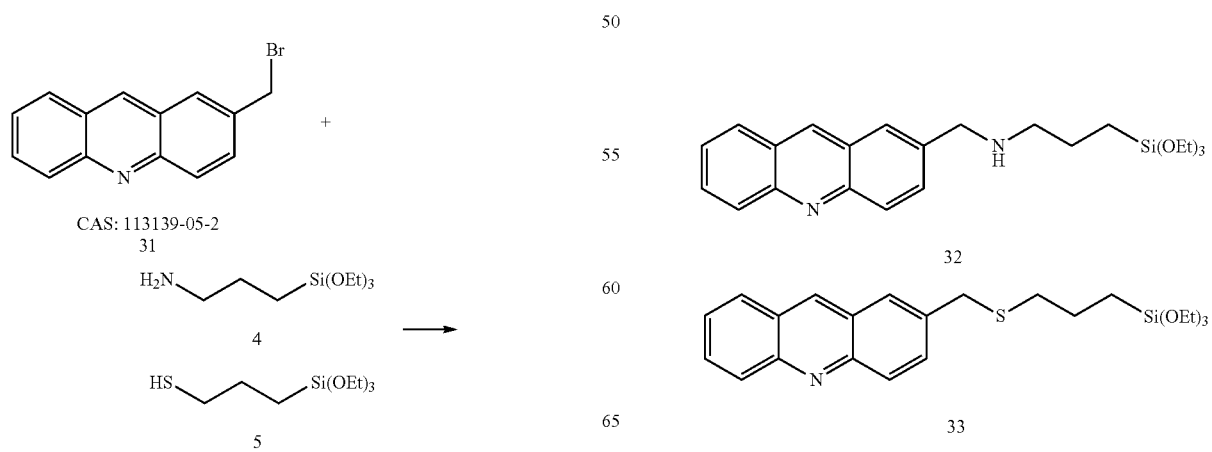

EXAMPLE 3

Flavone CAS: 525-82-6; Φ~0.5

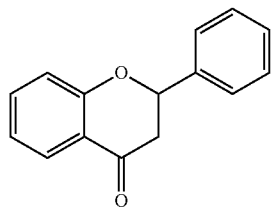 [SMILES: O=C1CC(c2ccccc2)Oc2ccccc21]

Reaction of methyl substituted Flavone Photocatalyst 34 with N-bromo succinimide gives brominated Flavone Photocatalyst 35. Reaction of brominated substituted Flavone Photocatalyst 35 with aminosilyl ester 4 gives substituted Flavone Photocatalyst Composition 36. Reaction of brominated Flavone photocatalyst 35 with mercaptosilyl ester 5 gives substituted Flavone Photocatalyst Composition 37.

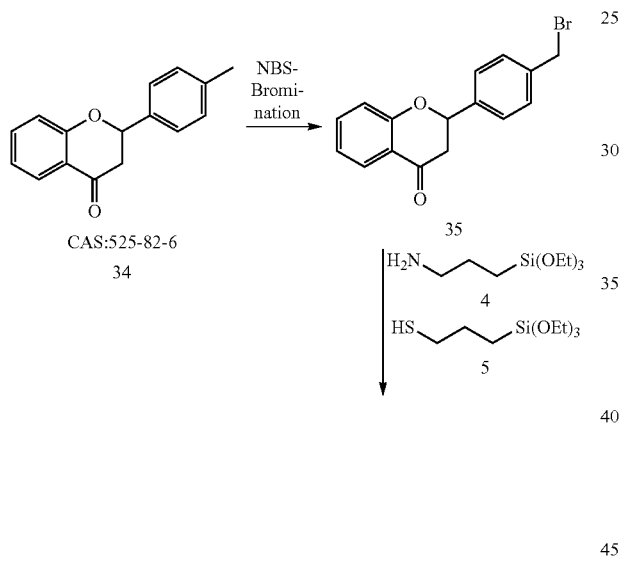

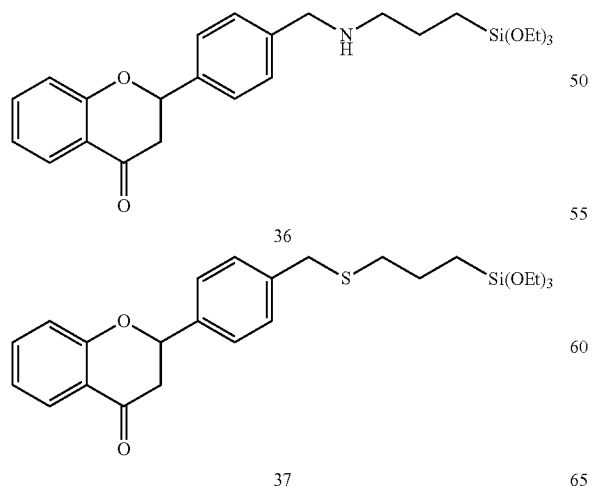

EXAMPLE 4

Camphoroquinone CAS 10373-78-1; Φ~0.8

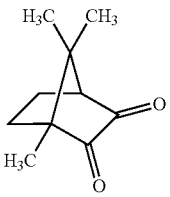

CAS ☐10373–78–1

Reaction of substituted Camphoroquinone Photocatalyst 38 with aminosilyl ester 4 gives substituted Camphoroquinone Photocatalyst Composition 39. Reaction of substituted Camphoroquinone Photocatalyst 38 with mercaptosilyl ester 5 gives substituted Camphoroquinone Photocatalyst Composition 40.

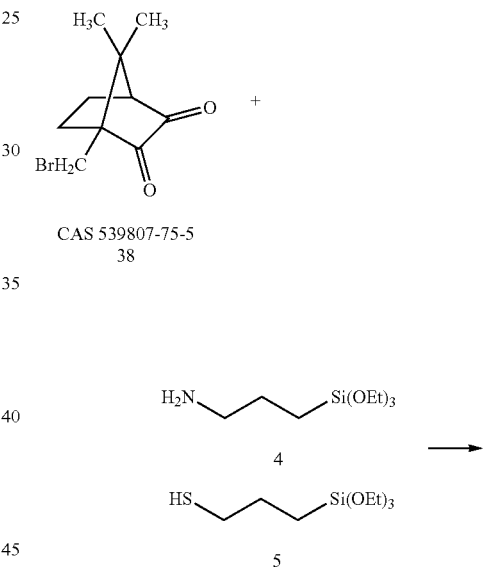

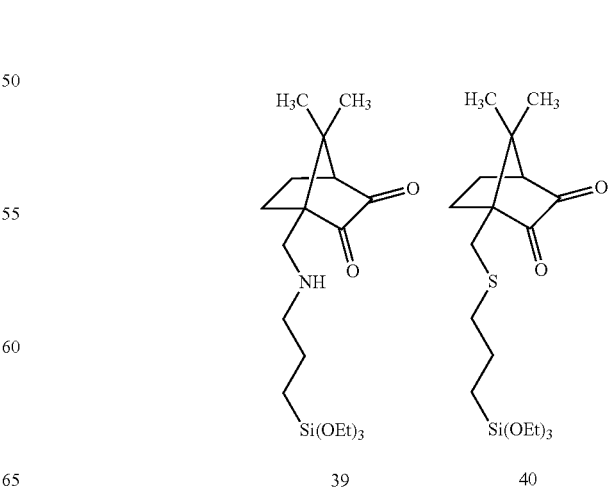

EXAMPLE 5

Chrysene CAS 218-01-9; Φ~0.6

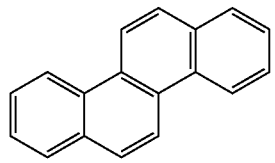

CAS 218-01-9

Bromination of substituted Chrysene Photocatalyst 41 gives brominated compound 42. Reaction of substituted Chrysene Photocatalyst 42 with aminosilyl ester 4 gives substituted Chrysene Photocatalyst Composition 43. Reaction of substituted Chrysene Photocatalyst 42 with mercaptosilyl ester 5 gives substituted Chrysene Photocatalyst Composition 44.

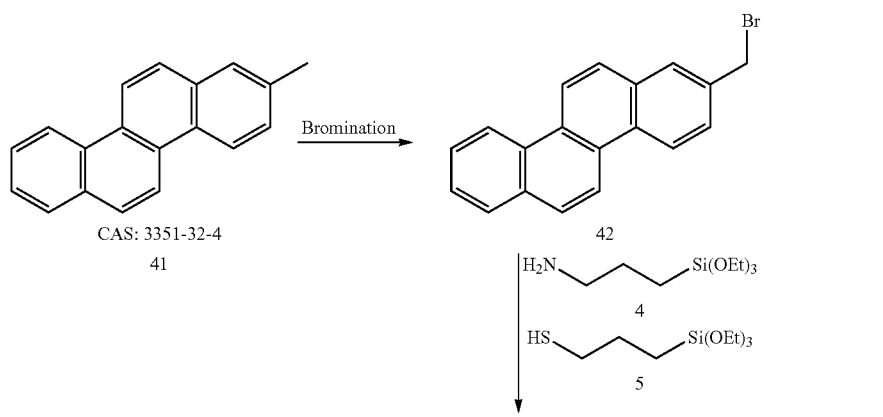

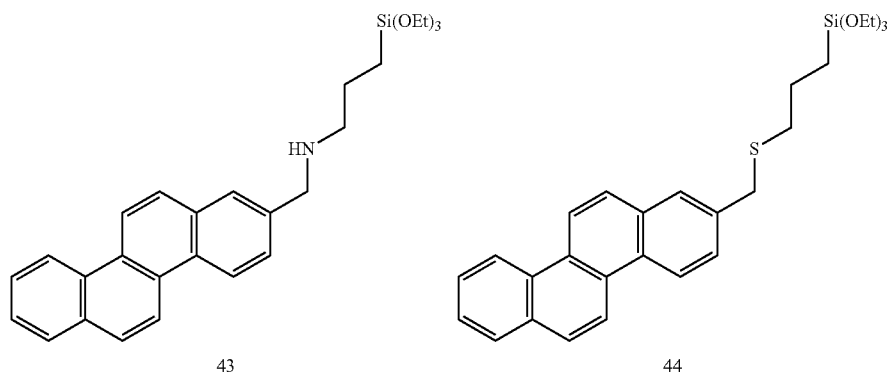

EXAMPLE 6

7-Dehydrocholesterol CAS: 434-16-2; Φ~0.8

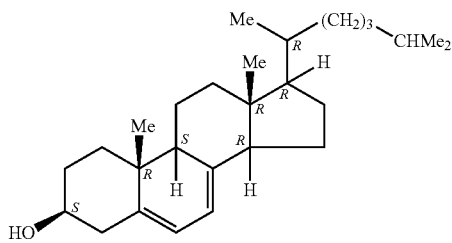

Reaction of substituted 7-Dehydrocholesterol photocatalyst 45 with epoxysilyl ester 6 gives substituted 7-Dehydrocholesterol Photocatalyst Composition 46. Reaction of substituted 7-Dehydrocholesterol Photocatalyst 46 with isocyanatosilyl ester 7 gives substituted 7-Dehydrocholesterol Photocatalyst Composition 47. Reaction of substituted 7-Dehydrocholesterol photocatalyst 45 with chlorosilyl ester 8 gives substituted 7-Dehydrocholesterol Photocatalyst Composition 48.

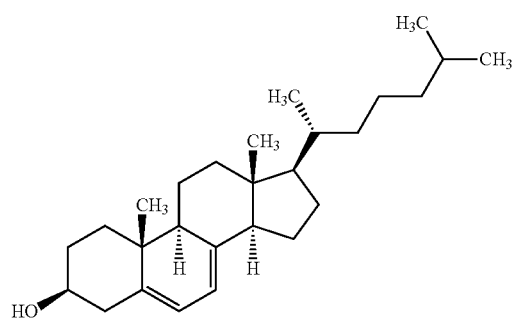

CAS 434-16-2
45

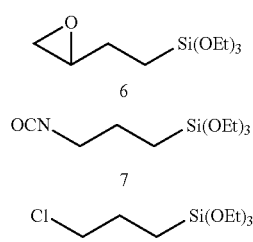

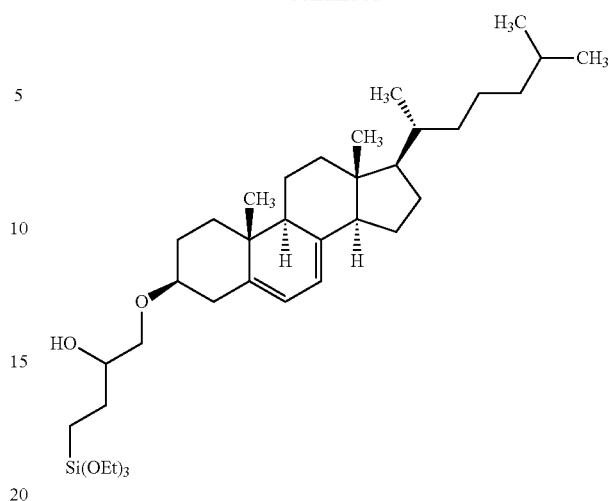

46

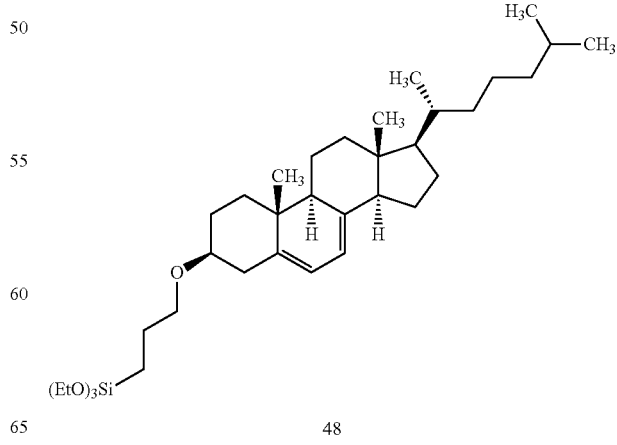

EXAMPLE 7

Ergosterol CAS: 57-87-4; Φ~0.8

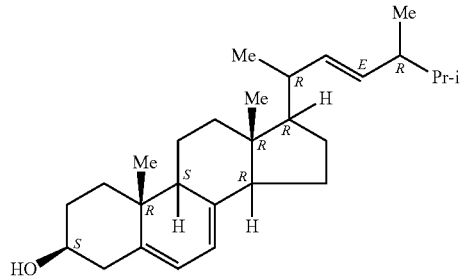

Reaction of substituted Ergosterol Photocatalyst 49 with epoxysilyl ester 6 gives substituted Ergosterol Photocatalyst Composition 50. Reaction of substituted Ergosterol Photocatalyst 49 with isocyanatosilyl ester 7 gives substituted Ergosterol Photocatalyst Composition 51. Reaction of substituted Ergosterol Photocatalyst 49 with chlorosilyl ester 8 gives substituted Ergosterol Photocatalyst Composition 52.

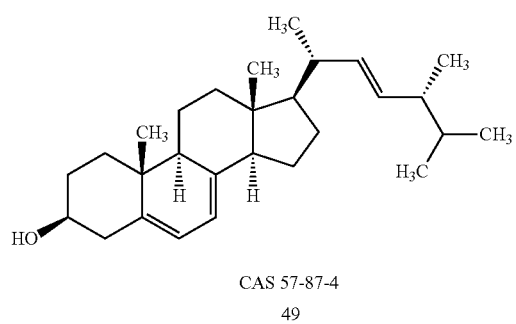

CAS 57-87-4
49

+

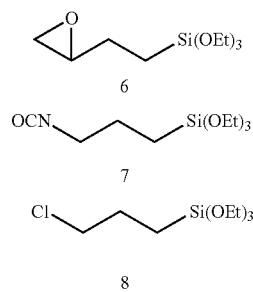

6

7

8

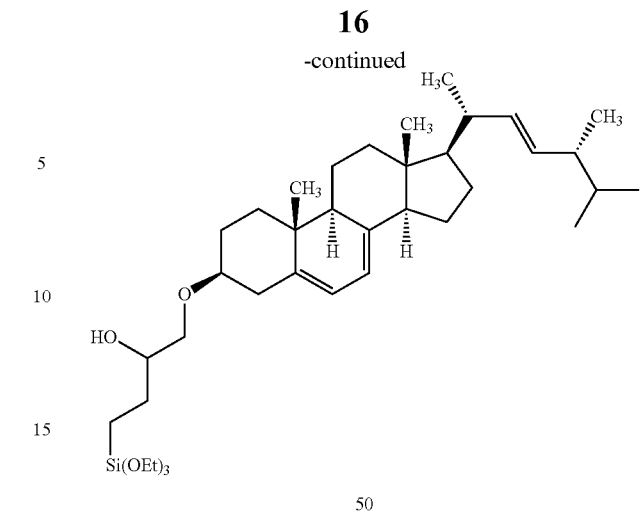

50

51

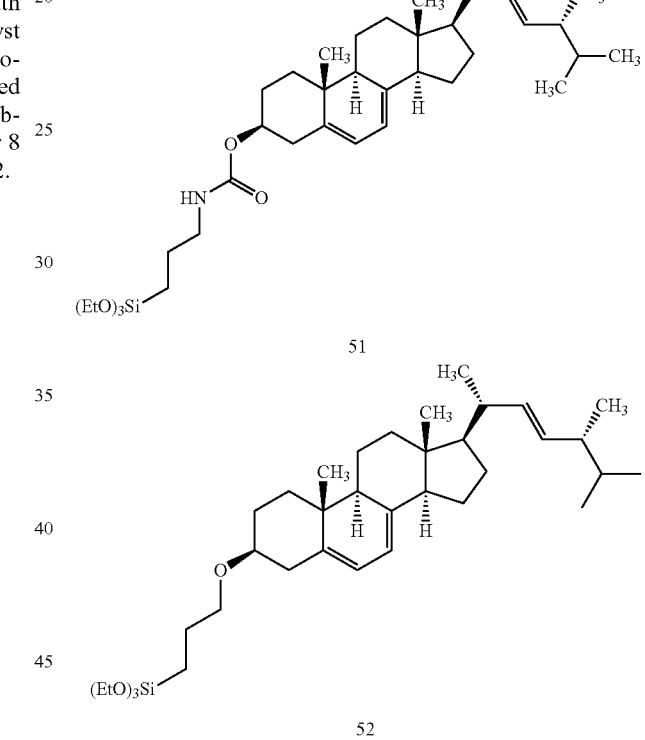

52

EXAMPLE 8

Fluorene CAS: 86-73-7; Φ~1

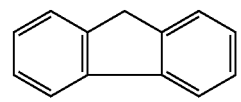

Reaction of substituted Fluorene Photocatalyst 53A with epoxysilyl ester 6 gives substituted Fluorene Photocatalyst Composition 54. Reaction of substituted Fluorene Photocatalyst 53A with isocyanatosilyl ester 7 gives substituted Fluorene Photocatalyst Composition 55.

Reaction of substituted Fluorene Photocatalyst 53B with epoxysilyl ester 6 gives substituted Fluorene Photocatalyst Composition 56. Reaction of substituted Fluorene Photocatalyst 53B with isocyanatosilyl ester 7 gives substituted Fluorene Photocatalyst Composition 57.

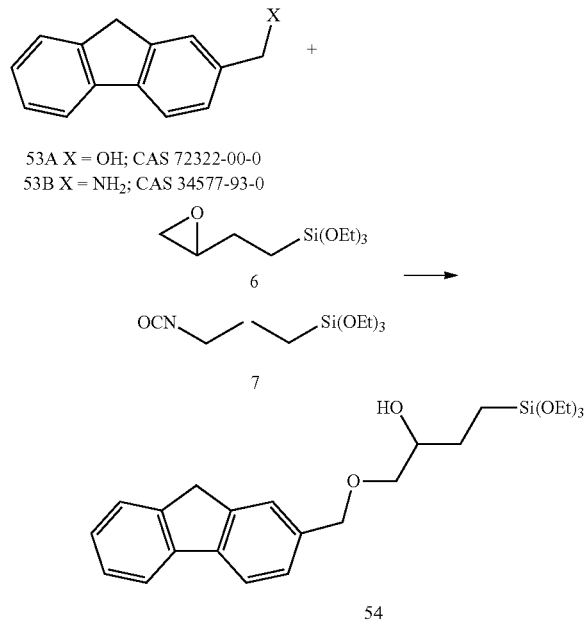

EXAMPLE 9

Fluorenone CAS: 486-25-9; Φ~0.8

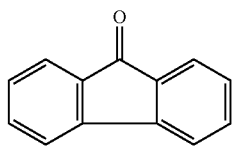 [SMILES: O=C1c2ccccc2-c2ccccc21]

Reaction of substituted Fluorenone Photocatalyst 58 with aminosilyl ester 4 gives substituted Fluorenone Photocatalyst Composition 59. Reaction of substituted Fluorenone Photocatalyst 58 with mercaptosilyl ester 5 gives substituted Fluorenone Photocatalyst Composition 60.

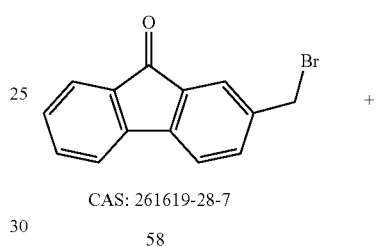

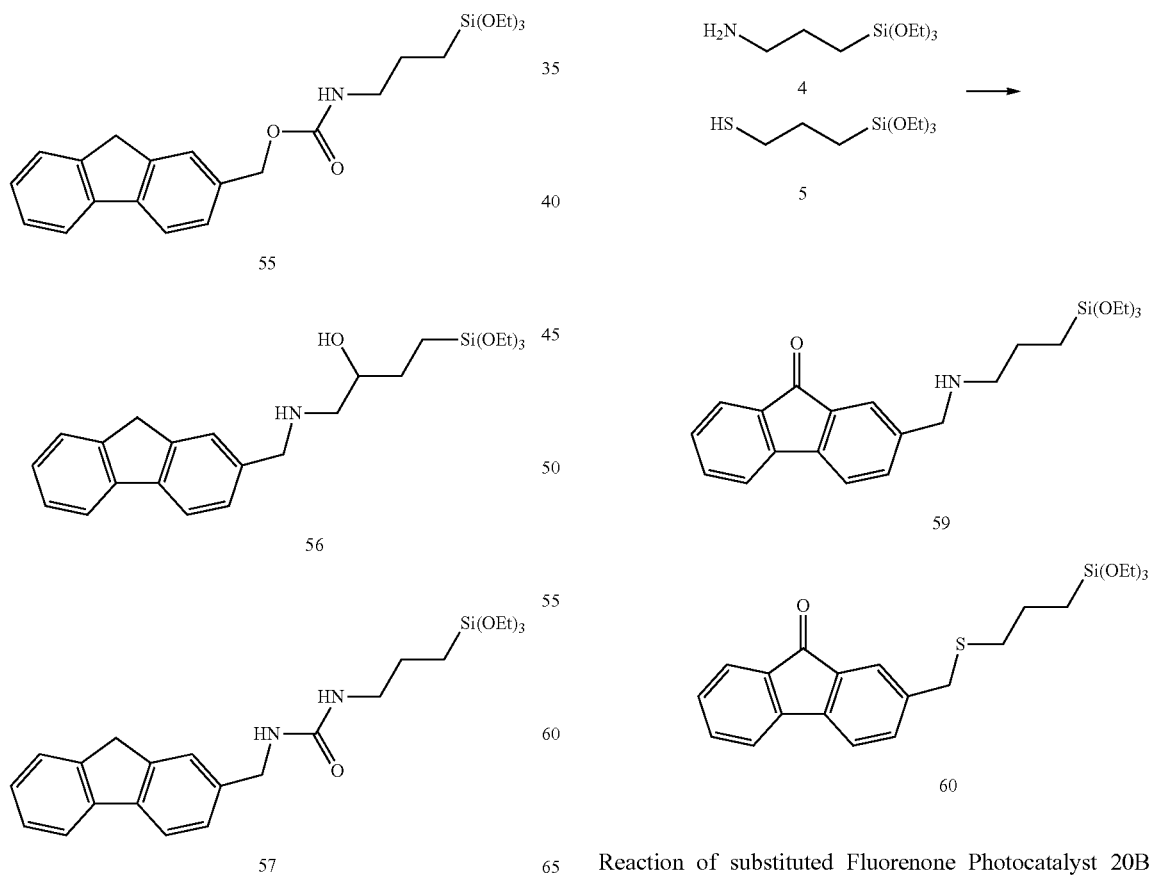

Reaction of substituted Fluorenone Photocatalyst 20B with aminosilyl ester 4 gives substituted Fluorenone Photocatalyst Composition 62.

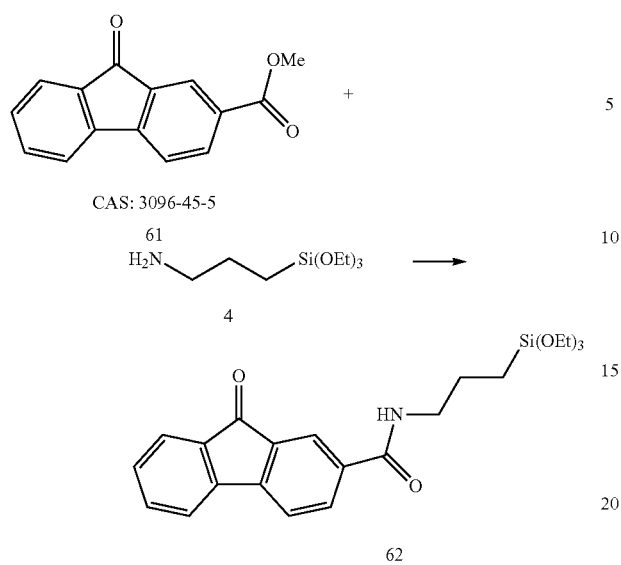

CAS: 3096-45-5
61

4

62

EXAMPLE 10

Eosin B CAS: 548-24-3; Φ~0.3-0.5

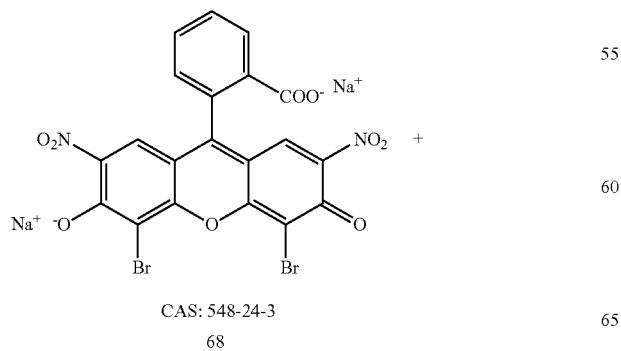

Reaction of substituted Eosin B Photocatalyst 63 with epoxysilyl ester 6 gives substituted Eosin B Photocatalyst Composition 64. Reaction of substituted Eosin B Photocatalyst 63 with isocyanatosilyl ester 7 gives substituted Eosin B Photocatalyst Composition 65. Reaction of substituted Eosin B Photocatalyst 63 with chlorosilyl ester 8 gives substituted Eosin B Photocatalyst Composition 66.

CAS: 548-24-3
68

-continued

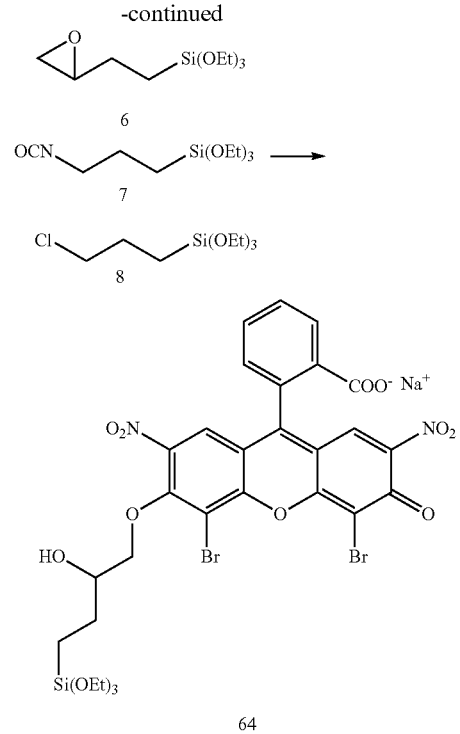

6

7

8

64

65

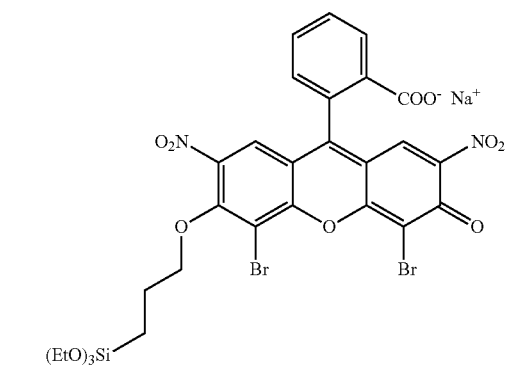

66

EXAMPLE 11

DiiodoFluorescein CAS: 33239-19-9; Φ~0.3-0.5

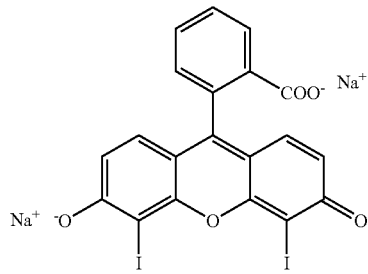

Reaction of substituted DiiodoFluorescein Photocatalyst 67 with epoxysilyl ester 6 gives substituted DiiodoFluorescein Photocatalyst Composition 68. Reaction of substituted DiiodoFluorescein Photocatalyst 67 with isocyanatosilyl ester 7 gives substituted DiiodoFluorescein Photocatalyst Composition 69 Reaction of substituted DiiodoFluorescein photocatalyst 67 with chlorosilyl ester 8 gives substituted DiiodoFluorescein Photocatalyst Composition 70.

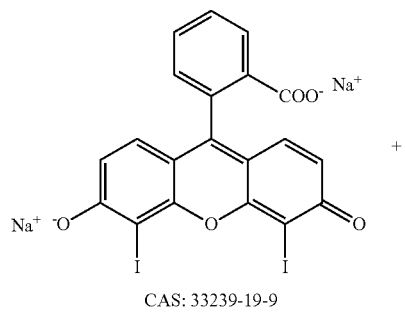

CAS: 33239-19-9
67

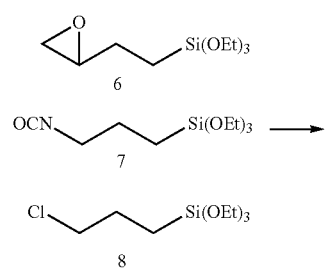

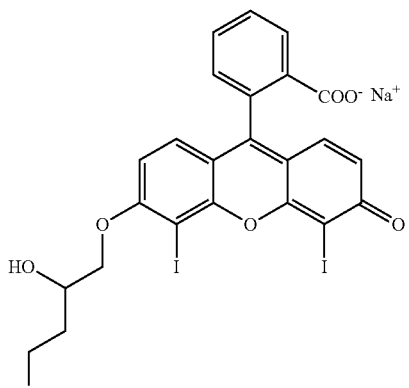

68

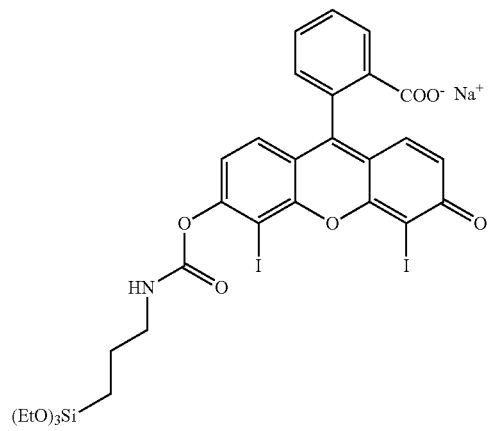

69

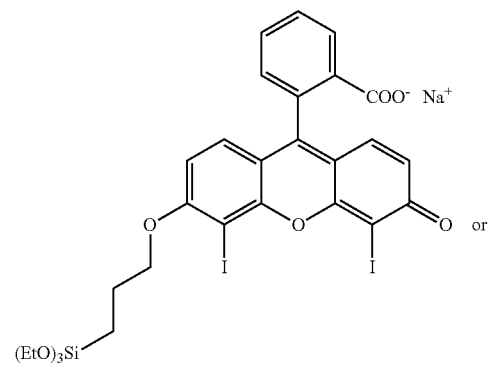

70

EXAMPLE 12

Eosin Y CAS: 17372-87-1; Φ~0.5-0.9

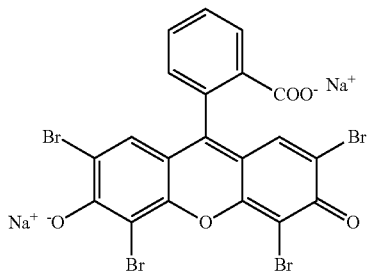

Reaction of substituted Eosin Y Photocatalyst 71 with epoxysilyl ester 6 gives substituted Eosin Y Photocatalyst Composition 72. Reaction of substituted Eosin Y Photocatalyst 71 with isocyanatosilyl ester 7 gives substituted Eosin Y Photocatalyst Composition 73. Reaction of substituted Eosin Y Photocatalyst 71 with chlorosilyl ester 8 gives substituted Eosin Y Photocatalyst Composition 74.

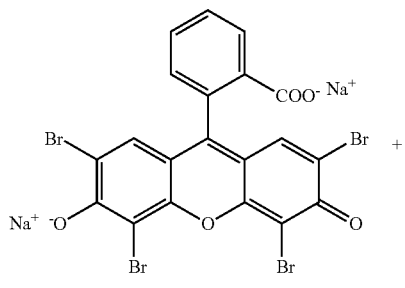

CAS: 17372-87-1
71

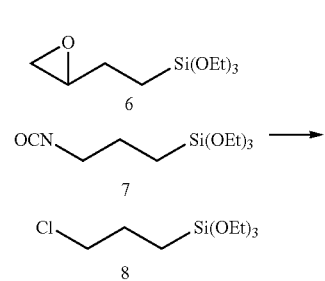

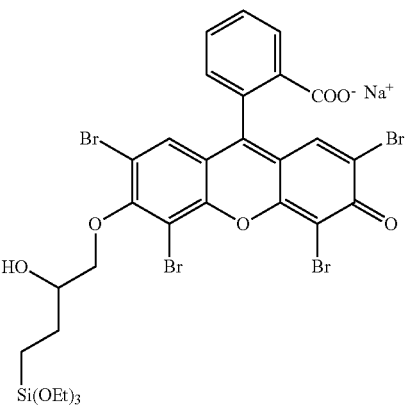

72

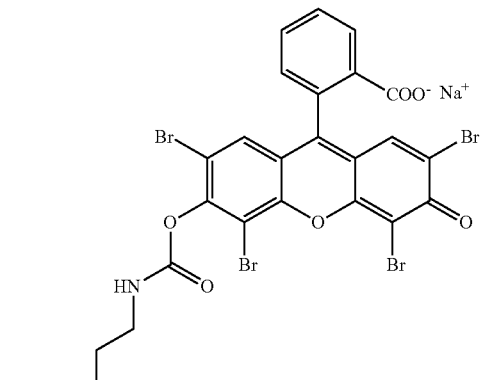

73

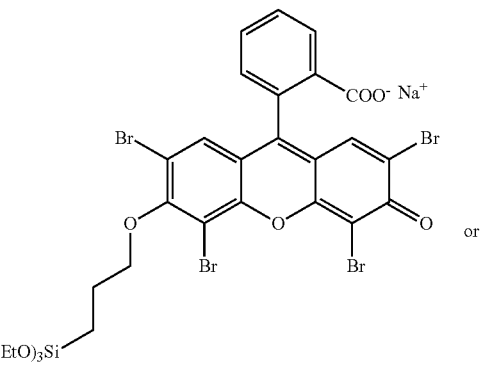

74

EXAMPLE 13

Phloxine B CAS: 18472-87-2; 0 Φ~0.4-0.6

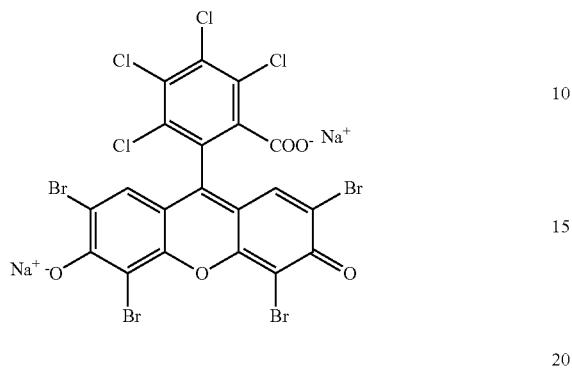

Reaction of substituted Phloxine B Photocatalyst 75 with epoxysilyl ester 6 gives substituted Phloxine B Photocatalyst Composition 76. Reaction of substituted Phloxine B Photocatalyst 75 with isocyanatosilyl ester 7 gives substituted Phloxine B Photocatalyst Composition 77. Reaction of substituted Phloxine B Photocatalyst 75 with chlorosilyl ester 8 gives substituted Phloxine B Photocatalyst Composition 78.

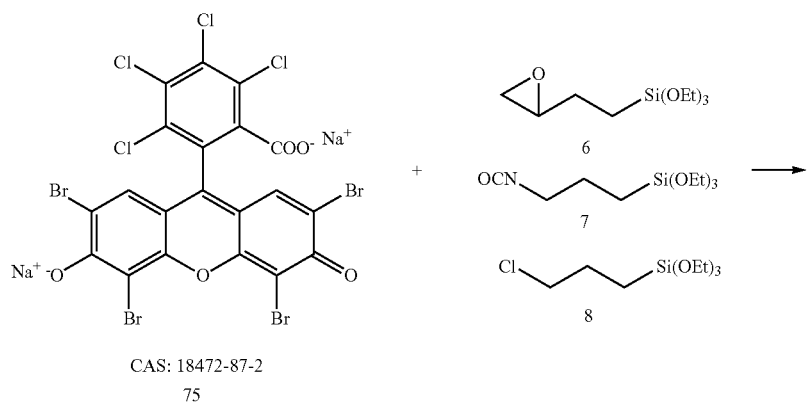

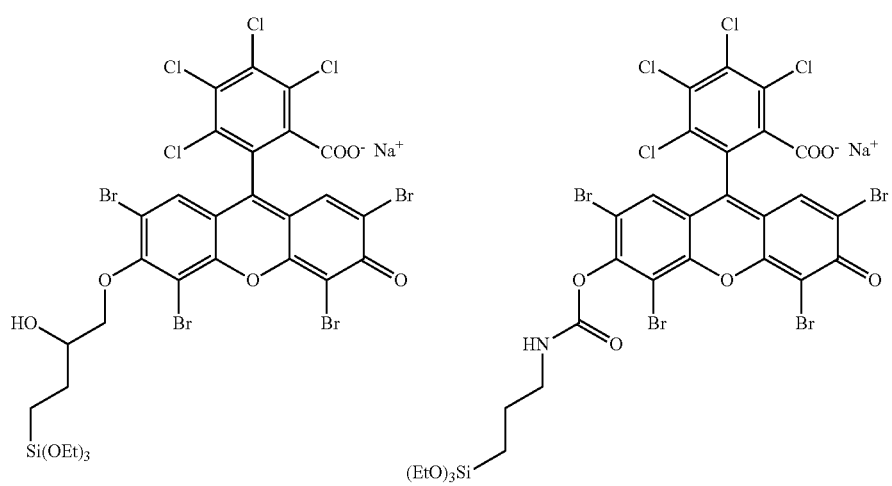

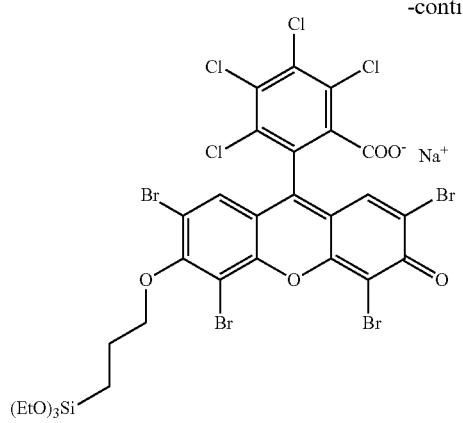

78

EXAMPLE 14

Rose Bengal DiSodium CAS: 632-69-9; Φ~0.8

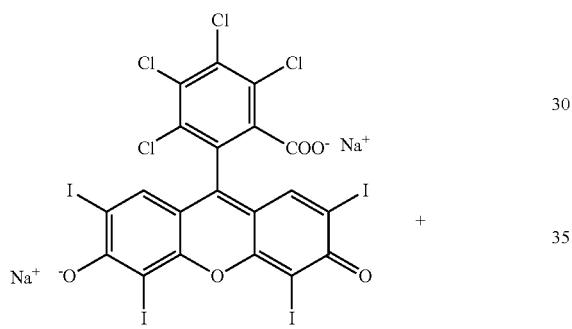

Reaction of substituted Rose Bengal DiSodium Photocatalyst 79 with epoxysilyl ester 6 gives substituted Rose Bengal DiSodium Photocatalyst Composition 80. Reaction of substituted Rose Bengal DiSodium Photocatalyst 79 with isocyanatosilyl ester 7 gives substituted Rose Bengal DiSodium Photocatalyst Composition 81. Reaction of substituted Rose Bengal DiSodium Photocatalyst 79 with chlorosilyl ester 8 gives substituted Rose Bengal DiSodium Photocatalyst Composition 82.

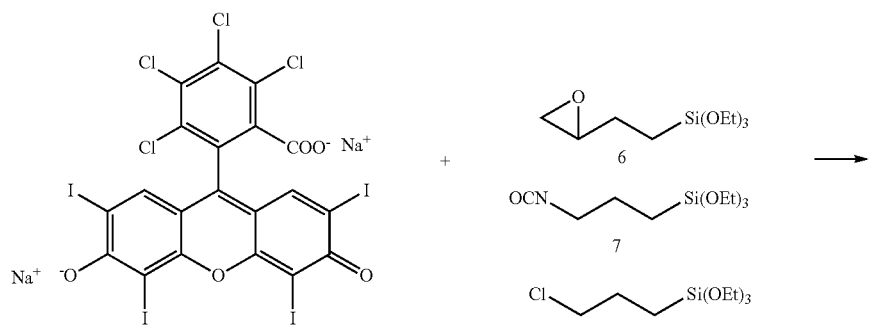

CAS: 632-69-9
79

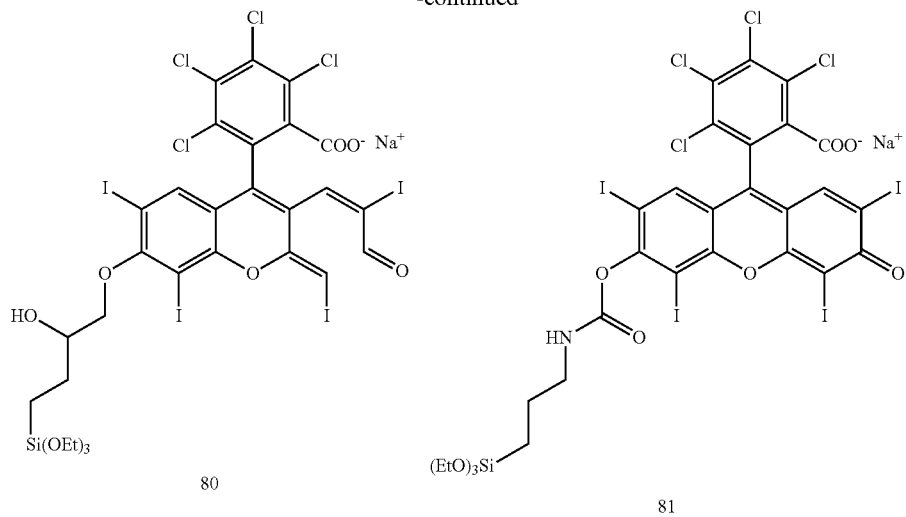

80

81

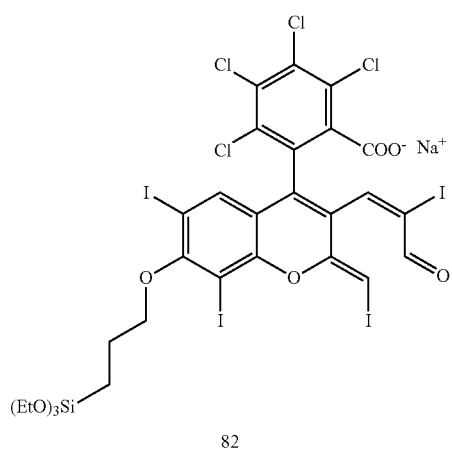

82

EXAMPLE 15

Erythrosin CAS: 16423-68-0; Φ~0.5-0.6

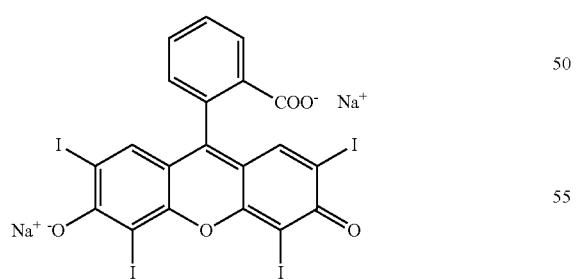

Reaction of substituted Erythrosin Photocatalyst 83 with epoxysilyl ester 6 gives substituted Erythrosin Photocatalyst Composition 84. Reaction of substituted Erythrosin photocatalyst 83 with isocyanatosilyl ester 7 gives substituted Erythrosin Photocatalyst Composition 85. Reaction of substituted Erythrosin Photocatalyst 83 with chlorosilyl ester 8 gives substituted Erythrosin Photocatalyst Composition 86.

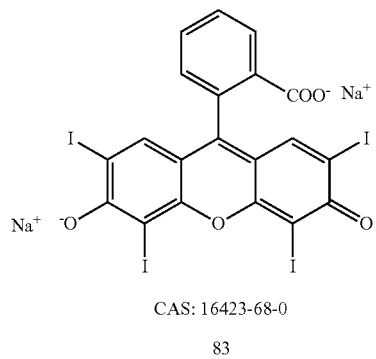
83
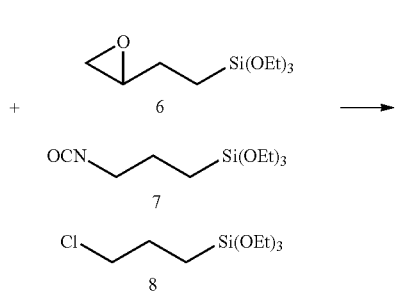
6
7
8
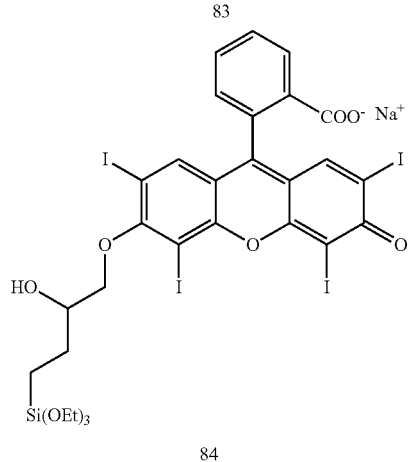
84
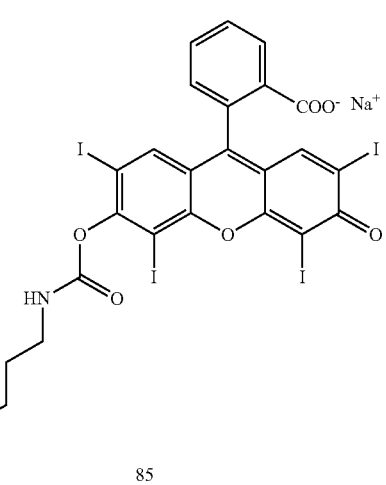
85
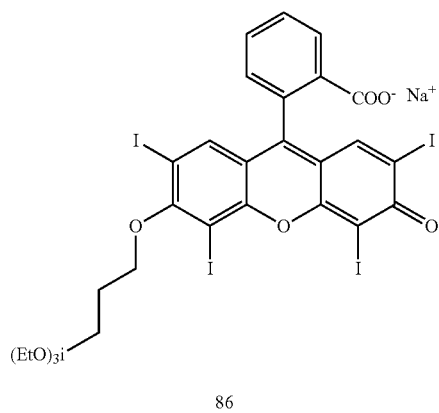
86
EXAMPLE 16
Naphthalene CAS: 91-20-3; Φ~0.7-1
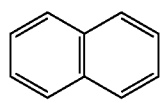
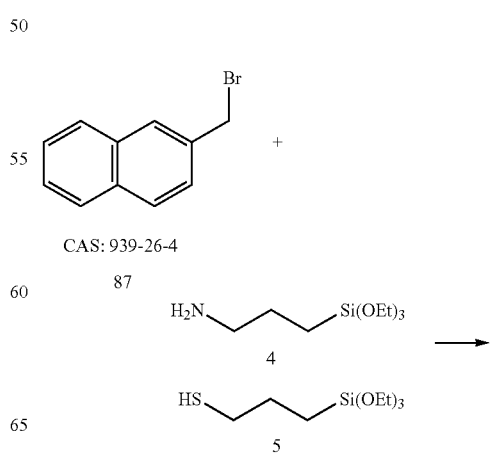
87
4
5
Reaction of substituted Naphthalene Photocatalyst 87 with aminosilyl ester 4 gives substituted Naphthalene Photocatalyst Composition 88. Reaction of substituted Naphthalene Photocatalyst 87 with mercaptosilyl ester 5 gives substituted Naphthalene Photocatalyst Composition 89

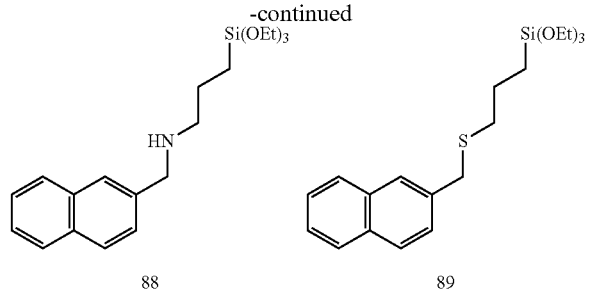

Reaction of substituted Naphthalene Photocatalyst 90A with epoxysilyl ester 6 gives substituted Naphthalene Photocatalyst Composition 91. Reaction of substituted Naphthalene Photocatalyst 90A with isocyanatosilyl ester 7 gives substituted Naphthalene Photocatalyst Composition 92.

Reaction of substituted Naphthalene Photocatalyst 90B with epoxysilyl ester 6 gives substituted Naphthalene Photocatalyst Composition 93. Reaction of substituted Naphthalene Photocatalyst 90B with isocyanatosilyl ester 7 gives substituted Naphthalene Photocatalyst Composition 94.

EXAMPLE 17

Phenanthrene CAS: 85-01-8; Φ~0.4-0.6

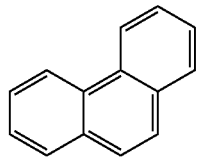 [SMILES: c1ccc2c(c1)ccc1ccccc12]

Reaction of substituted Phenanthrene Photocatalyst 20B with amino silyl ester 4 gives substituted Phenanthrene Photocatalyst Composition 96. Reaction of substituted Phenanthrene Photocatalyst 20B with mercaptosilyl ester 5 gives substituted Phenanthrene Photocatalyst Composition 97.

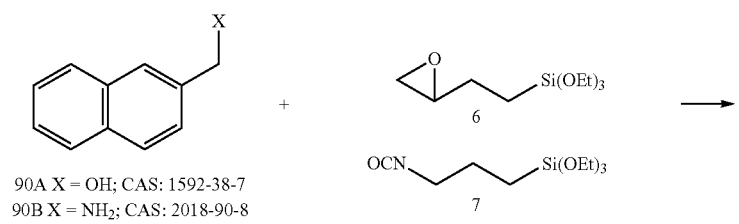

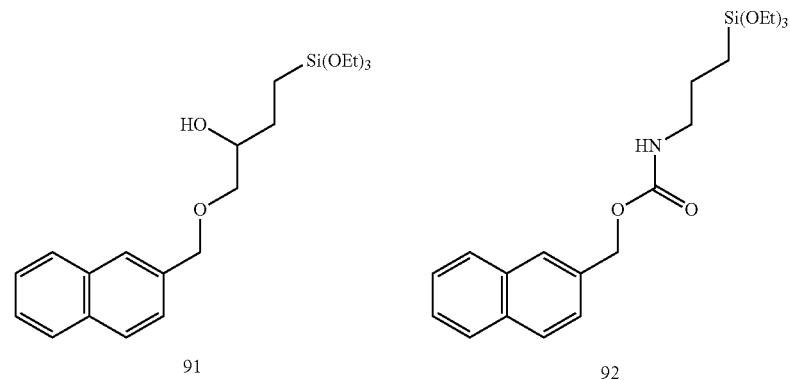

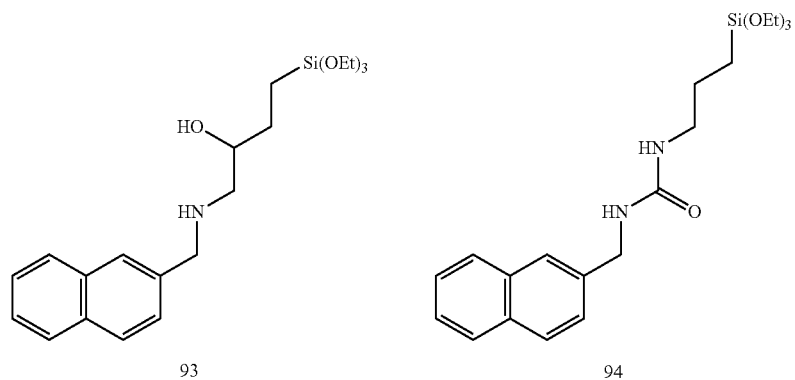

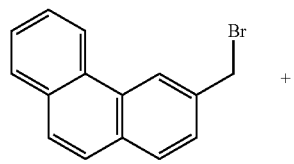

CAS: 24471-44-1
95

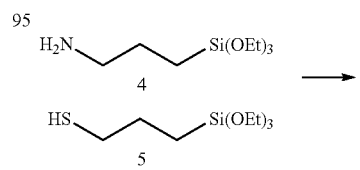

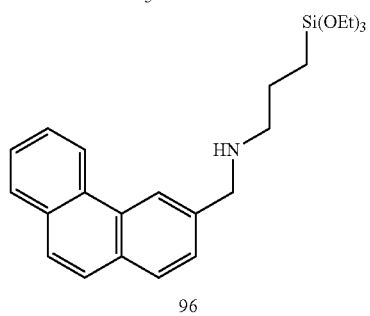

96

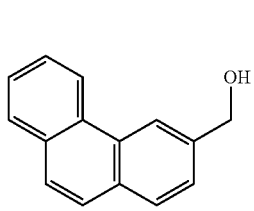

CAS: 22863-78-1
98

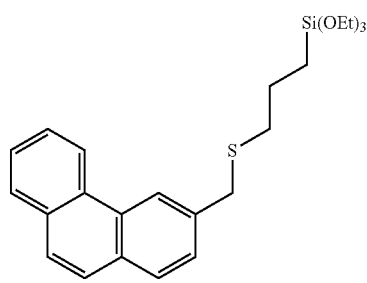

97

Reaction of substituted Phenanthrene Photocatalyst 98 with epoxysilyl ester 6 gives substituted Phenanthrene Photocatalyst Composition 99. Reaction of substituted Phenanthrene photocatalyst 98 with isocyanatosilyl ester 7 gives substituted Phenanthrene Photocatalyst Composition 100. Reaction of substituted Phenanthrene Photocatalyst 98 with chlorosilyl ester 8 gives substituted Phenanthrene Photocatalyst Composition 101.

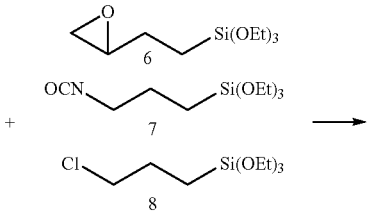

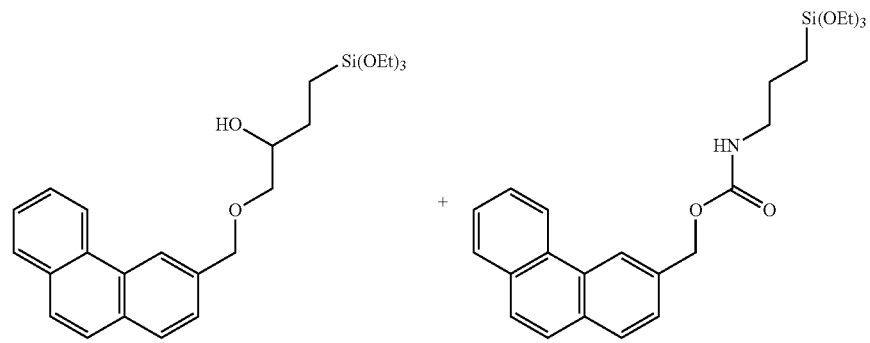

99

100

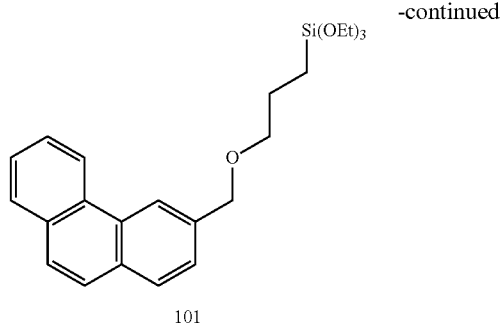

101

EXAMPLE 18

Phenazine CAS: 92-82-0; Φ~0.8-0.9

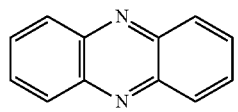 [SMILES: c1ccc2nc3ccccc3nc2c1]

Reaction of substituted Phenazine Photocatalyst 102 with aminosilyl ester 4 gives substituted Phenazine Photocatalyst Composition 103. Reaction of substituted Phenazine Photocatalyst 20B with mercaptosilyl ester 5 gives substituted Phenazine Photocatalyst Composition 104.

EXAMPLE 19

Thionine CAS: 581-64-6; Φ~0.6

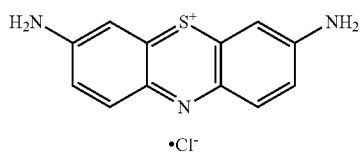

Reaction of substituted Thionine Photocatalyst 105 with epoxysilyl ester 6 gives substituted Thionine Photocatalyst Composition 106. Reaction of substituted Thionine Photocatalyst 105 with isocyanatosilyl ester 7 gives substituted Thionine Photocatalyst Composition 107. Reaction of substituted Thionine Photocatalyst 105 with chlorosilyl ester 8 gives substituted Thionine Photocatalyst Composition 108.

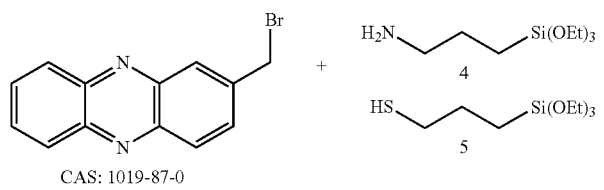

CAS: 1019-87-0
102

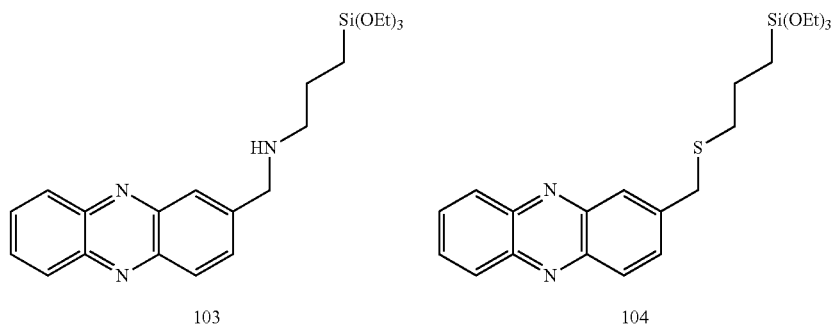

103  104

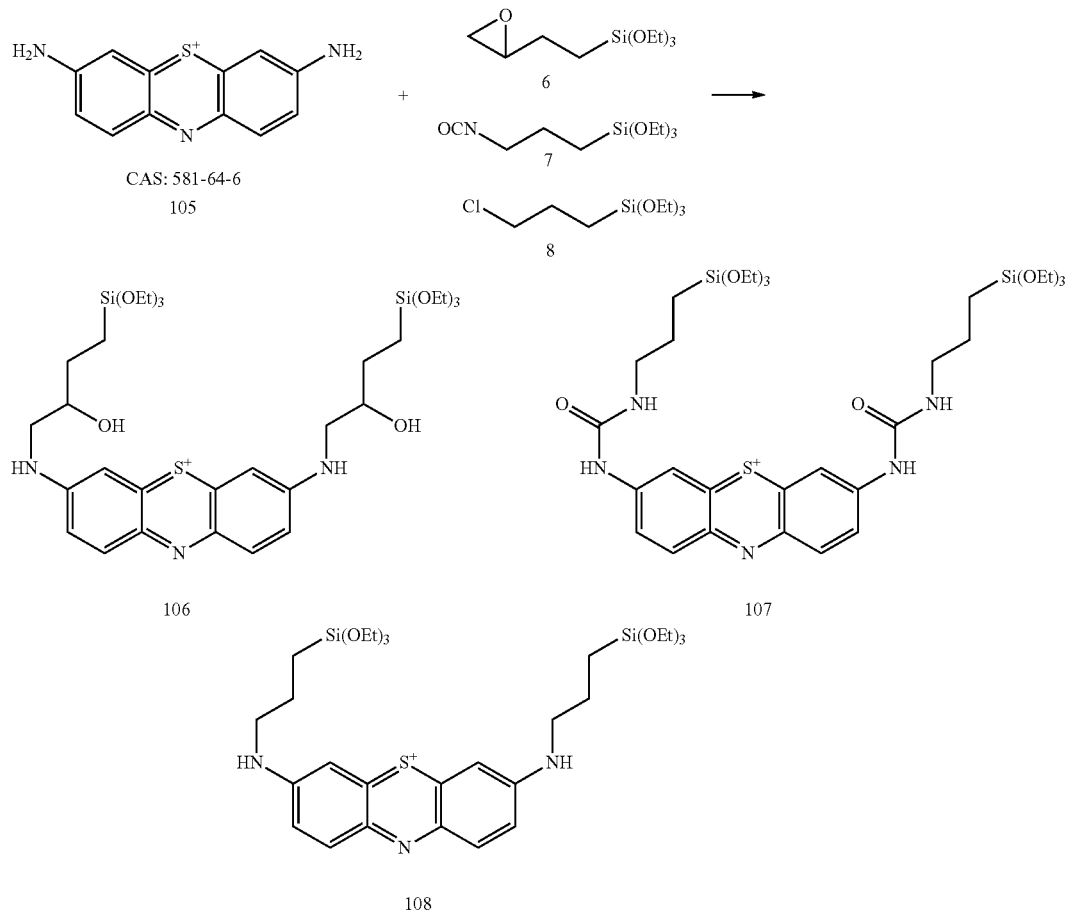

EXAMPLE 20

Azure A CAS: 531-53-3; Φ~0.8

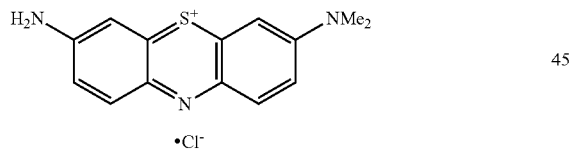

Reaction of substituted Azure A Photocatalyst 109 with epoxysilyl ester 6 gives substituted Azure A Photocatalyst Composition 110. Reaction of substituted Azure A Photocatalyst 109 with isocyanatosilyl ester 7 gives substituted Azure A Photocatalyst Composition 111. Reaction of substituted Azure A Photocatalyst 109 with chlorosilyl ester 8 gives substituted Azure A Photocatalyst Composition 112.

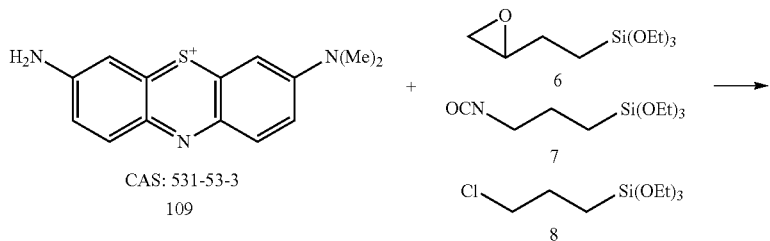

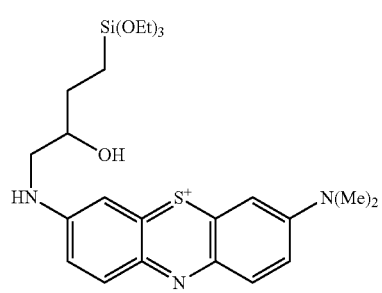

110

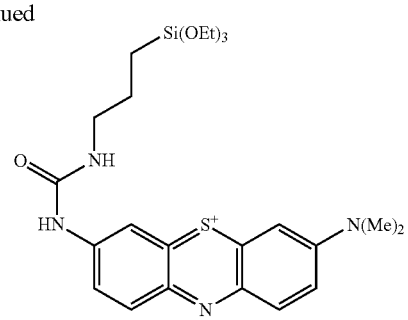

111

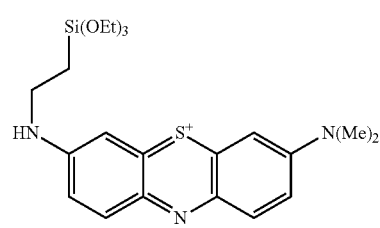

112

EXAMPLE 21

Azure C CAS: 531-57-7: Φ~0.71 relative to MB

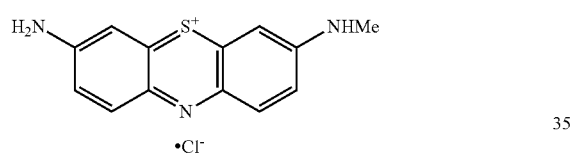

30

Reaction of substituted Azure C Photocatalyst 113 with epoxysilyl ester 6 gives substituted Azure C Photocatalyst Composition 114. Reaction of substituted Azure C Photocatalyst 113 with isocyanatosilyl ester 7 gives substituted Azure C Photocatalyst Composition 115. Reaction of substituted Azure C Photocatalyst 113 with chlorosilyl ester 8 gives substituted Azure C Photocatalyst Composition 116.

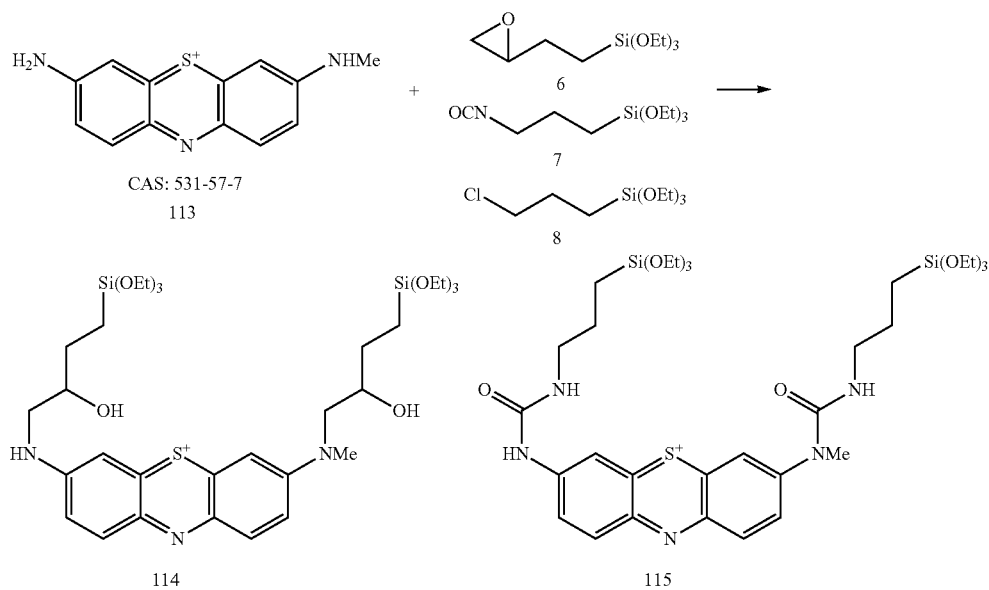

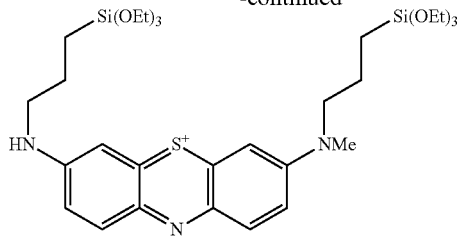

116

EXAMPLE 22

Toluidine Blue CAS: 92-31-9; Φ~0.8

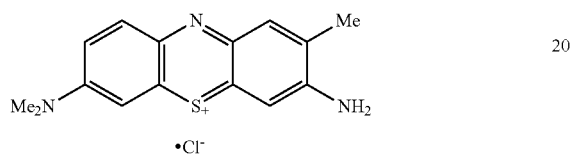

Reaction of substituted Toluidine Blue Photocatalyst 117 with epoxysilyl ester 6 gives substituted Toluidine Blue Photocatalyst Composition 118. Reaction of substituted Toluidine Blue Photocatalyst 117 with isocyanatosilyl ester 7 gives substituted Toluidine Blue Photocatalyst Composition 119. Reaction of substituted Toluidine Blue Photocatalyst 117 with chlorosilyl ester 8 gives substituted Toluidine Blue Photocatalyst Composition 120.

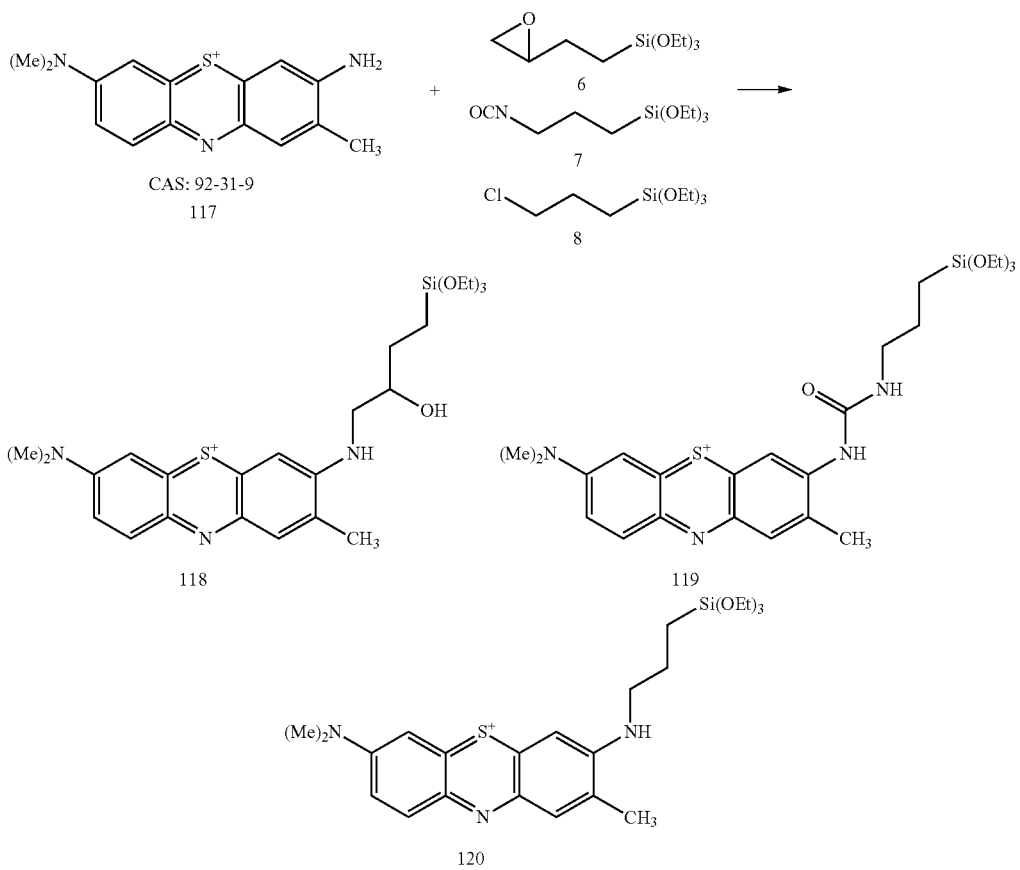

EXAMPLE 23

New Methylene Blue CAS: 1934-16-3; Φ~1.35

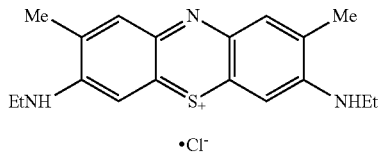

EXAMPLE 24

Pyrene CAS: 129-00-0; Φ~0.8

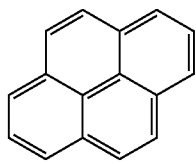 [SMILES: c1cc2ccc3cccc4ccc(c1)c2c34]

Reaction of substituted New Methylene Blue Photocatalyst 121 with epoxysilyl ester 6 gives substituted New Methylene Blue Photocatalyst Composition 122. Reaction of substituted New Methylene Blue photocatalyst 121 with isocyanatosilyl ester 7 gives substituted New Methylene Blue Photocatalyst Composition 123. Reaction of substituted New Methylene Blue Photocatalyst 121 with chlorosilyl ester 8 gives substituted New Methylene Blue Photocatalyst Composition 124.

Reaction of substituted Pyrene Photocatalyst 125 with aminosilyl ester 4 gives substituted Pyrene Photocatalyst Composition 126. Reaction of substituted Pyrene Photocatalyst 125 with mercaptosilyl ester 5 gives substituted Pyrene Photocatalyst Composition 127.

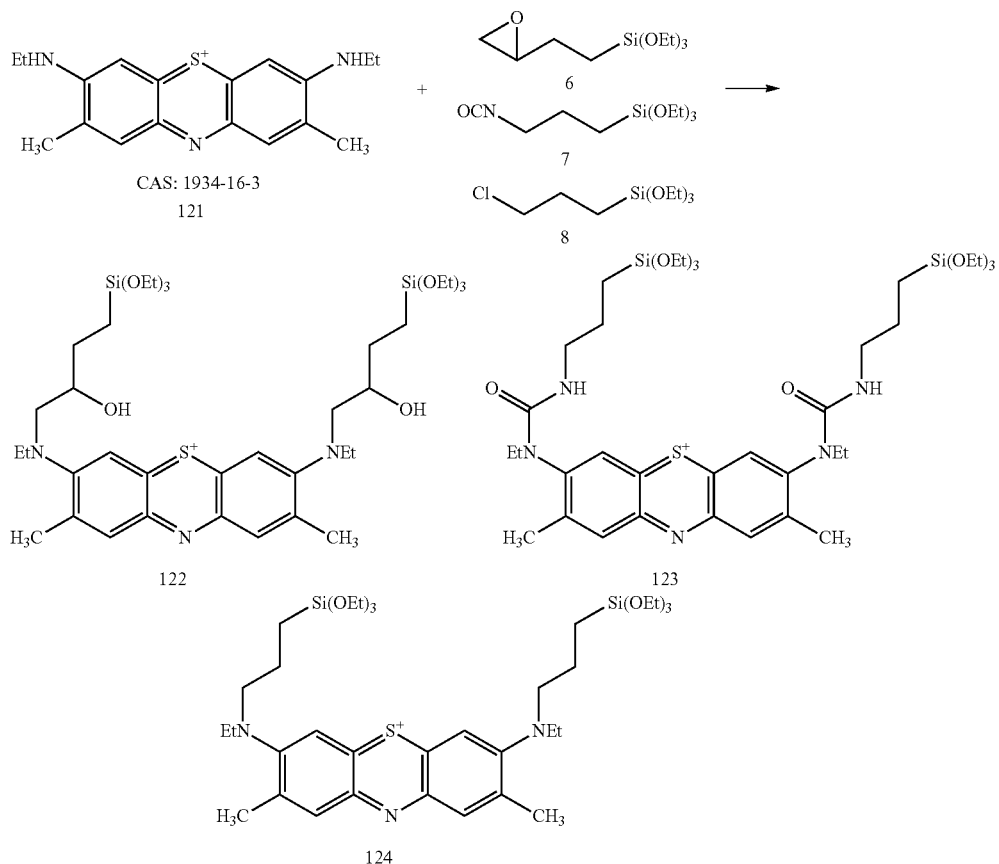

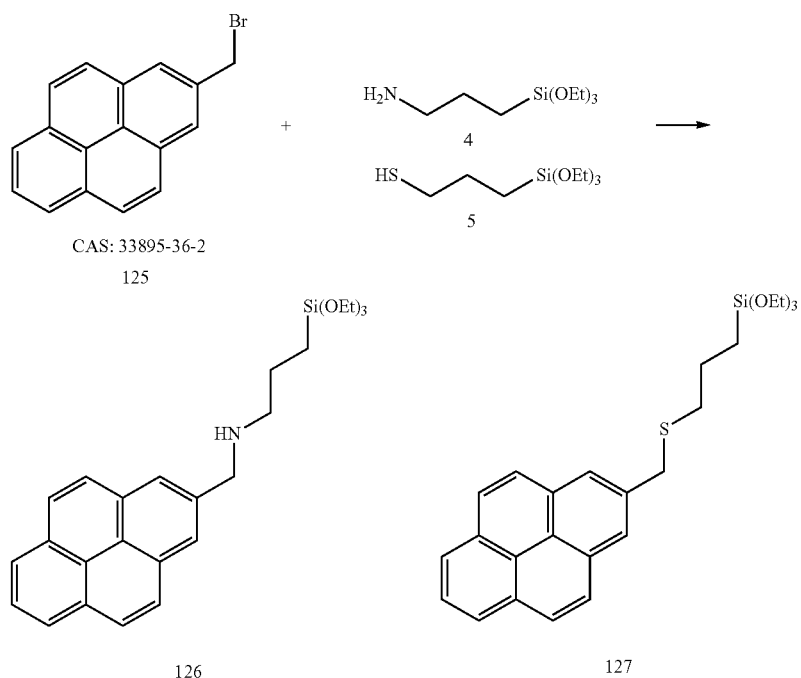

Reaction of substituted Pyrene Photocatalyst 128 with epoxysilyl ester 6 gives substituted Pyrene Photocatalyst Composition 129. Reaction of substituted Pyrene Photocatalyst 128 with isocyanatosilyl ester 7 gives substituted Pyrene Photocatalyst Composition 130. Reaction of substituted Pyrene Photocatalyst 128 with chlorosilyl ester 8 gives P substituted Pyrene hotocatalyst Composition 131.

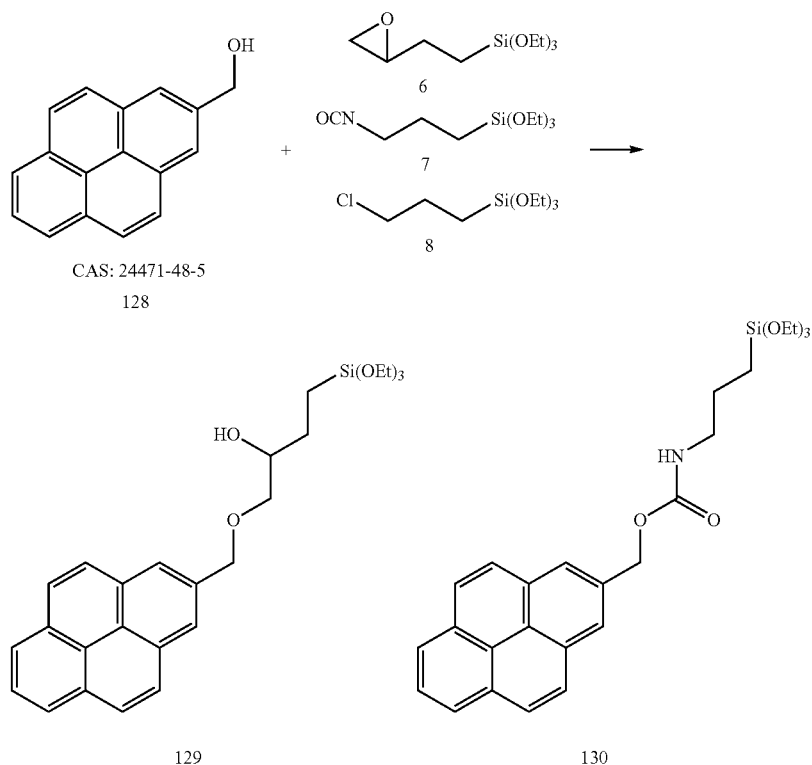

-continued

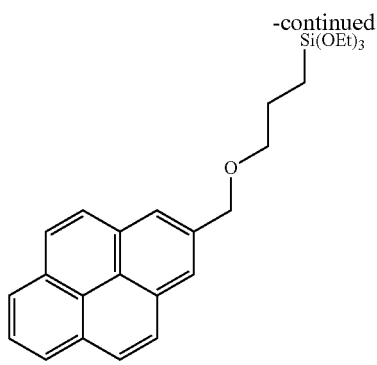
131

EXAMPLE 25

Quinoxaline CAS: 91-19-0; Φ~0.91

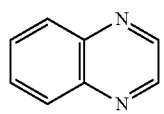

Reaction of substituted Quinoxaline Photocatalyst 132 with aminosilyl ester 4 gives substituted Quinoxaline Photocatalyst Composition 133. Reaction of substituted Quinoxaline photocatalyst 132 with mercaptosilyl ester 5 gives Photocatalyst Composition 134.

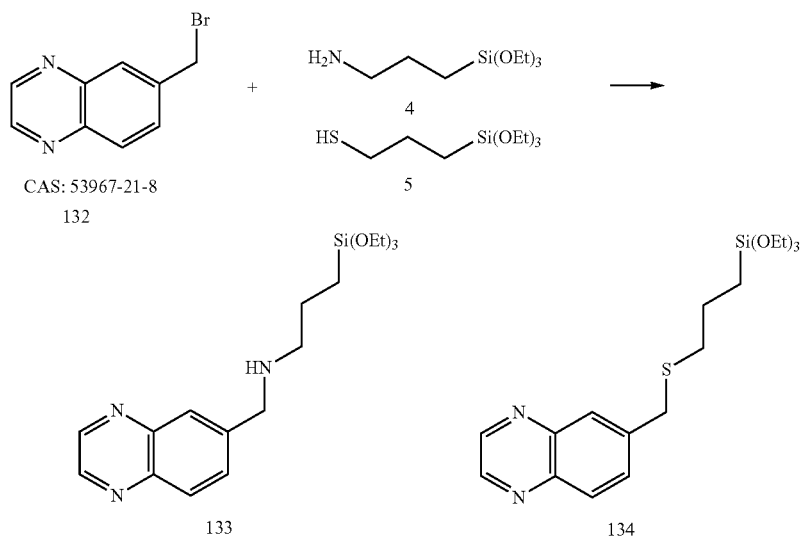

Reaction of substituted Quinoxaline photocatalyst 135 with epoxysilyl ester 6 gives substituted Quinoxaline Photocatalyst Composition 136. Reaction of substituted Quinoxaline photocatalyst 135 with isocyanatosilyl ester 7 gives substituted Quinoxaline Photocatalyst Composition 137. Reaction of substituted Quinoxaline photocatalyst 135 with chlorosilyl ester 8 gives substituted Quinoxaline Photocatalyst Composition 138.

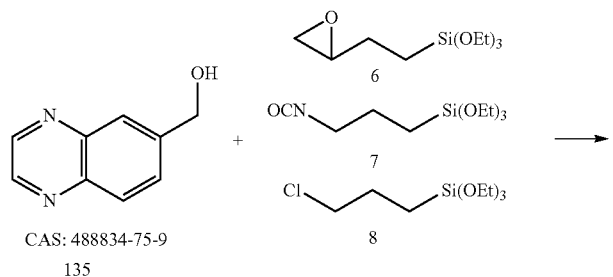

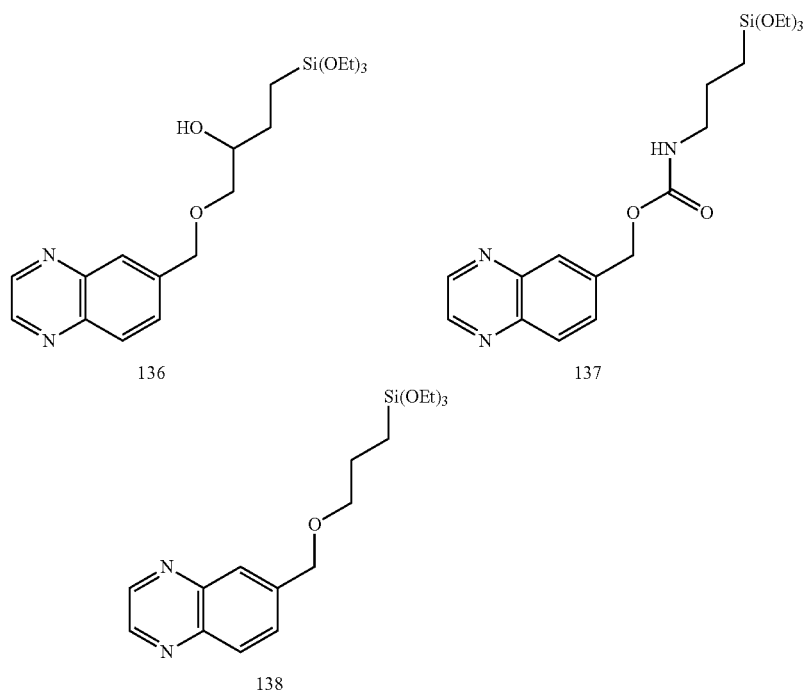

EXAMPLE 26

Retinol CAS: 68-26-8; Φ~0.7

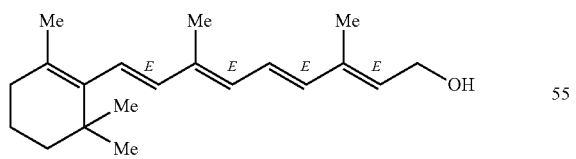

Reaction of substituted Retinol Photocatalyst 139 with epoxysilyl ester 6 gives substituted Retinol Photocatalyst Composition 140. Reaction of substituted Retinol photocatalyst 139 with isocyanatosilyl ester 7 gives substituted Retinol Photocatalyst Composition 141. Reaction of substituted Retinol photocatalyst 139 with chlorosilyl ester 8 gives substituted Retinol Photocatalyst Composition 142.

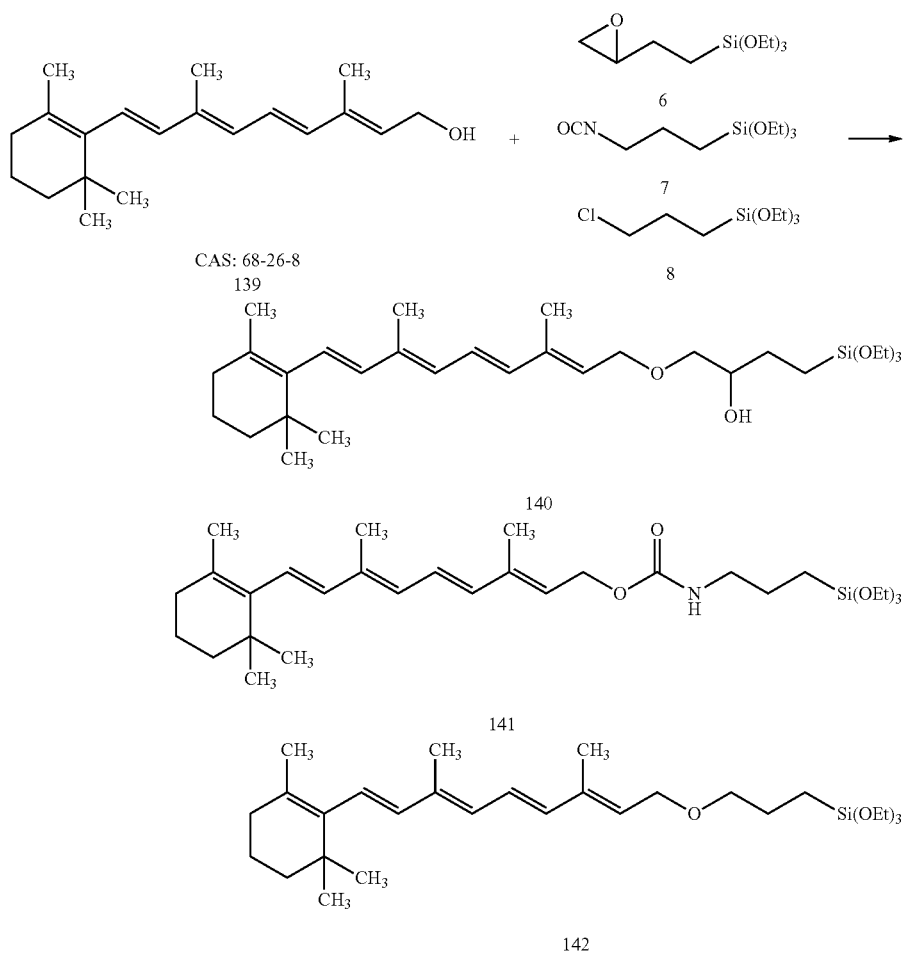

EXAMPLE 27

Riboflavin (Vitamin B2) CAS: 83-88-5; Φ~0.5

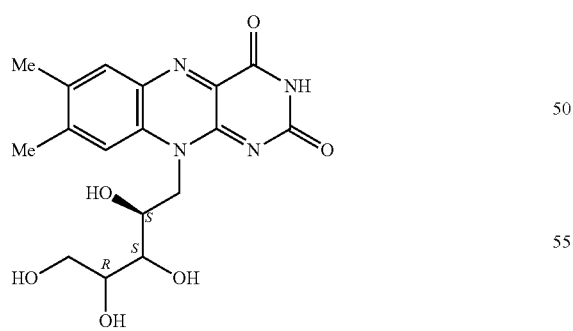

Reaction of substituted Riboflavin Photocatalyst 143 with epoxysilyl ester 6 gives substituted Riboflavin Photocatalyst Composition 144. Reaction of substituted Riboflavin photocatalyst 143 with isocyanatosilyl ester 7 gives substituted Riboflavin Photocatalyst Composition 145. Reaction of substituted Riboflavin photocatalyst 143 with chlorosilyl ester 8 gives substituted Riboflavin Photocatalyst Composition 146.

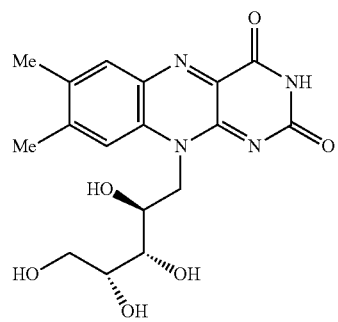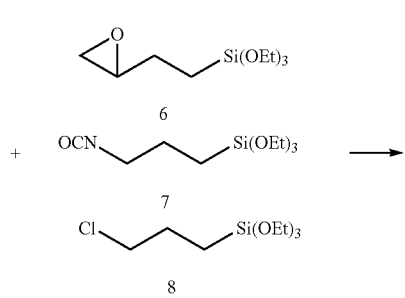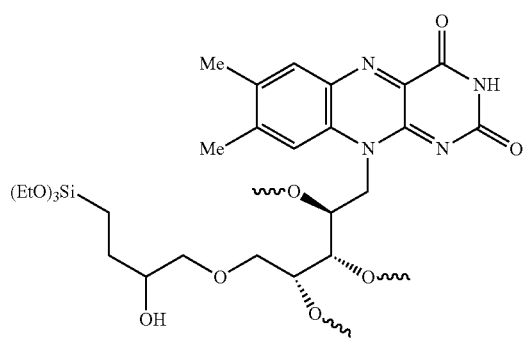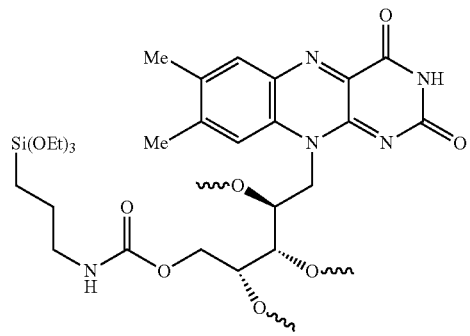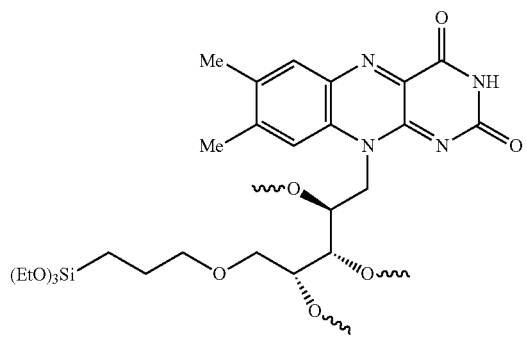

EXAMPLE 28

Rubrene CAS: 517-51-1; Φ~1

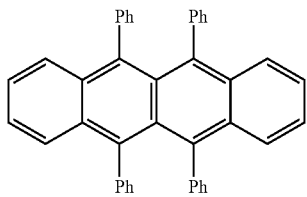 [SMILES: c1ccc(-c2c3ccccc3c(-c3ccccc3)c3c(-c4ccccc4)c4ccccc4c(-c4ccccc4)c23)cc1]
5

Reaction of substituted Rubrene Photocatalyst 147 with epoxysilyl ester 6 gives substituted Rubrene Photocatalyst Composition 148. Reaction of substituted Rubrene photocatalyst 147 with isocyanatosilyl ester 7 gives substituted Rubrene Photocatalyst Composition 149. Reaction of substituted Rubrene photocatalyst 147 with chlorosilyl ester 8 gives substituted Rubrene Photocatalyst Composition 150.

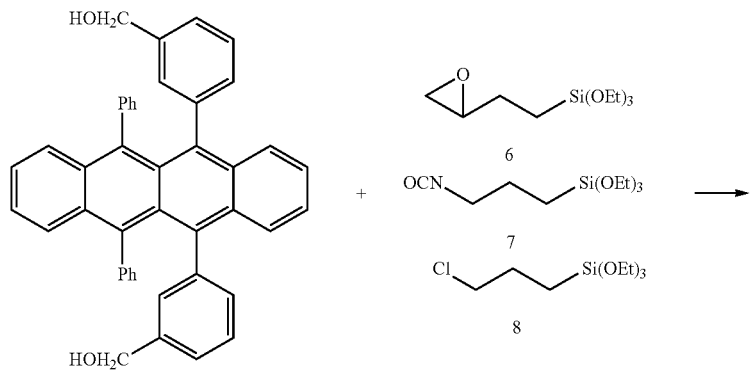

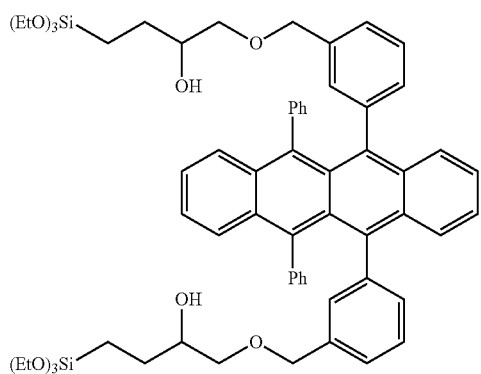

148

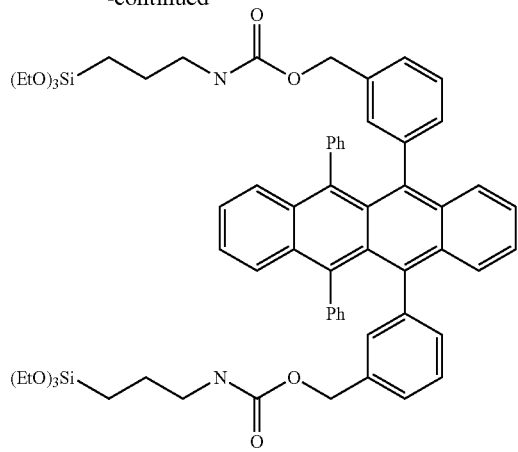
149
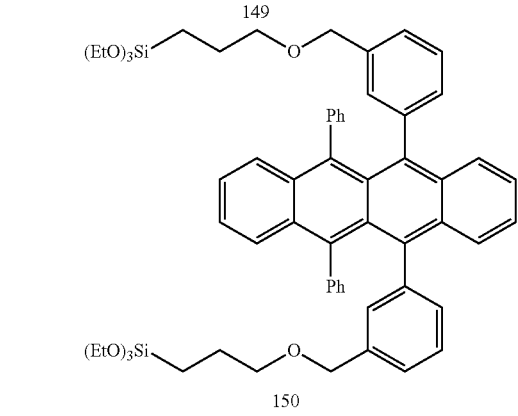
150
EXAMPLE 29
p-Terphenyl CAS: 92-94-4; Φ~0.9        40
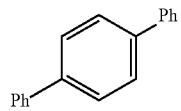
Reaction of substituted p-Terphenyl Photocatalyst 151 with aminosilyl ester 4 gives substituted p-Terphenyl Photocatalyst Composition 152. Reaction of substituted p-Terphenyl Photocatalyst 151 with mercaptosilyl ester 5 gives substituted p-Terphenyl Photocatalyst Composition 153.
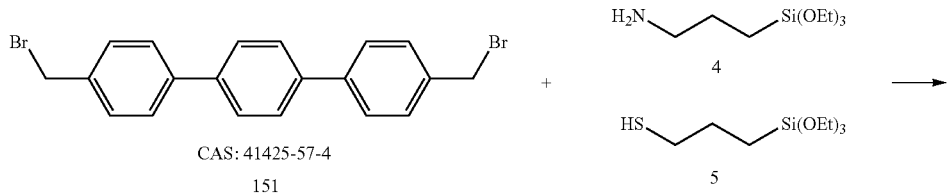

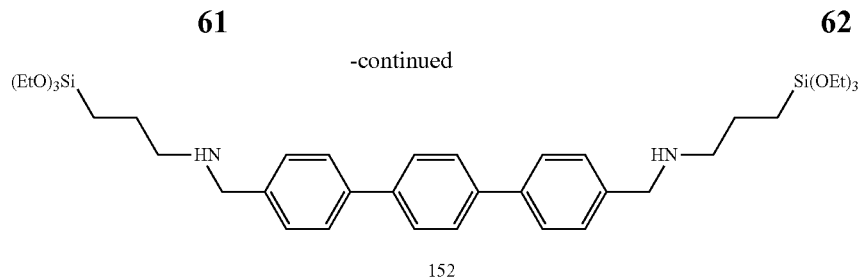
152
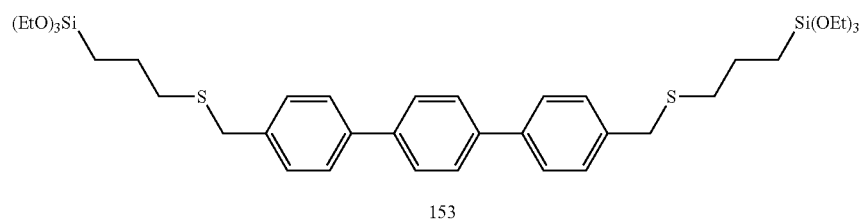
153
EXAMPLE 30
Bacteriochlorophyll A CAS: 17499-98-8; Φ~0.4
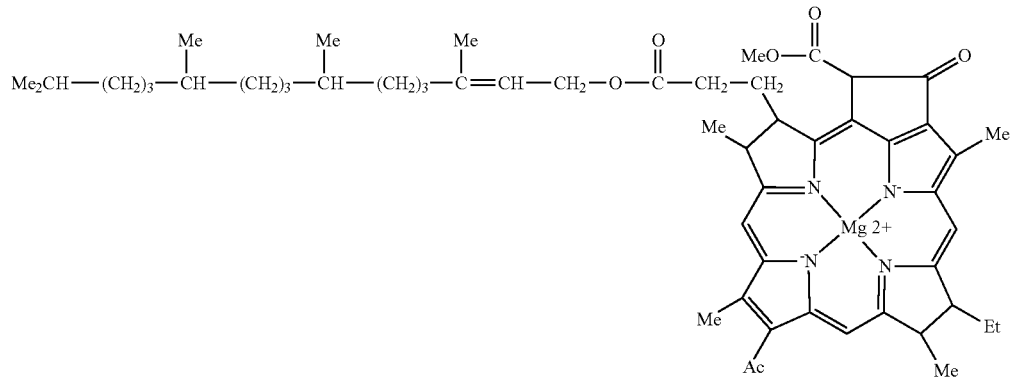
Reaction of substituted Bacteriochlorophyll A Photocatalyst 154 with aminosilyl ester 4 gives Bacteriochlorophyll A Photocatalyst Composition 155.
-continued
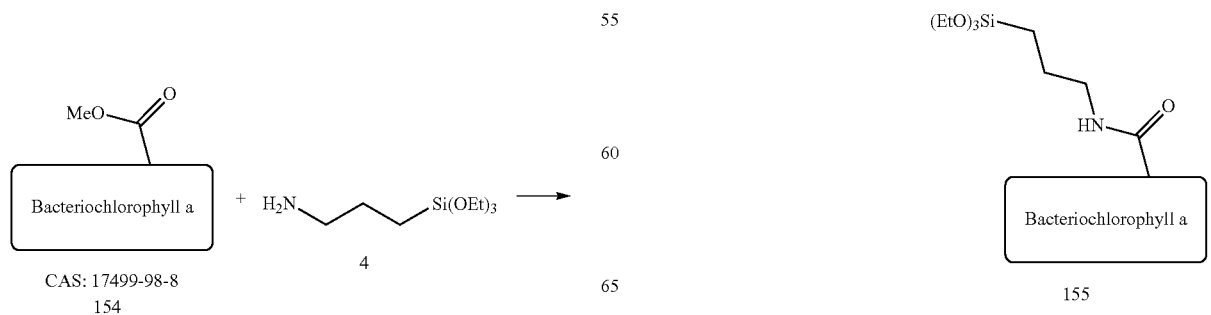

EXAMPLE 31
Bacteriochlorophyll B CAS: 53199-29-4; Φ~0.5
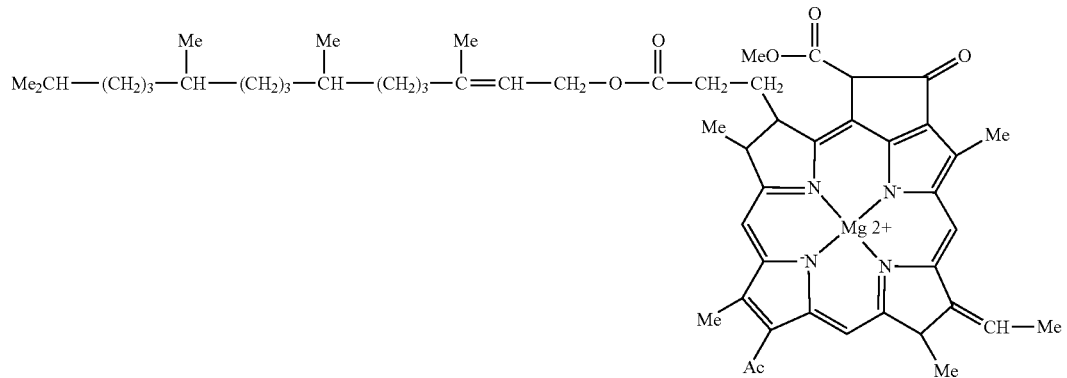
Reaction of substituted Bacteriochlorophyll B Photocatalyst 156 with aminosilyl ester 4 gives Bacteriochlorophyll B Photocatalyst Composition 157.
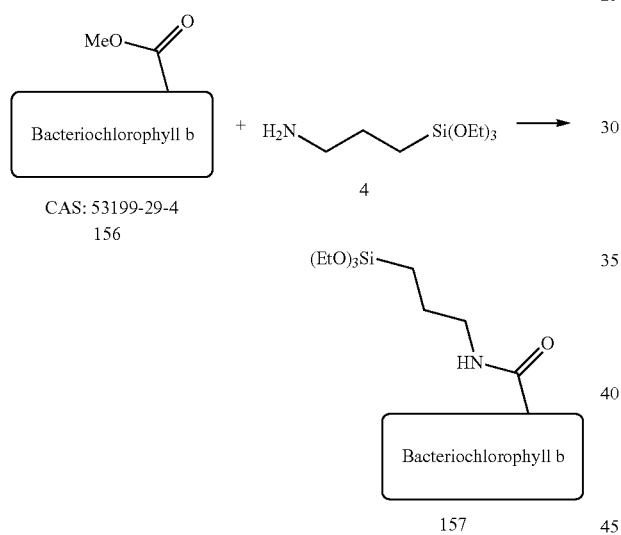
EXAMPLE 32
Chlorophyll A CAS: 479-61-8; Φ~0.5-0.7
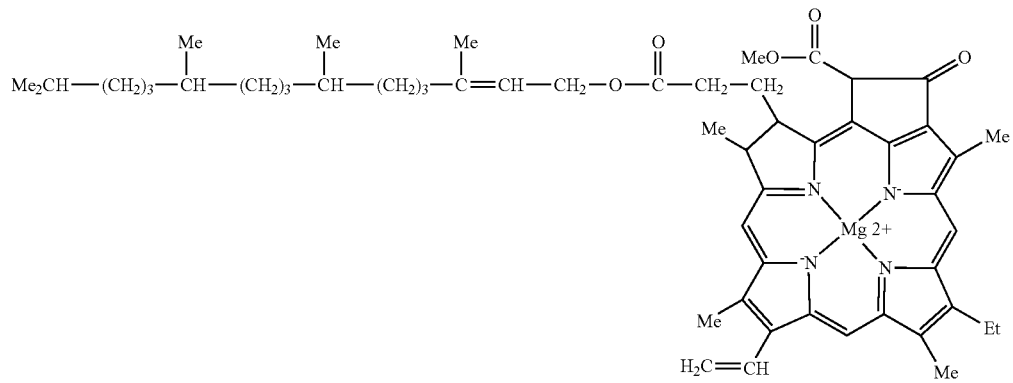

Reaction of substituted Chlorophyll A Photocatalyst 158 with aminosilyl ester 4 gives substituted Chlorophyll A Photocatalyst Composition 159.
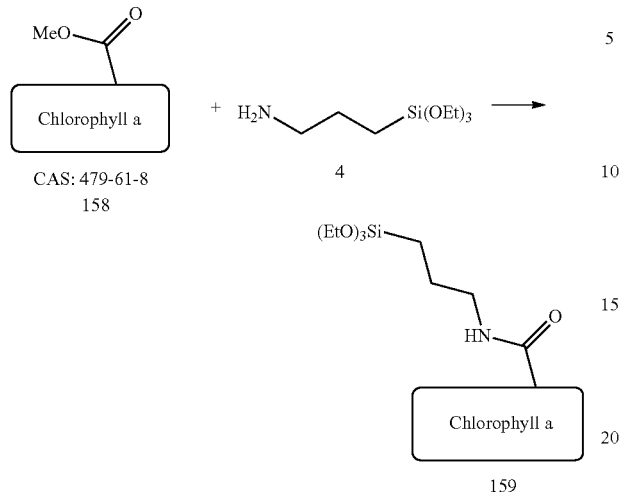
EXAMPLE 33
Chlorophyll B CAS: 519-62-0; Φ~0.7-0.8
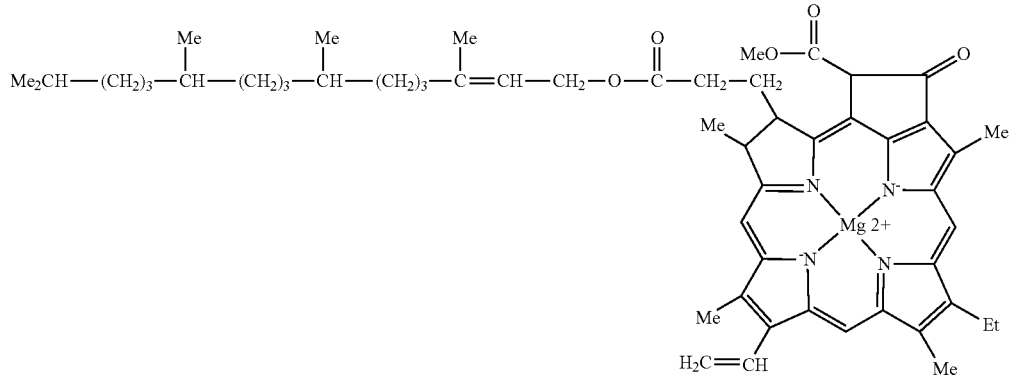
Reaction of substituted Chlorophyll B photocatalyst 160 with aminosilyl ester 4 gives substituted Chlorophyll B Photocatalyst Composition 161.
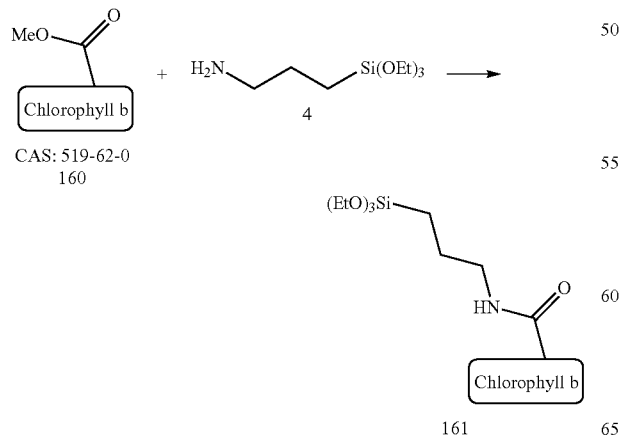

EXAMPLE 34
Pheophytin A CAS: 603-17-8; Φ~0.6-0.7
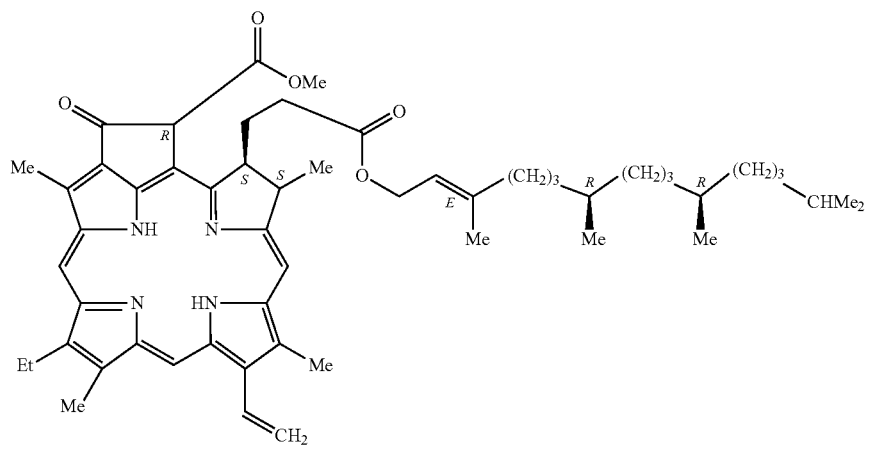
Reaction of substituted Pheophytin A Photocatalyst 162 with aminosilyl ester 4 gives substituted Pheophytin A Photocatalyst Composition 163.
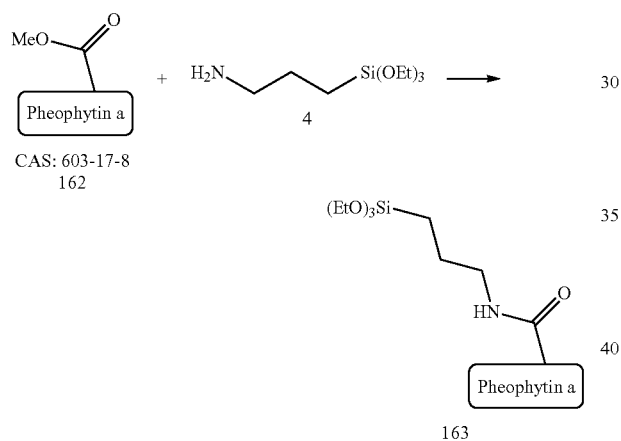
EXAMPLE 35
Pheophytin B CAS: 3147-18-0; Φ~0.7-0.8~
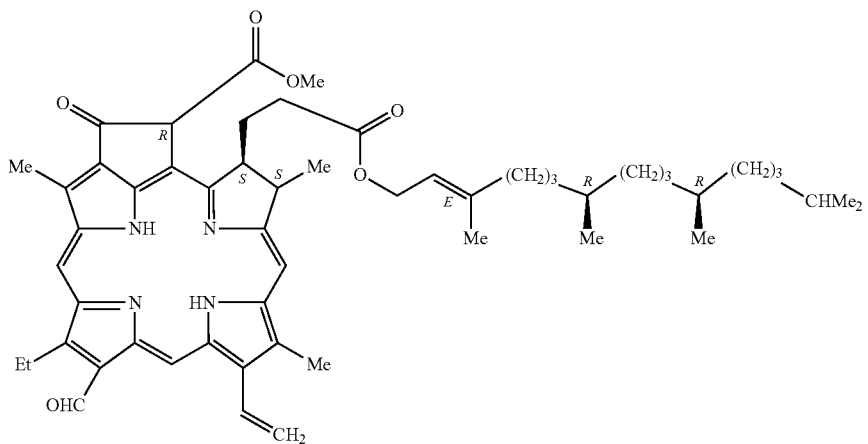

Reaction of substituted Pheophytin B Photocatalyst 164 with aminosilyl ester 4 gives substituted Pheophytin B Photocatalyst Composition 165.

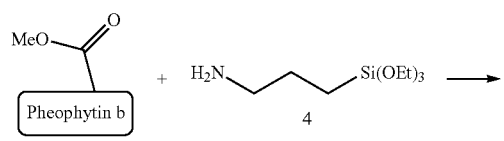

164
CAS: 3147-18-0

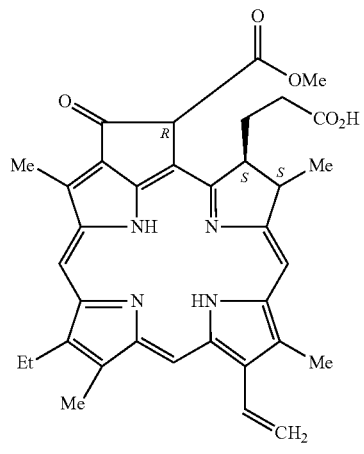

165

EXAMPLE 36

Pheophorbide A CAS: 15664-29-6; Φ~0.4-0.7

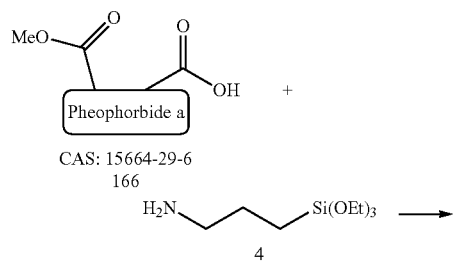

Reaction of substituted Pheophorbide A Photocatalyst 166 with aminosilyl ester 4 gives substituted Pheophorbide A Photocatalyst Composition 167.

166
CAS: 15664-29-6

-continued

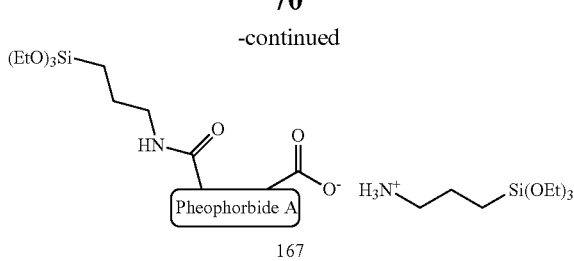

167

EXAMPLE 37

Protochlorophyllide CAS: 20369-67-9; Φ~0.7-0.8

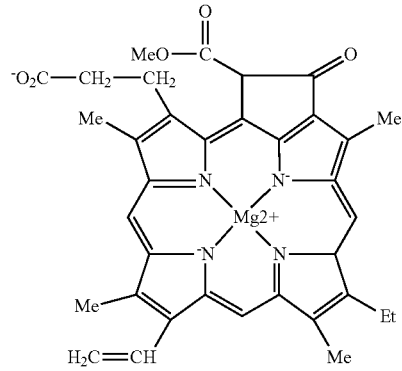

Reaction of substituted Protochlorophyllide photocatalyst 168 with aminosilyl ester 4 gives substituted Protochlorophyllide Photocatalyst Composition 169.

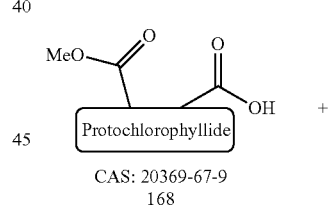

168
CAS: 20369-67-9

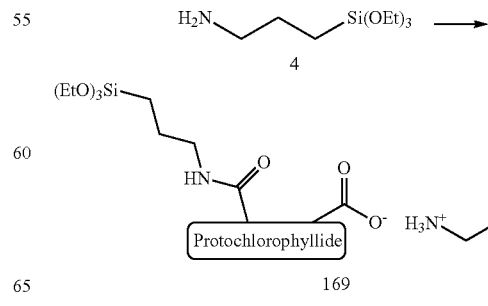

169

EXAMPLE 38

Protochlorophyll CAS: 14751-08-7; Φ~0.6-0.8

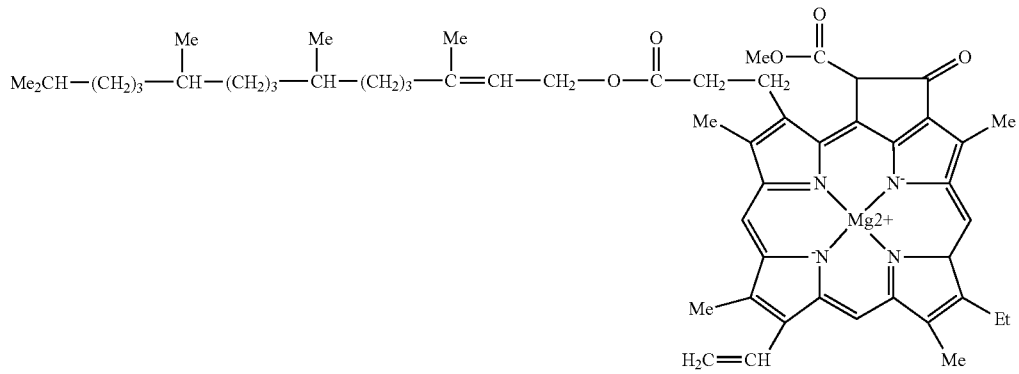

Reaction of substituted Protochlorophyll Photocatalyst 170 with aminosilyl ester 4 gives substituted Protochlorophyll Photocatalyst Composition 171.

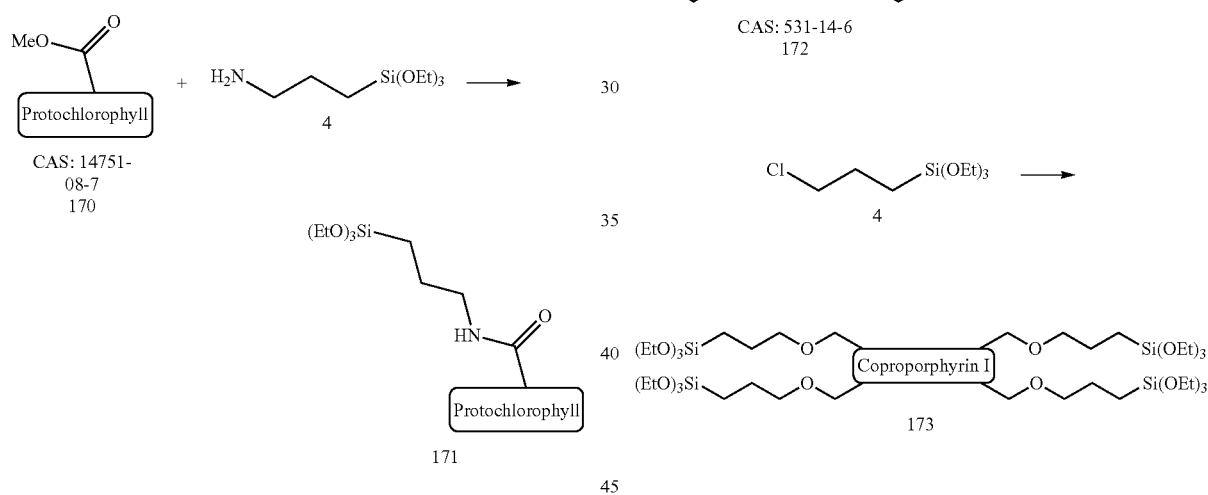

EXAMPLE 39

Coproporphyrin I CAS: 531-14-6; Φ~0.6

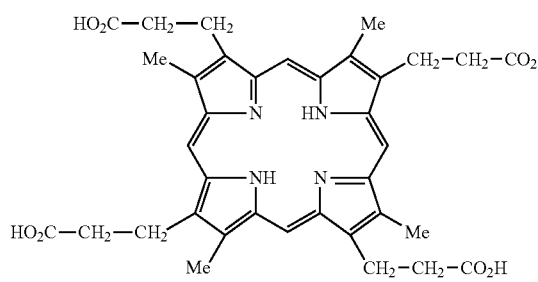

Reaction of substituted Coproporphyrin I photocatalyst 172 with aminosilyl ester 4 gives substituted Coproporphyrin I Photocatalyst Composition 173.

EXAMPLE 40

Fullerene-$C_{60}$ CAS: 99685-96-8; Φ~4

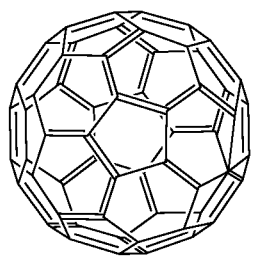

Reaction of substituted Fullerene-$C_{60}$ Photocatalyst 174 with aminosilyl ester 4 gives substituted Fullerene-$C_{60}$ Photocatalyst Composition 175.

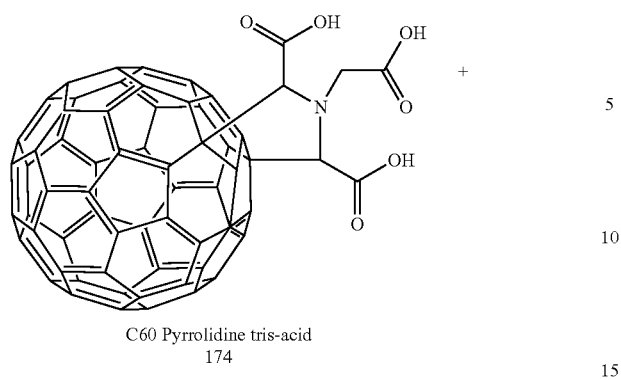
C60 Pyrrolidine tris-acid
174
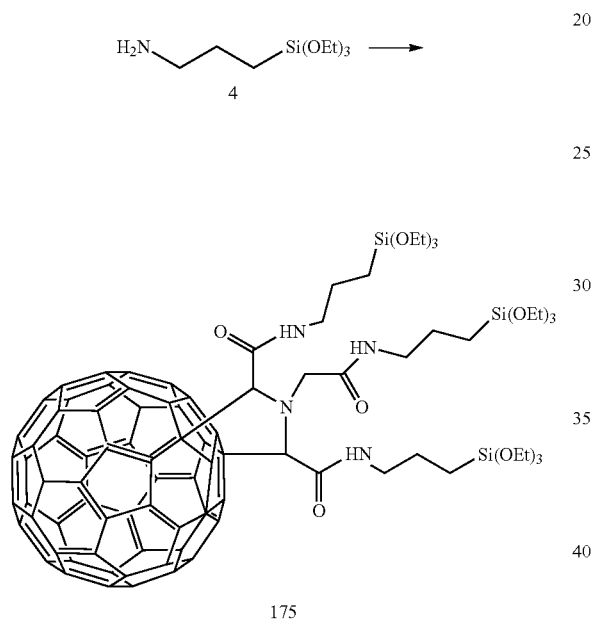
175
Reaction of substituted Fullerene-$C_{60}$ Photocatalyst 176 with chlorosilyl ester 8 gives substituted Fullerene-$C_{60}$ Photocatalyst Composition 177.
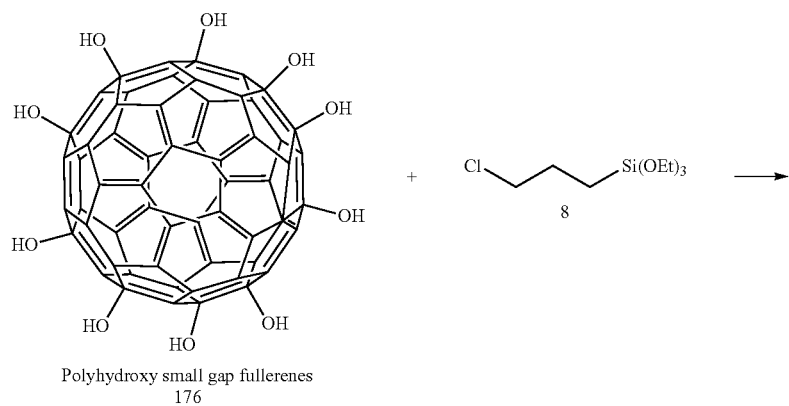
Polyhydroxy small gap fullerenes
176

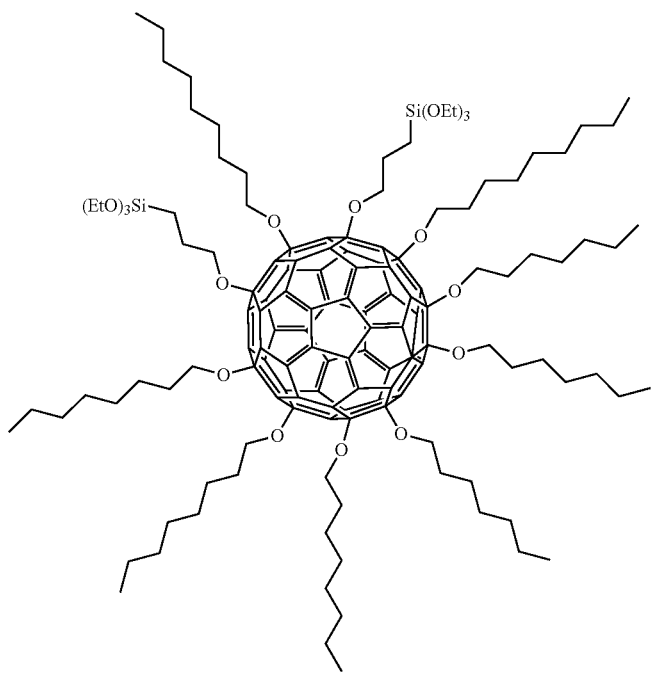
Reaction of substituted Fullerene-$C_{60}$ Photocatalyst 178 with aminosilyl ester 4 gives substituted Fullerene-$C_{60}$ Photocatalyst Composition 179.
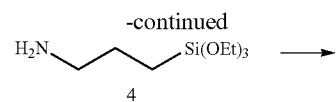
4
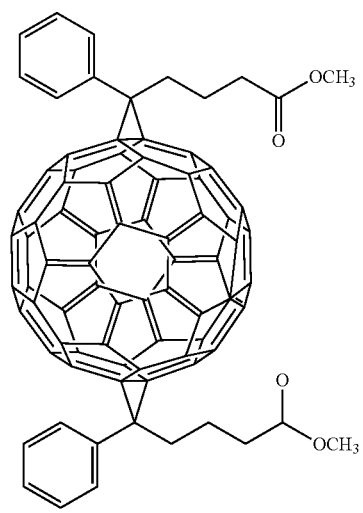
Diphenyl C62 bis(butyric acid methyl ester)
178
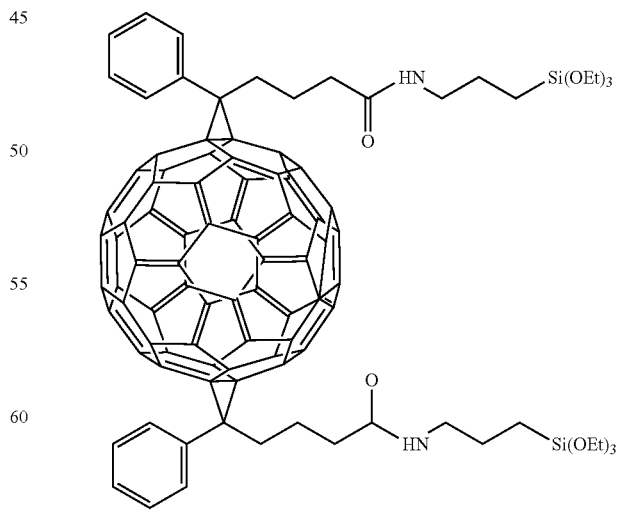
179

EXAMPLE 41

Tetraphenyl porphyrin CAS: 917-23-7; Φ~0.6-0.7

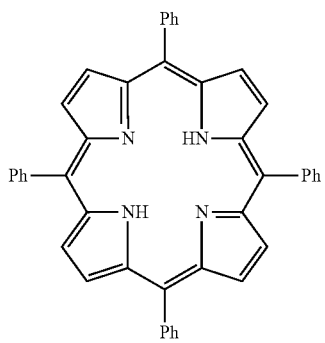 [SMILES: C1=Cc2nc1c(-c1ccccc1)c1ccc([nH]1)c(-c1ccccc1)c1nc(c(-c3ccccc3)c3ccc([nH]3)c2-c2ccccc2)C=C1]

Reaction of substituted Tetraphenyl porphyrin Photocatalyst 180 with chlorosilyl ester 8 gives substituted Tetraphenyl-porphyrin Photocatalyst Composition 181.

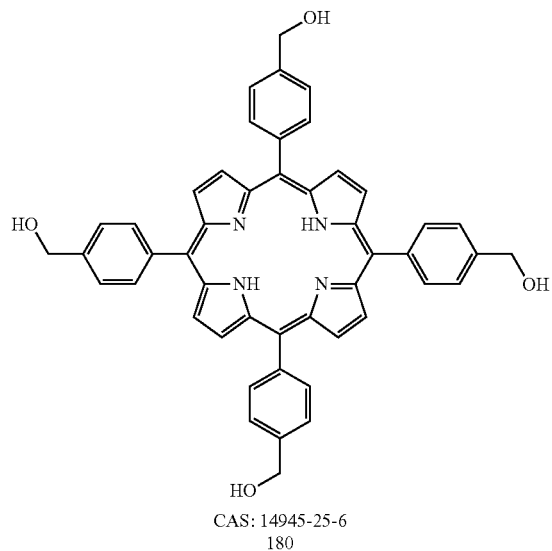

CAS: 14945-25-6
180

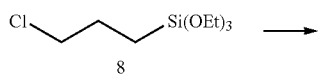

8

Reaction of Tetraphenyl Porphyrin photocatalyst 182 with aminosilyl ester 4 gives Tetraphenyl-porphyrin Photocatalyst Composition 183. Reaction of Tetraphenyl-porphyrin Photocatalyst 182 with mercaptosilyl ester 5 gives substituted Tetraphenyl Porphyrin Photocatalyst Composition 184.

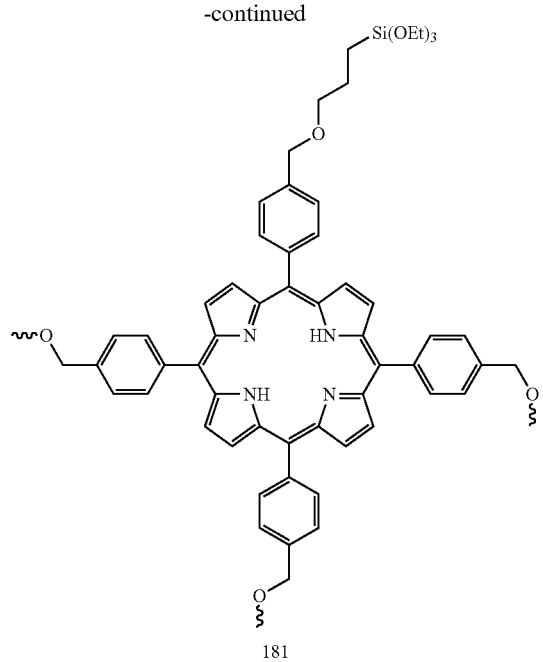

181

CAS: 158808-43-6
182

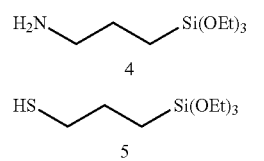

4

5

-continued
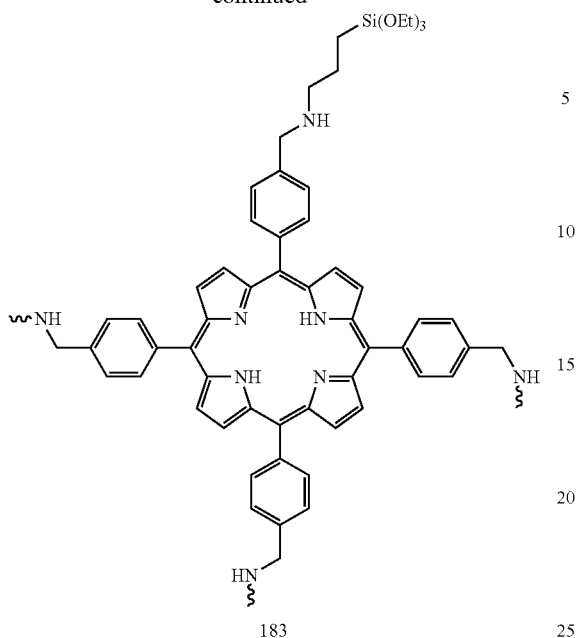
183
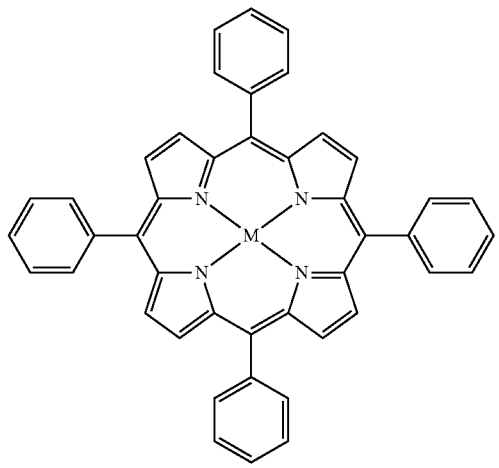
184
EXAMPLE 42
Metallo-Tetraphenyl porphyrin; Φ~6-0-9
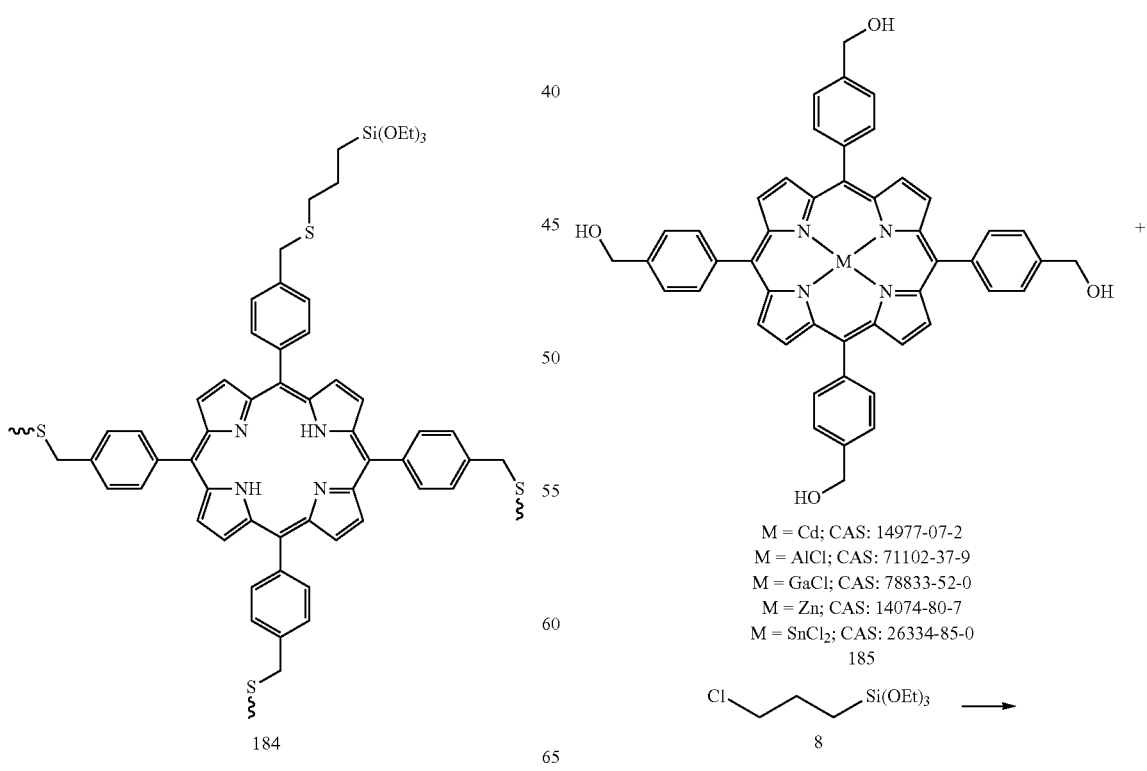
M = Cd; CAS: 14977-07-2
M = AlCl; CAS: 71102-37-9
M = GaCl; CAS: 78833-52-0
M = Zn; CAS: 14074-80-7
M = SnCl$_2$; CAS: 26334-85-0
Reaction of substituted Metallo-Tetraphenyl Porphyrin photocatalyst 185 with chlorosilyl ester 8 gives substituted Metallo-Tetraphenyl Porphyrin Photocatalyst Composition 186.
M = Cd; CAS: 14977-07-2
M = AlCl; CAS: 71102-37-9
M = GaCl; CAS: 78833-52-0
M = Zn; CAS: 14074-80-7
M = SnCl$_2$; CAS: 26334-85-0
185
8

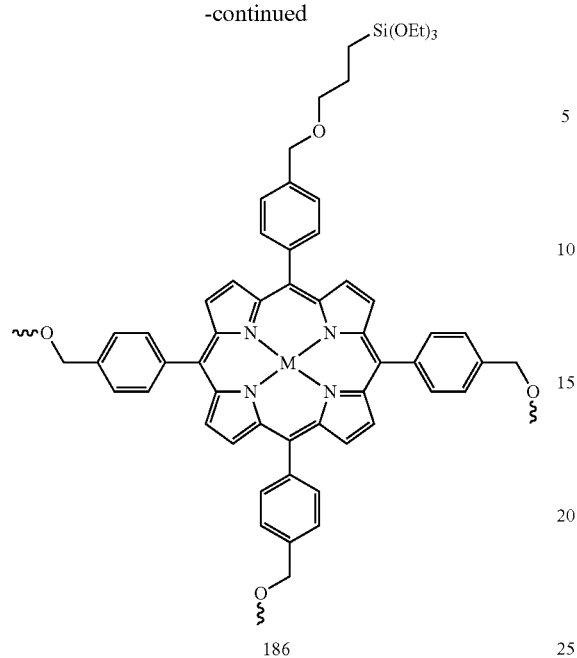

186

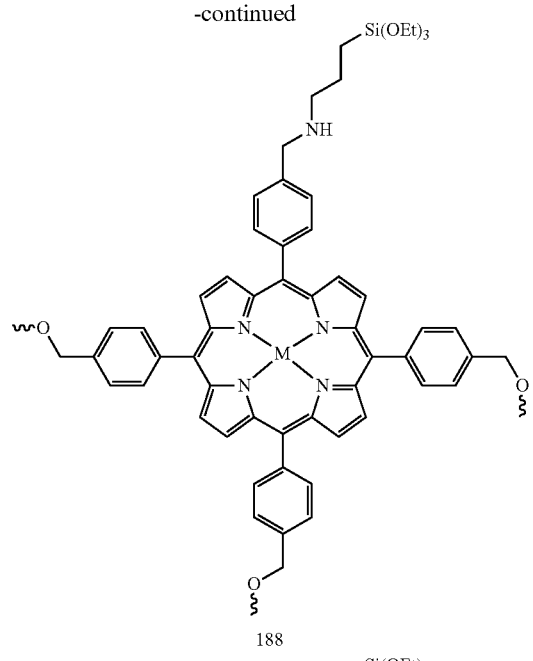

188

Reaction of substituted Metallo-Tetraphenyl Porphyrin Photocatalyst 187 with aminosilyl ester 4 gives substituted Metallo-Tetraphenyl Porphyrin Photocatalyst Composition 188. Reaction of substituted Metallo-Tetraphenyl Porphyrin Photocatalyst 187 with mercaptosilyl ester 5 gives substituted Metallo-Tetraphenyl Porphyrin Photocatalyst Composition 189.

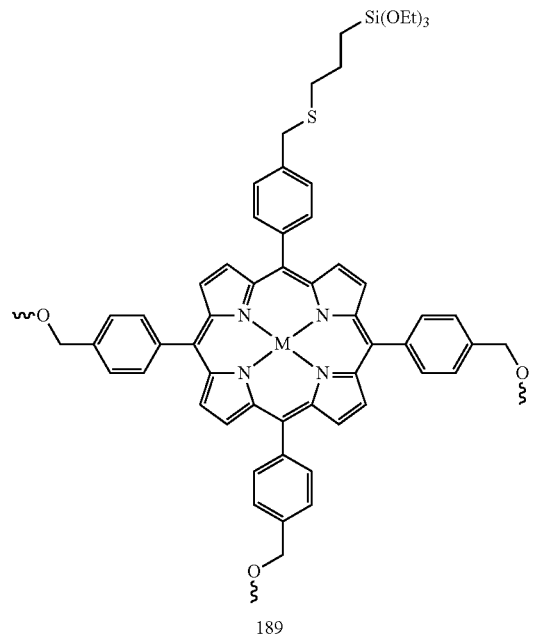

189

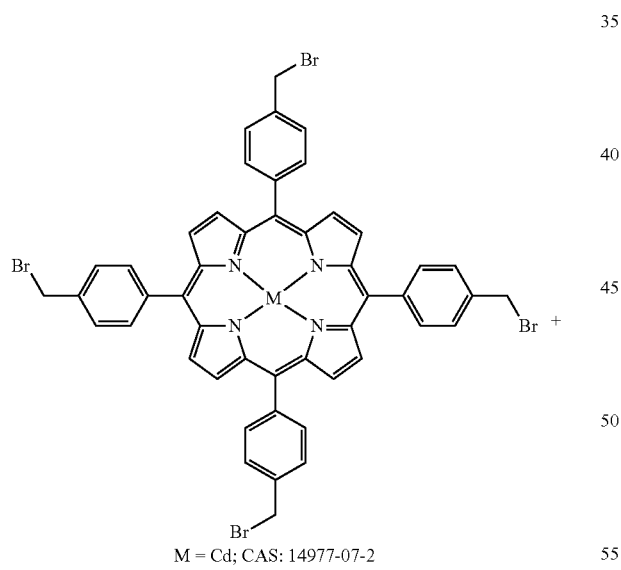

M = Cd; CAS: 14977-07-2
M = AlCl; CAS: 71102-37-9
M = GaCl; CAS: 78833-52-0
M = Zn; CAS: 14074-80-7
M = SnCl$_2$; CAS: 26334-85-0

187

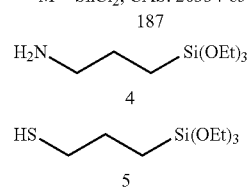

EXAMPLE 43

Methylene Blue CAS: 61-73-4; Φ~0.5

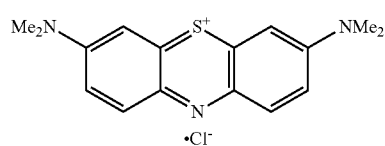 [SMILES: CN(C)c1ccc2nc3ccc(N(C)C)cc3[s+]c2c1 ; [Cl-]]

Reaction of substituted Methylene Blue Photocatalyst 195 with bromosilyl ester 196 gives substituted Methylene Blue Photocatalyst Composition 197.

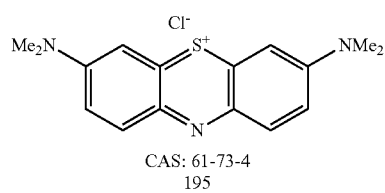

CAS: 61-73-4
195

+

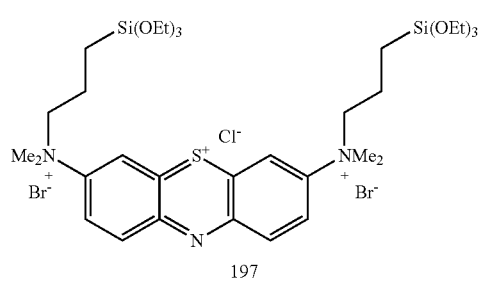

197

Applicant has disposed their Photocatalyst Composition III onto various substrates using conventional water-borne coating equipment and methods. The following Example 44 is presented to further illustrate to persons skilled in the art how to make and use the invention. Example 44 is not intended as a limitation, however, upon the scope of Applicant's invention.

EXAMPLE 44

Tetrasulfonylchloride-substituted Aluminum Phthalocyanine Photocatalyst 190 (0.2 gram) was dissolved in ethanol (200 proof; 10 mL). Sonication was used. Triethylamine (0.08 g) was added to the photocatalyst 190 solution. Aminopropyl triethoxysilane, Compound 4, (0.14 g) was added to the photocatalyst solution to form Photocatalyst Composition 191. The Photocatalyst Composition 191 was stirred at room temperature in the dark for 3 hrs.

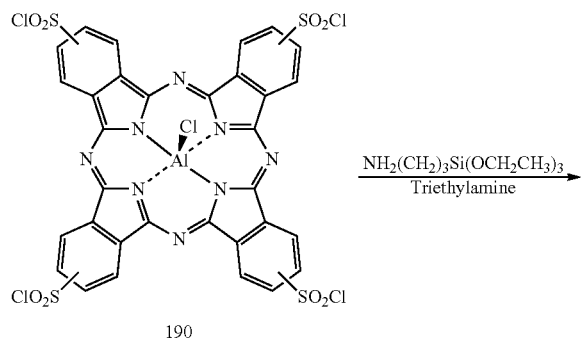

190

R = NH(CH$_2$)$_3$Si(OCH$_2$CH$_3$)$_3$
191

About 100 mL of 5% v/v ammonium hydroxide solution was prepared using concentrated ammonium hydroxide by mixing about 95 mL of water and 5 mL of concentrated ammonium hydroxide solution. In various embodiments, Applicant prepared a coating composition comprising between about 5% to about 25% v/v of the above-described ethanol/triethylamine solution of Photocatalyst Composition 191 in ammonium hydroxide. Table 1 recites typical formulations.

TABLE 1

| Batch No. | Dye Stock (mL) | EtOH (mL) | 5% NH$_4$OH (mL) | EtOH content |
|---|---|---|---|---|
| 1 | 0.5 | 0 | 9.5 | 5% |
| 2 | 0.5 | 2 | 7.5 | 25% |
| 3 | 1 | 0 | 9 | 10% |
| 4 | 1 | 1.5 | 7.5 | 25% |

In embodiments wherein Applicant's coating composition further comprises one or more singlet oxygen traps, those singlet oxygen trap compounds are added to the above-described ethanol/triethylamine/ammonium hydroxide mixture of Photocatalyst Composition 191. In certain embodiments described hereinbelow, Applicant's singlet oxygen scavengers comprise substituted pyridones.

EXAMPLE 45

Applicant's coating composition can be applied to various films and fabrics, including for example and without limitation polypropylene fabric, cotton fabric, polyester fabric, nylon fabric, and the like. In this Example 43 Spunbond polypropylene sold in commerce by Kappler under the tradename Provent 10000 was employed as a coating substrate. The coating substrate was first pre-treated with a polyurethane pre-coating. For example and without limitation, WitCoBond UCX-281F sold in commerce by Chemtura was applied to the Provent 10000 surface in a 5% to about 10% w/w aqueous mixture. The polyurethane pre-coating was applied by either rolling or spraying. After application of the polyurethane pre-coating, the pre-coated Provent 10000 was allowed to dry at ambient condition overnight.

The coating composition of Example 44 was then applied to the polyurethane precoated Provent 10000 by either rolling or spraying. The treated surface was dried at 100° C. for 1 to-2 minutes.

Applicant has discovered that the treated fabric of Example 45 is self-decontaminating with respect to various odors. By "self-decontaminating with respect to odor," Applicant means that exposing the treated fabric of Example 45 to an odorant followed by exposure of that treated/exposed fabric to either sunlight or indoor lighting, effectively eliminates the odor from the treated/exposed/illuminated fabric with respect to a control/untreated fabric. The untreated/odorant exposed/illuminated fabric retains the odor of the odorant. In marked contrast, however, when using the treated fabric of Example 45, the treated/odorant exposed/illuminated fabric does not retain the odor of the odorant.

EXAMPLE 46

For example, the treated fabric of Example 45 self-decontaminates with respect to cigarette smoke odors. T-shirts were treated with the coating composition, using method of, Example 44 to give the treated fabric of Example 45 in the form of a T-shirt. A treated T-shirt was placed on a first hanger and suspended within a first polyethylene bag. An uncoated T-shirt control was placed on a second hanger and suspended in a second polyethylene bag.

Cigarette smoke was introduced into both the first bag and the second bag, thereby exposing both the treated T-shirt and the control T-shirt to cigarette smoke. The first bag and the second bag were then sealed. The treated T-shirt and the control T-shirt were kept in the respective sealed polyethylene bags for one hour.

Thereafter, the treated T-shirt and the untreated T-shirt were removed from the respective bags, and were exposed to indoor fluorescent lighting for two hours. In accord with ASTM E679-91 ("Standard Practice for Determination of Odor and Taste Thresholds by a Forced-Choice Ascending Concentration Series Method of Limits"), a panel of four odor assessors independently sniffed both the treated T-shirt and the untreated T-shirt. Each of the odor assessors reported that the untreated T-shirt retained an odor of cigarette smoke, but the treated T-shirt retained no odor of cigarette smoke.

EXAMPLE 47

In addition, the treated fabric of Example 45 self-decontaminates with respect to mercaptans. T-shirts were treated with the coating composition, using method of, Example 44 to give the a treated fabric of Example 45 in the form of a T-shirt. A treated T-shirt was placed on a first hanger and suspended within a first polyethylene bag. An uncoated T-shirt control was placed on a second hanger and suspended in a second polyethylene bag.

Propane gas containing an ethyl mercaptan odorant was introduced into both the first bag and the second bag, thereby exposing both the treated T-shirt and the control T-shirt to the ethyl mercaptan odorant. The first bag and the second bag were then sealed. The treated T-shirt and the control T-shirt were kept in the respective sealed polyethylene bags for one hour. As those skilled in the art will appreciate, ethyl mercaptan is added to propane gas at a loading of 3.3 milligrams per 100 grams of liquefied propane.

Thereafter, the treated T-shirt and the untreated T-shirt were removed from the respective bags, and were exposed to indoor fluorescent lighting for two hours. In accord with ASTM E679-91 ("Standard Practice for Determination of Odor and Taste Thresholds by a Forced-Choice Ascending Concentration Series Method of Limits"), a panel of four odor assessors independently sniffed both the treated T-shirt and the untreated T-shirt. Each of the odor assessors reported that the untreated T-shirt retained an odor of ethyl mercaptan, but the treated T-shirt retained no odor of ethyl mercaptan.

EXAMPLE 48

As those skilled in the art will appreciate, many odors are produced by various biological agents, such as for example bacteria. Bioburden testing was performed by Nelson Laboratories in Salt Lake City, Utah. The levels of Aerobic, Anaerobic, and Spore-forming bacteria on the surface of the treated fabric of Example 45 and an untreated test fabric comprising Provent 10000 were determined. Both the control fabric and the test fabric were subjected to only normal fluorescent light illumination.

TABLE 2

|  | AEROBIC | ANAEROBIC | SPORE |
|---|---|---|---|
| CONTROL FABRIC (CFU)* | 189 | 256 | 451 |
| TEST FABRIC (CFU)* | 79 | 30 | 151 |

*CFU = Colony Forming Units

Table 2 summarizes the bioburden testing results. Table 2 recites data showing that Applicant's test fabric comprises a treated fabric bacterial level of 79 CFU, 30 CFU, and 151 CFU, for aerobic, anaerobic, and spore forming bacteria, respectively. Table 2 further recites data showing that Applicant's control fabric comprises an untreated fabric bacteria level of 189 CFU, 256 CFU, and 451 CFU, for aerobic, anaerobic, and spore forming bacteria, respectively, wherein the treated fabric bacteria level is less than the comparable untreated fabric bacteria level.

EXAMPLE 49

The American Association of Textile Chemists and Colorists ("AATCC") have promulgated test method AATCC 100 which is directed to microbiological testing. AATCC 100 provides a quantitative procedure for the evaluation of the degree of antibacterial activity.

A test microorganism is grown in liquid culture. The test protocol used to evaluate Applicant's coating described herein above utilized *Klebsiella pneumoniae* ("*K. pneumoniae*"). *K. pneumoniae* is a gram negative, rod-shaped, bacterium comprising a thick lipopolysaccharide superficial membrane layer. *K. pneumoniae* is known to be resistant to many biocides and antibiotics.

The concentration of the *K. pneumoniae* was standardized. The microbial culture was diluted in a sterile nutritive solution.

Control fabric swatches comprised untreated Provent 10000 fabric. Test fabric swatches comprises the treated fabric of Example 45. Control and test fabric swatches were inoculated with microorganisms. According to AATCC 100 antimicrobial test procedure, 1.0 mL of test organism suspension at approximately 1,000,000 CFU/mL is inoculated to test sample.

The inoculation was performed such that the microbial suspension contacts only the fabric swatches. Bacteria levels on both control and test fabrics were determined at "time zero" by elution in a large volume of neutralizing broth, followed by dilution and plating.

Additional inoculated control and test fabrics were irradiated with a 1000 Watt, 3600-3700 Lux halogen lamps for two hours. After incubation and irradiation, organisms were extracted from the test fabric and the control fabric into a neutralizer media which is diluted and plated accordingly. The plates were allowed to incubate at 37±1C.° for 24 hours. A standard CFU (colony forming units) count method was performed. Reduction of microorganisms relative to initial concentrations and the control fabric were then calculated. Table 3 summarizes the levels of *K. pneumoniae* found on the test fabric and the control fabric

TABLE 3

| Sample | Avg CFU/mL | Log |
|---|---|---|
| Test Fabric | 0 | 1 |
| Control Fabric | >4 × 10$^6$ | 6.60 |
| Log Reduction | — | 5.60 |

EXAMPLE 50

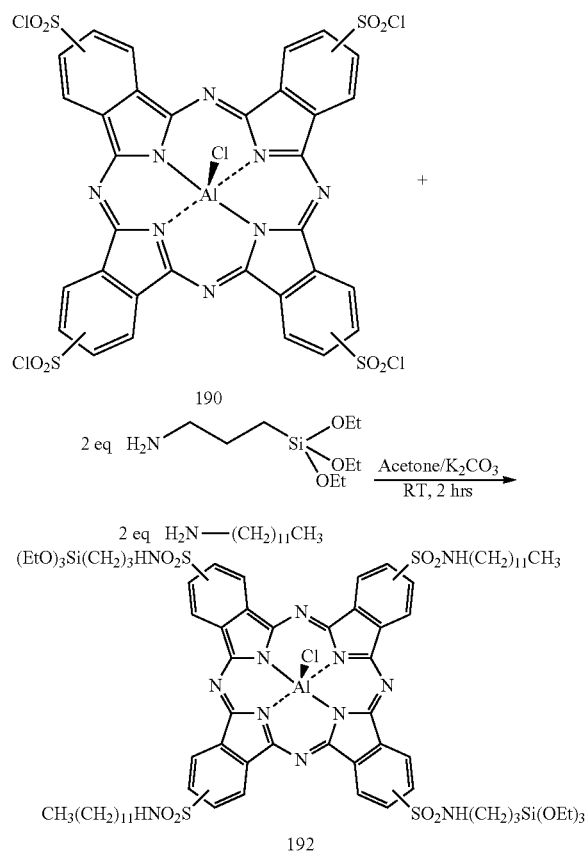

190

192

Photocatalyst Composition 192 Preparation

Aluminum phthalocyanine tetrasulfonylchloride 190 (2 g) was dissolved in 10 mL acetone. Sonication was employed to promote dissolution of the dye. Potassium carbonate (anhydrous; >4 eq, ~1.3 g) was added to the dye solution. The resulting mixture was stirred at room temperature. Aminopropyltriethoxysilane (Silquest A-1100, Momentive Performance materials, Inc., North Greenbush, N.Y.); 2 eq, 0.91 g) and n-dodecylamine (2 eq, 0.76 g) were mixed with 5 mL of ethanol (200 proof) yielding a clear solution. This clear mixture was slowly added dropwise to the Aluminum phthalocyanine tetrasulfonylchloride solution within 10 min period to prepare Photocatalyst Composition 192. Additional ethanol (5 mL) was added to the Photocatalyst Composition 192 solution. The resulting Photocatalyst Composition 192 solution was allowed to stir vigorously at room temperature for at least 2 hrs prior used in a coating formulation.

Coating Formulation:

Table 4 summarizes Applicant's coating formulations using the Photocatalyst Composition 192.

TABLE 4

| Batch No. | 192 Stock (mL) | 5% NH$_4$OH (mL) | Water (mL) | Q2-5211 * (mL) | 5% W281F (mL) | VOC ** content |
|---|---|---|---|---|---|---|
| 1 | 2 | 4 | 3 | 1 | 1 | ~20% |
| 2 | 2 | 4 | 3 | 0.1 | 1 | ~20% |

* Q2-5211 = a silicone based superwetting agent from Dow Corning Corp., Midland, MI.
** VOC = volatile organic compound(s) = acetone and ethanol Preparation of Treated Fabric:

The method of Example 45 was utilized. The treated fabric was dried at 75° C. (oven set @ 80° C.) for 13-16 min.

Antimicrobial Testing:

The treated fabric of this Example 50 was evaluated using the AATCC 100 test procedure described hereinabove in Example 49. Table 5 summarizes the AATCC test results using *K. pneumoniae* and the fabric treated with Batch No. 1 of the coating formulation comprising Photocatalyst Composition 192, as described immediately hereinabove.

TABLE 5

| Sample | Avg CFU/mL | Log |
|---|---|---|
| Dyed Fabric (light) | 0 | 1 |
| Dyed Fabric (dark) | 0 | 1 |
| Control No Dye (light) | 2.015 × 10$^4$ | 4.304 |
| Control No Dye (dark) | 3.815 × 10$^4$ | 4.581 |
| Log Reduction (light) | — | 3.304 |
| Log Reduction (dark) | — | 3.581 |

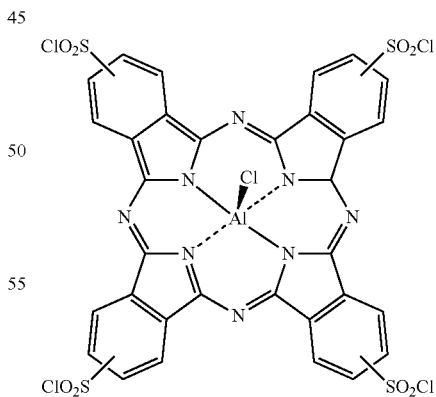

190

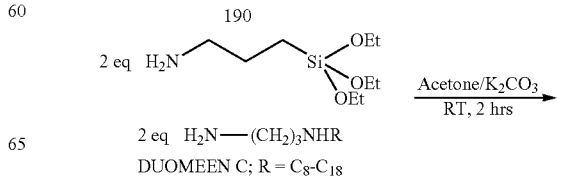

2 eq H$_2$N—(CH$_2$)$_3$NHR

DUOMEEN C; R = C$_8$-C$_{18}$

-continued

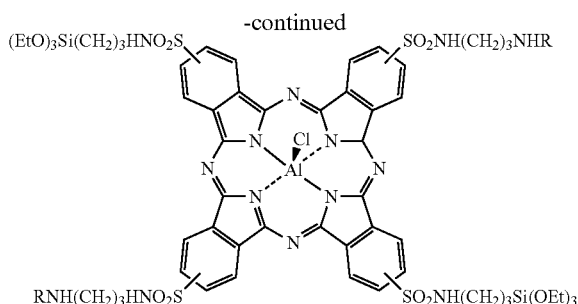

193

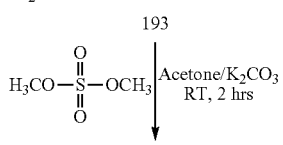

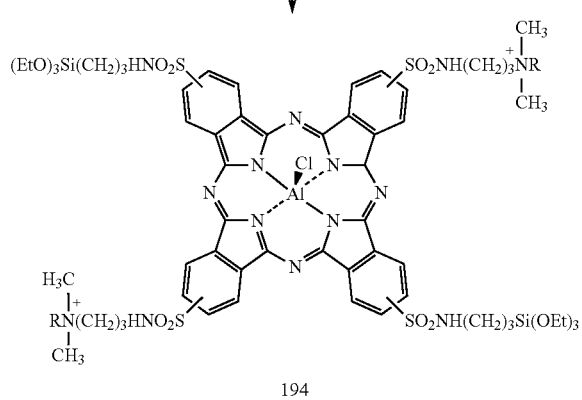

194

Photocatalyst Composition 194 Preparation

Aluminum phthalocyanine tetrasulfonylchloride 190 (2 g) was dissolved in 10 mL acetone. Sonication was employed to promote dissolution of the dye. Potassium carbonate (anhydrous; >4 eq, ~1.3 g) was added to the dye solution. The resulting mixture was stirred at room temperature. Aminopropyltriethoxysilane (Silquest A1100; 2 eq, 0.91 g) and DUOMEEN C (Akzo Nobel Surface Chemistry AB, Stenungsund, Sweden, 2 eq, 0.52 g) were mixed with 5 mL of acetone yielding a clear solution. DUOMEEN C comprises a mixture of cocopropylenediamine (CAS [61791-63-7]), and R—NH—$(CH_2)_3$—$NH_2$, wherein R comprises $C_8$-$C_{18}$ straight chain alkyl hydrocarbons.

The clear mixture was slowly added dropwise to the Photocatalyst Composition 190 solution within 10 minute period to form Intermediate 193. The resulting Intermediate 193, in solution, was allowed to stir vigorously at room temperature for 2 hours. Additional potassium carbonate (~0.6 g) was added to the Intermediate 183 mixture followed by dropwise addition of dimethyl sulfate alkylating agent (0.8 g) in acetone (5 mL) to form Photocatalyst Composition 194. The Photocatalyst Composition 194, in solution, was stirred vigorously at room temperature for at least 2 hours prior to use in a coating formulation.

Coating Formulation

| Batch No. | Dye Stock (mL) | 5% NH$_4$OH (mL) | Water (mL) | Q2-5211 (mL) | CAB (mL) | 5% W281F (mL) | VOC content |
|---|---|---|---|---|---|---|---|
| 1 | 2 | 4 | 3 | 1 | 0 | 1 | ~20% |
| 2 | 2 | 4 | 3 | 0 | 1 | 1 | ~20% |

Preparation of Treated Fabric:.

The method of Example 45 was utilized. The treated fabric was dried at 75° C. (oven set @ 80° C.) for 13-16 min.

Antimicrobial Testing:

The treated fabric of this Example 51 was evaluated using the AATCC 100 test procedure described hereinabove in Example 49. Table 6 summarizes the AATCC test results using *K. pneumoniae* and the fabric treated with Batch No. 1 of the coating formulation comprising Photocatalyst Composition 194, as described immediately hereinabove.

TABLE 6

| Sample | Avg CFU/mL | Log |
|---|---|---|
| Test Fabric (light) | 0 | 1 |
| Test Fabric (dark) | $2.19 \times 10^3$ | 3.34 |
| Control T 0 | $1.03 \times 10^5$ | 5.013 |
| Log Reduction (light) | — | 4.013 |
| Log Reduction (dark) | — | 2.34 |

The light exposure experiment was carried out under illumination of fluorescent and incandescent bulbs giving light intensity ~1,000 Lux for 10 min. As those skilled in the art will appreciate, 1,000 Lux light intensity corresponds to recommended interior light intensities within certain areas of hospital and related healthcare settings as specified by the Illuminating Engineering Society of North America ("IESNA"). IESNA is the professional organization that generates standards/guidelines concerning lighting for architectural designs and consumer goods etc. In particular, IESNA Recommended Practices and ANSI Standards recommend lighting levels for hospital environments (in Lux) of 500 Lux for general lighting and 1000 Lux for examination/treatment, respectively. Applicant's irradiation of the fabric treated with the coating of this Example 51, were that treated fabric comprises Photocatalyst Composition 194 mimics the use of that treated fabric in a hospital treatment/examination facility.

The dark experiment was carried out in an incubator with a temperature set at 37-38° C. The observed log reduction values were calculated relative to CFU count from the control fabric at time zero min exposure. The results of Table 6 demonstrate that the observed log reduction value after 10 minutes of light exposure was a combination between a light activation (log reduction of 1.673) and a dark reaction (log reduction of 2.34).

Applicant's bioburden testing and AATCC testing quantitatively demonstrate that fabrics treated with Applicant's coating comprising one or more of Applicant's Photocatalyst Compositions are self-decontaminating with respect to surface pathogens.

In certain embodiments, Applicant's coating composition comprises one or more embodiments of Photocatalyst Composition III in combination with one or more singlet oxygen scavengers, i.e. compounds that reversibly react with singlet oxygen. Applicant has found that N-substituted-2-pyridones 10 trap singlet oxygen upon irradiation in the presence of Photocatalyst Composition III and ambient oxygen to give 1,4-endoperoxides 15. Applicant has further found that such N-substituted-2-pyridonyl endoperoxides 15 efficiently release singlet oxygen over time.

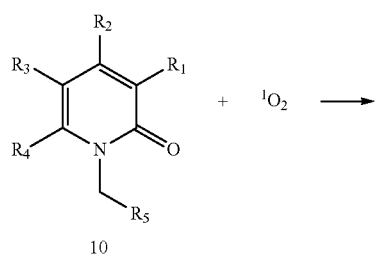 + $^1O_2$ ⟶ 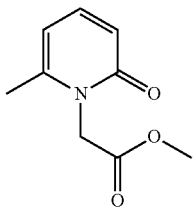
10    15
Applicant has prepared and tested N-substituted-2-pyridones 200A, 200B, 200C, 200D, 200E, 300A, 300B, 300C, 300D, and 400A to determine the efficacy of using these compounds as singlet oxygen scavengers.
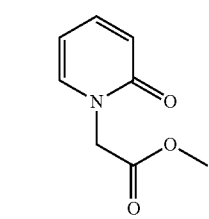
200A
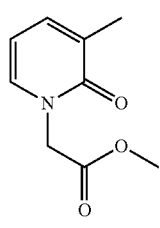
200B
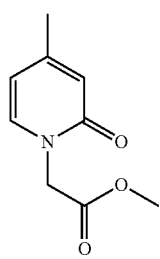
200C
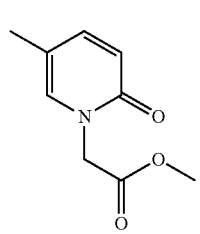
200D
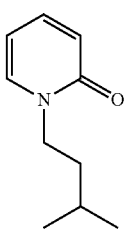
200E
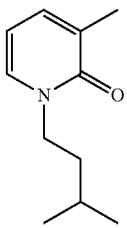
300A
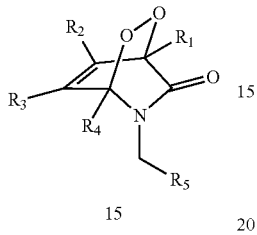
300B
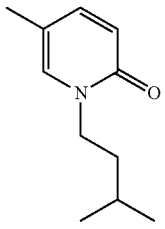
300C
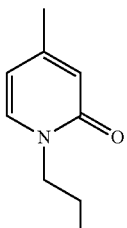
300D
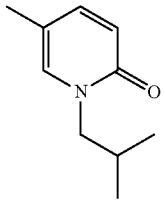
400A Applicant has experimentally determined quantitative data on the singlet oxygen trap-release process of N-methylester substituted pyridones 200A, 200B, 200C, 200D, 200E, and N-isoamyl-2-methylpyridones 300A, 300B, 300C, 300D, and N-isobutyl-2-methylpyridone 400A. All pyridones were purified by column chromatography prior to testing.

Mixtures of each pyridone in combination with tetraphenyl porphyrin ("TPP") were prepared in chloroform. UV-Vis absorption spectrum of each individual solution and the mixture were recorded.

The mixture solution in a quartz cuvette was sealed with a silicone septum screw cap. The solution was irradiated by a Xe arc lamp (150 W) through a FSQ-RG495 filter (yellow; λ>495 nm) and a hot mirror (IR filter). The cuvette sample was located 2 feet away from the lamp housing. A fine stream oxygen (Omega micro flow meter; flow read at 10; 0.342 ml/min) was bubbled to the solution during irradiation. The consumptions of the pyridones were monitored by UV-Vis absorption spectroscopy at their $\lambda_{max}$ 260-340 nm.

The irradiated solution was subsequently allowed to sit in a temperature control cell holder in the dark at 40° C. for 1 min before the absorption spectrum of the solution at 40° C. was recorded. The regeneration of each pyridones was monitored by recording change in its $\lambda_{max}$ as a function of time.

When two individual compounds have overlapped absorption bands, as shown by Equation (1) an absorbance at a particular wavelength in a mixture equals to a summation of absorbances from each individual component at that wavelength.

$$A_m = \epsilon_1 b C_1 + \epsilon_2 b C_2 \tag{1}$$

The thermal decomposition of the endoperoxide adducts were expected to follow a first order reaction kinetics. Thus, the integrated rate law is expressed using equations (2) and (3):

$$1^{st} \text{ order; } [Endo]_t = [Endo]_0 e^{-kt} \tag{2}$$

$$\ln [Endo]_t - kt = +\ln [Endo]_0 \tag{3}$$

The progress of Endoperoxide release reaction was monitored by the increase of the pyridone absorption, thus the concentrations of the endoperoxide at various reaction times can be calculated by equations (4) and (5).

$$[Endo]_t = [Endo]_0 - [Pyridone]_t \tag{4}$$

$$[Pyridone]_t = A_{(pyridone)_t} / \epsilon_{pyridone} \tag{5}$$

TABLE 7 through 16 recite kinetic data for both the formation of an Endoperoxide from a substituted pyridone, and for the deposition of that Endoperoxide to regenerate singlet oxygen. The measured half lives for the 10 endoperoxides studied varied from about 1 hour to about 9.6 hours.

TABLE 7

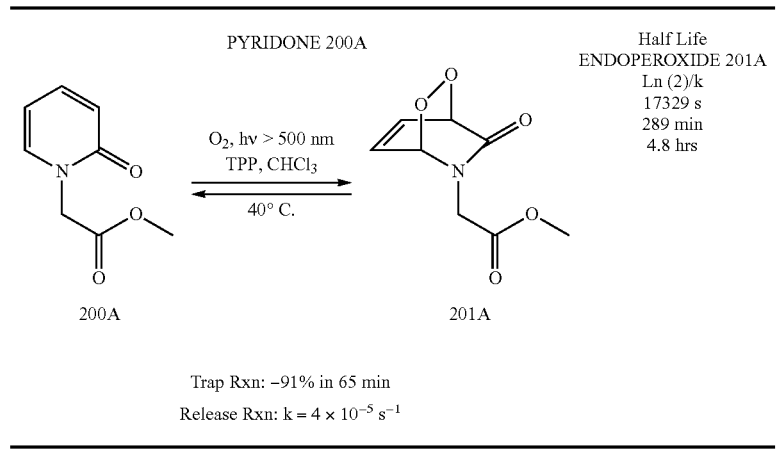

Trap Rxn: −91% in 65 min

Release Rxn: k = 4 × 10⁻⁵ s⁻¹

TABLE 8

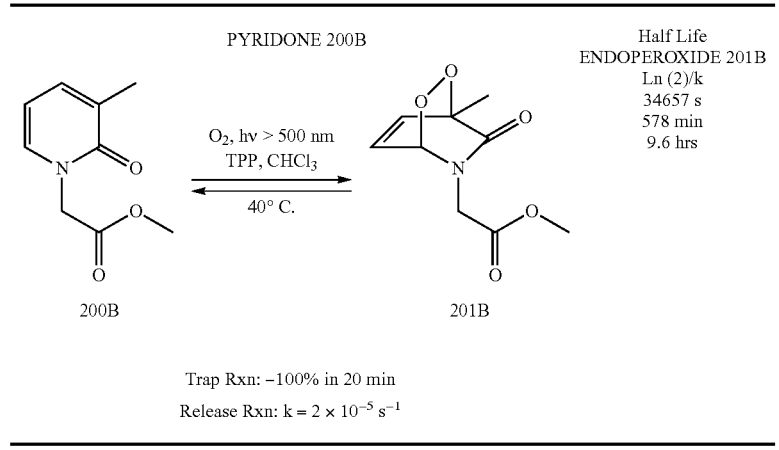

Trap Rxn: −100% in 20 min

Release Rxn: k = 2 × 10⁻⁵ s⁻¹

TABLE 9
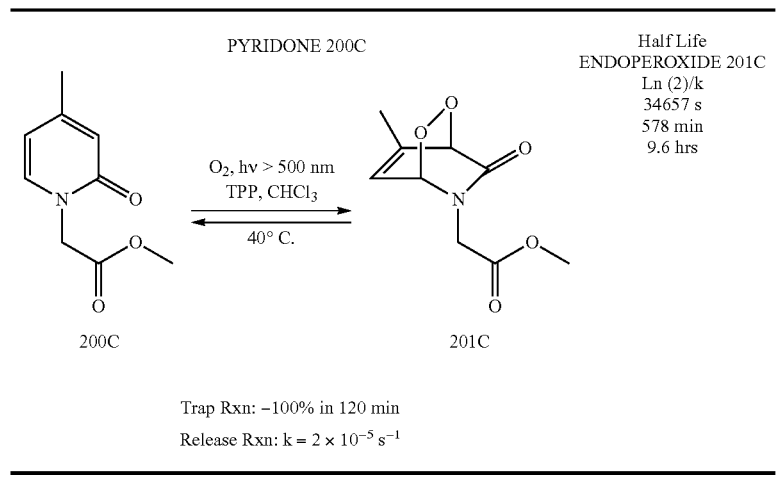
Trap Rxn: ~100% in 120 min
Release Rxn: k = 2 × 10$^{-5}$ s$^{-1}$
PYRIDONE 200C → ENDOPEROXIDE 201C
Half Life
Ln (2)/k
34657 s
578 min
9.6 hrs
TABLE 10
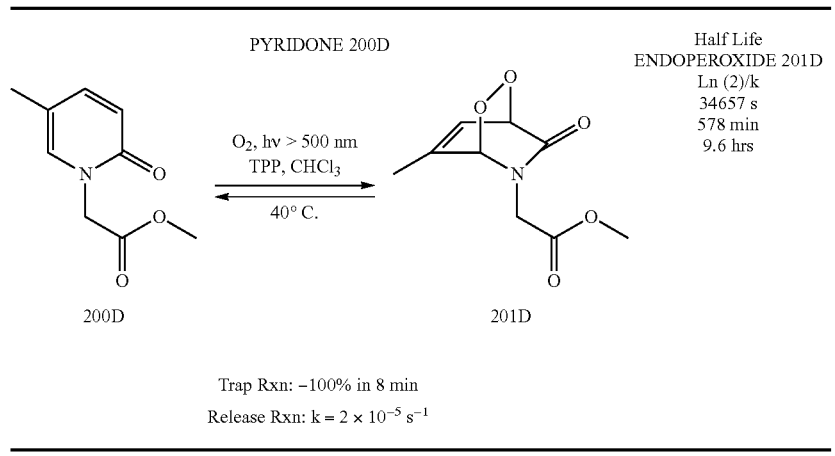
Trap Rxn: ~100% in 8 min
Release Rxn: k = 2 × 10$^{-5}$ s$^{-1}$
PYRIDONE 200D → ENDOPEROXIDE 201D
Half Life
Ln (2)/k
34657 s
578 min
9.6 hrs
TABLE 11
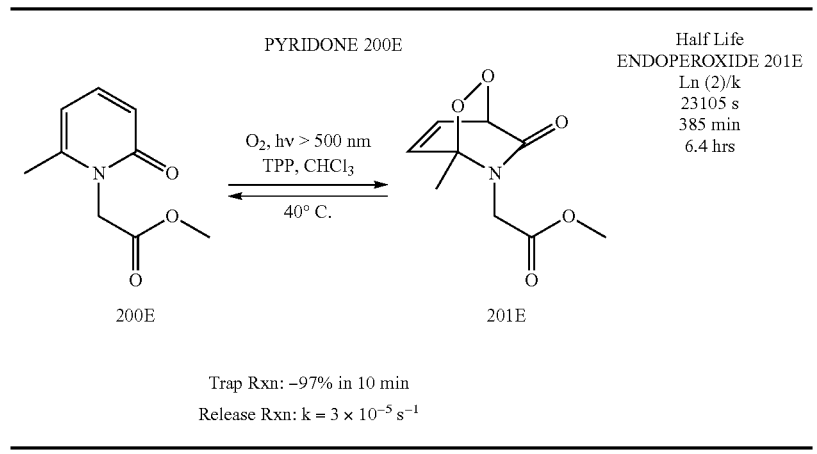
Trap Rxn: ~97% in 10 min
Release Rxn: k = 3 × 10$^{-5}$ s$^{-1}$
PYRIDONE 200E → ENDOPEROXIDE 201E
Half Life
Ln (2)/k
23105 s
385 min
6.4 hrs TABLE 12
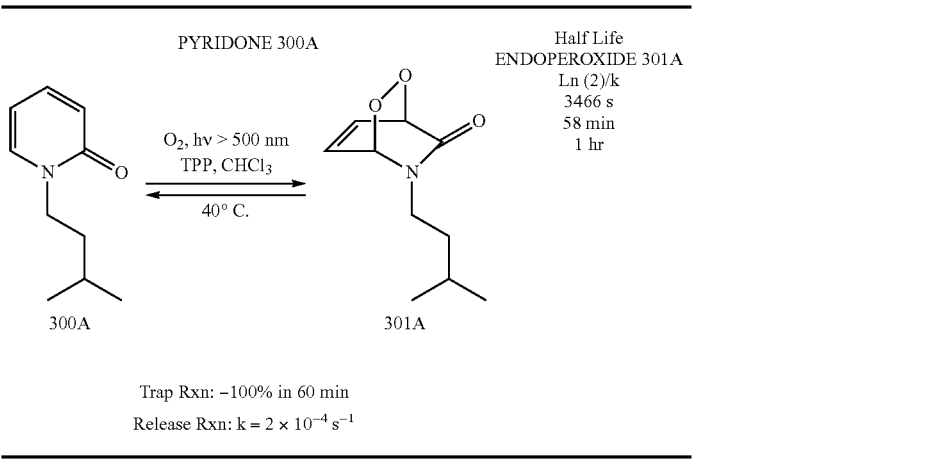
Trap Rxn: ~100% in 60 min
Release Rxn: $k = 2 \times 10^{-4}\ s^{-1}$
TABLE 13
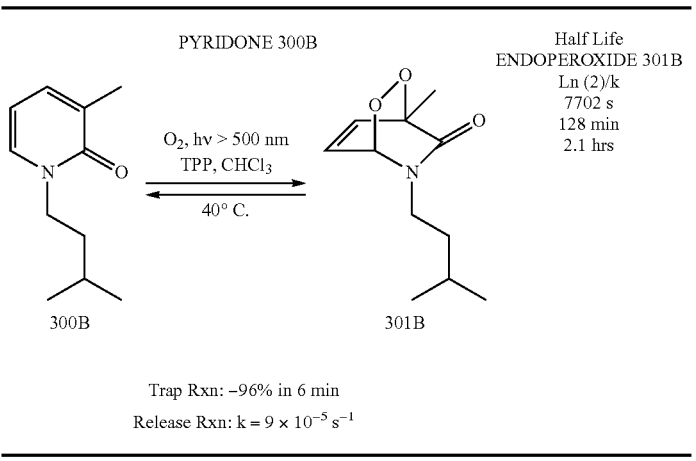
Trap Rxn: ~96% in 6 min
Release Rxn: $k = 9 \times 10^{-5}\ s^{-1}$
TABLE 14
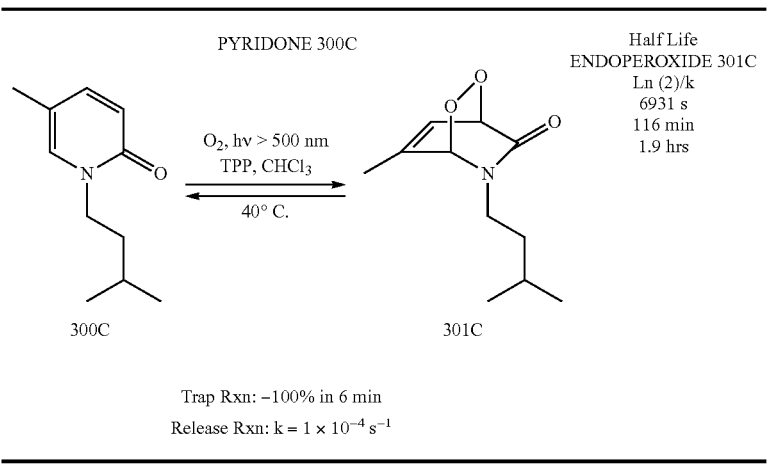
Trap Rxn: ~100% in 6 min
Release Rxn: $k = 1 \times 10^{-4}\ s^{-1}$

TABLE 15

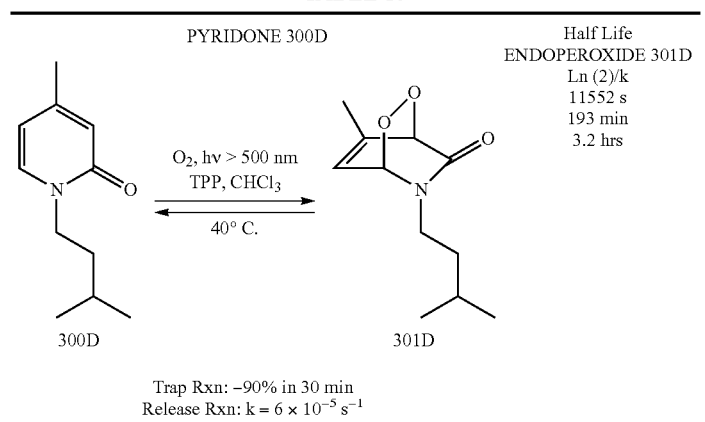

| PYRIDONE 300D | | ENDOPEROXIDE 301D | Half Life Ln (2)/k 11552 s 193 min 3.2 hrs |

Trap Rxn: ~90% in 30 min
Release Rxn: k = 6 × 10$^{-5}$ s$^{-1}$

TABLE 16

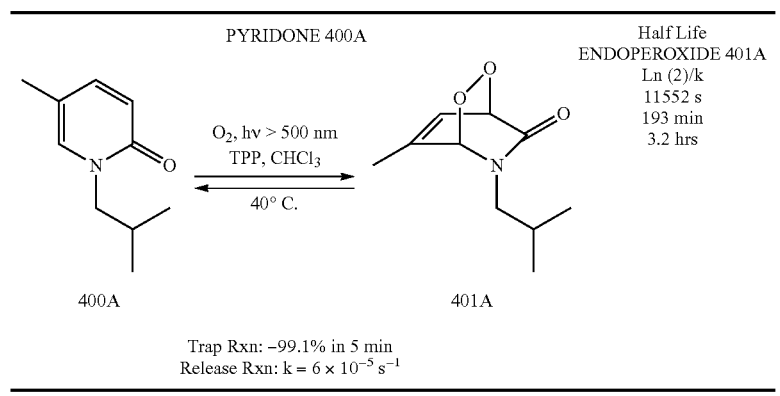

| PYRIDONE 400A | | ENDOPEROXIDE 401A | Half Life Ln (2)/k 11552 s 193 min 3.2 hrs |

Trap Rxn: ~99.1% in 5 min
Release Rxn: k = 6 × 10$^{-5}$ s$^{-1}$

Substitution of a sterically hindering group at the N-atom of the pyridones exhibited an increase in decomposition rate of the endoperoxides. Substitution of an iso-amyl group at the N-atom of the pyridones increases the releasing kinetics by approximately 5 times faster than substitution with a methyl ester group. The best performing pyridone in both singlet oxygen trap and release is 5-methyl-N-isoamyl-2-pyridone.

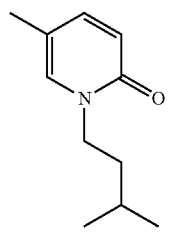

Applicant has modified their substituted pyridone compounds to comprise pendent silyl ester groups. As an example, reacting substituted pyridone 300C with N-Bromosuccinimide in chloroform gives bromonated, substituted pyridone 305C. Reaction of bromonated, substituted pyridone 305C with mercapto silyl ester 7 gives substituted N-isoamyl pyridone 310C, wherein pyridone 310C comprises a pendent silyl ester group.

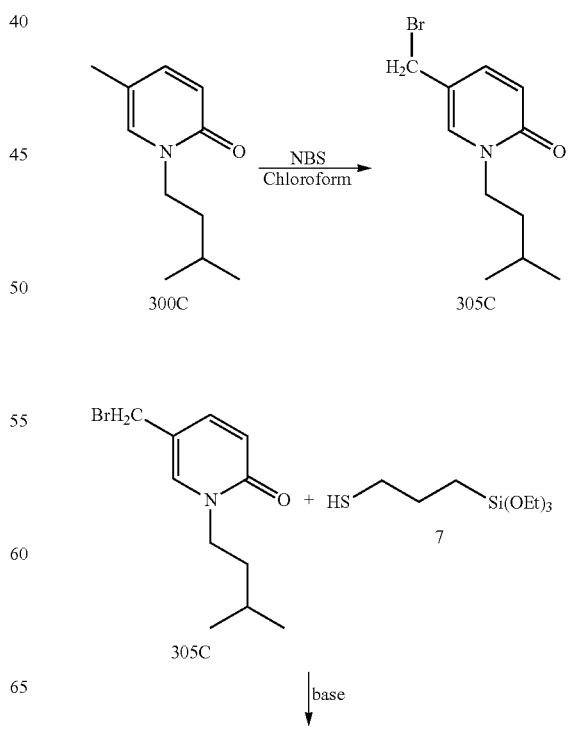

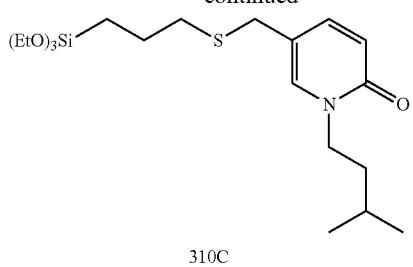

310C

Similarly, substituted pyridones 200B, 200C, 200D, 200E, 300B, 300D, and 400A, can be modified to form substituted pyridones 210B, 210C, 210D, 210E, 310B, 310D, and 410A, each comprising a pendent silyl ester group.

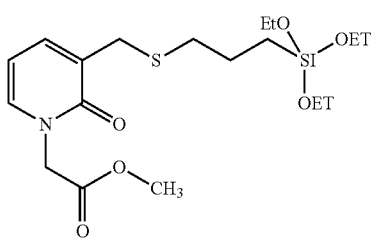

210B

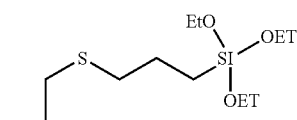

210C

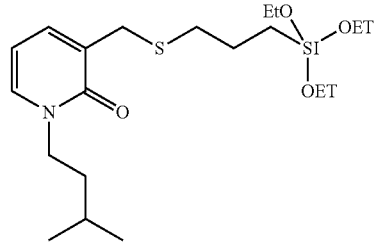

310B

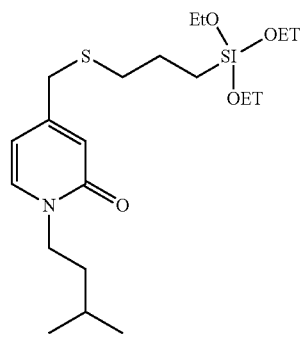

310D

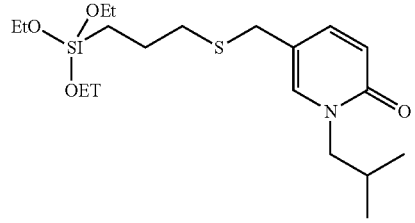

410A

Applicant reacted substituted pyridone 200A with amino silyl ester 4 to form pyridone 210A comprising a pendent silyl ester group.

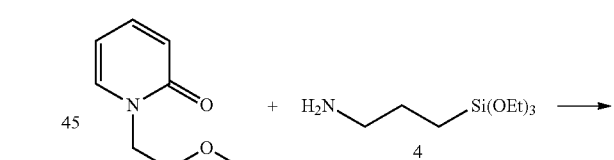

200A

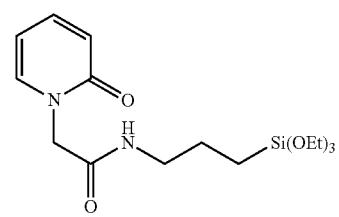

210A

Similar chemistry can be used to form pendent silyl ester containing pyridones 215B, 215C, 215D, and 215E.

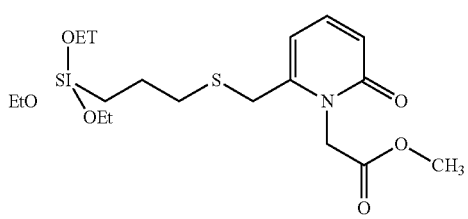

210D

210E

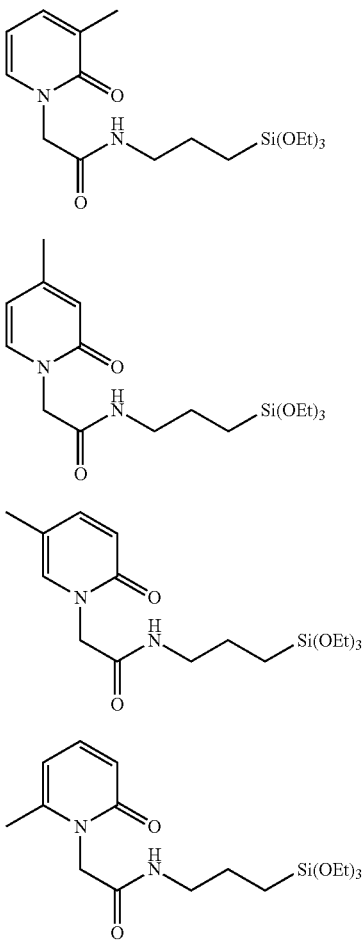

In certain embodiments, Applicant's coating composition comprises one or more of silyl ester substituted pyridones 210A, 210B, 215B, 210C, 215C, 210D, 215D, 210E, 215E, 310B, 310D, and/or 410A, in combination with Applicant's ethanolic/triethylamine/Photocatalyst Composition III mixture. In certain embodiments, the one or more N-methylester substituted pyridones silyl ester substituted pyridones 210A, 210B, 215B, 210C, 215C, 210D, 215D, 210E, 215E, 310B, 310D, and/or 410A, are present from about 0.10 to about 50 molar excess based upon the moles of Photocatalyst III present in the coating composition.

The resulting coating generates singlet oxygen when exposed to both ambient air and light. Applicant has found that both sunlight and artificial light, i.e. both incandescent and/or fluorescent, effectively cause a coating comprising one or more embodiments of Applicant's Photocatalyst Composition III to generate singlet oxygen. When a fabric/substrate bearing a coating comprising one or more embodiments of Applicant's Photocatalyst Compositions in combination with one or more endoperoxides formed from silyl ester substituted pyridones 210B, 210C, 210D, 210E, 310B, 310D, and/or 410A, is disposed in a dark environment such that the one or more Photocatalyst Composition III moieties do not generate singlet oxygen, the one or more endoperoxides decompose to release singlet oxygen, wherein those one or more endoperoxides have the half lives recited in Tables 2 through 11.

The substituted pyridone singlet oxygen traps used in any coating formulation are selected based upon the anticipated hours of darkness that a fabric/substrate coated with Applicant's Photocatalyst Composition/Pyridone coating will experience. For example, where a 1-2 hour period of darkness is anticipated, then the fabric/substrate will be coated with a coating comprising one or more embodiments of Applicant's Photocatalyst Composition in combination with one or more of substituted pyridone 310C. Where a 2-4 hour period of darkness is anticipated, then the fabric/substrate will be coated with a coating comprising one or more embodiments of Applicant's Photocatalyst Composition III in combination with one or more of substituted pyridones 310B, 310D, and/or 410A. Where a 4-6 hour period of darkness is anticipated, then the fabric/substrate will be coated with a coating comprising one or more embodiments of Applicant's Photocatalyst Composition in combination with one or more of substituted pyridones 210E, 310D, and/or 410A. Where a 6-10 hour period of darkness is anticipated, then the fabric/substrate will be coated with a coating comprising one or more embodiments of Applicant's Photocatalyst Composition in combination with one or more of substituted pyridones 210B, 210C, 210D, and/or 210E. Where a period of darkness greater than 10 hours is anticipated, then the fabric/substrate will be coated with a coating comprising one or more embodiments of Applicant's Photocatalyst Composition in combination with one or more of substituted pyridones 210B, 210C, and/or 210D.

In certain embodiments, Applicant's coating comprises one or more photocatalysts in combination with one or more singlet oxygen trap molecules/moieties, as described above. In these embodiments, Applicant's one or more photocatalysts produce singlet oxygen during daylight hours, wherein a portion of that singlet oxygen remains available to oxidize pathogens, and wherein a portion of the singlet oxygen produced is scavenged, i.e. stored, by the one or more singlet oxygen traps which then release that stored singlet oxygen throughout the nighttime hours giving Applicant's coating a time-release decontamination capability.

Applicant's fabric comprises Applicant's coating composition described hereinabove disposed over one or more surfaces thereof. By "fabric," Applicant means a flexible, planar material formed by weaving or felting or knitting or crocheting natural and/or synthetic fibers. In certain embodiments, fabric 1000 comprises polypropylene. In certain embodiments, fabric 1000 comprises polyvinylchloride. In certain embodiments, fabric 1000 comprises cotton. In certain embodiments, fabric 10010 comprises canvas. In certain embodiments, fabric 1000 comprises leather. In certain embodiments, fabric 1000 comprises wool. In certain embodiments, fabric 1000 comprises bamboo. In certain embodiments, fabric 1000 comprises silk. In certain embodiments, fabric 1000 comprises nylon. In certain embodiments, fabric 1000 comprises polyurethane. In certain embodiments, fabric 1000 comprises polyvinylalcohol.

In the illustrated embodiment of FIG. 1A, Applicant's fabric 1000 comprises a surface 1010. FIG. 1A shows surface 1010 comprising a hydroxyl group (—OH) and an amino group (—NH$_2$).

In certain embodiments, surface 1010 is treated with one or more of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189. Referring now to FIG. 1C, a pendant silyl ester group disposed on any one of the above-recited Photocatalyst Compositions can react with a surface hydroxyl group to chemically bond the Photocatalyst to the fabric surface via a silyl ester group. Still referring to FIG. 1C, a pendant silyl ester group disposed on any one of the above-recited Photocatalyst Compositions can react with a surface amino group to chemically bond the Photocatalyst to the fabric surface via a silyl amide group.

Figure 3:
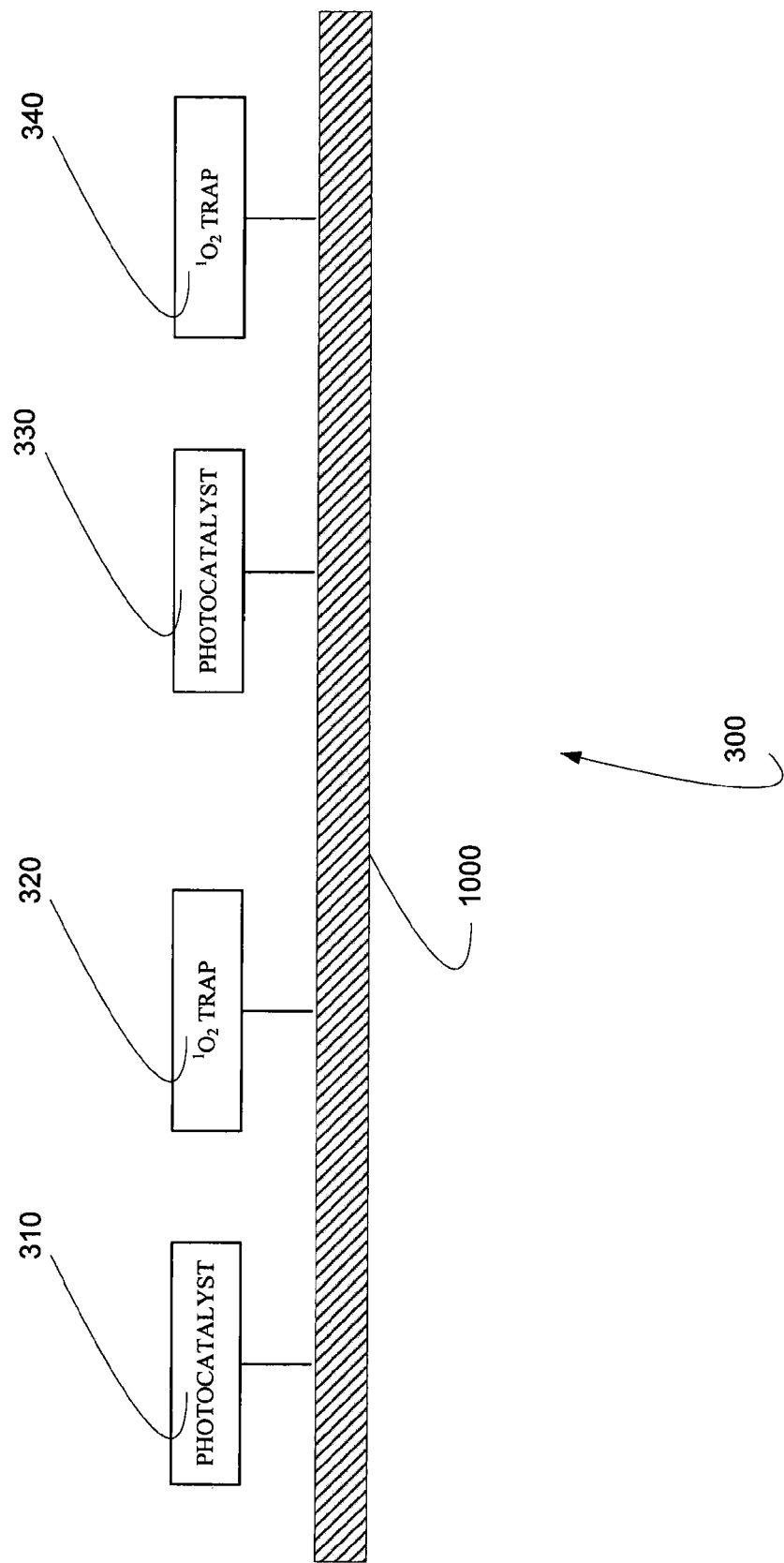
FIG. 3 illustrates a plurality of photocatalyst moieties, and optionally a plurality of singlet oxygen trap moieties, chemically bonded to a fabric.

In certain embodiments, surface 1010 is treated with one or more of N-substituted-2-pyridones 200A, 200B, 200C, 200D, 200E, 300A, 300B, 300C, 300D, and 400A to give fabric 300 shown in FIG. 3. A pendant silyl ester group disposed on any one of the above-recited N-substituted-2-pyridones can react with a surface hydroxyl group to chemically bond the N-substituted-2-pyridones to the fabric surface via a silyl ester group. A pendant silyl ester group disposed on any one of the above-recited N-substituted-2-pyridones can react with a surface amino group to chemically bond the N-substituted-2-pyridones to the fabric surface via a silyl amide group.

Figure 1B:
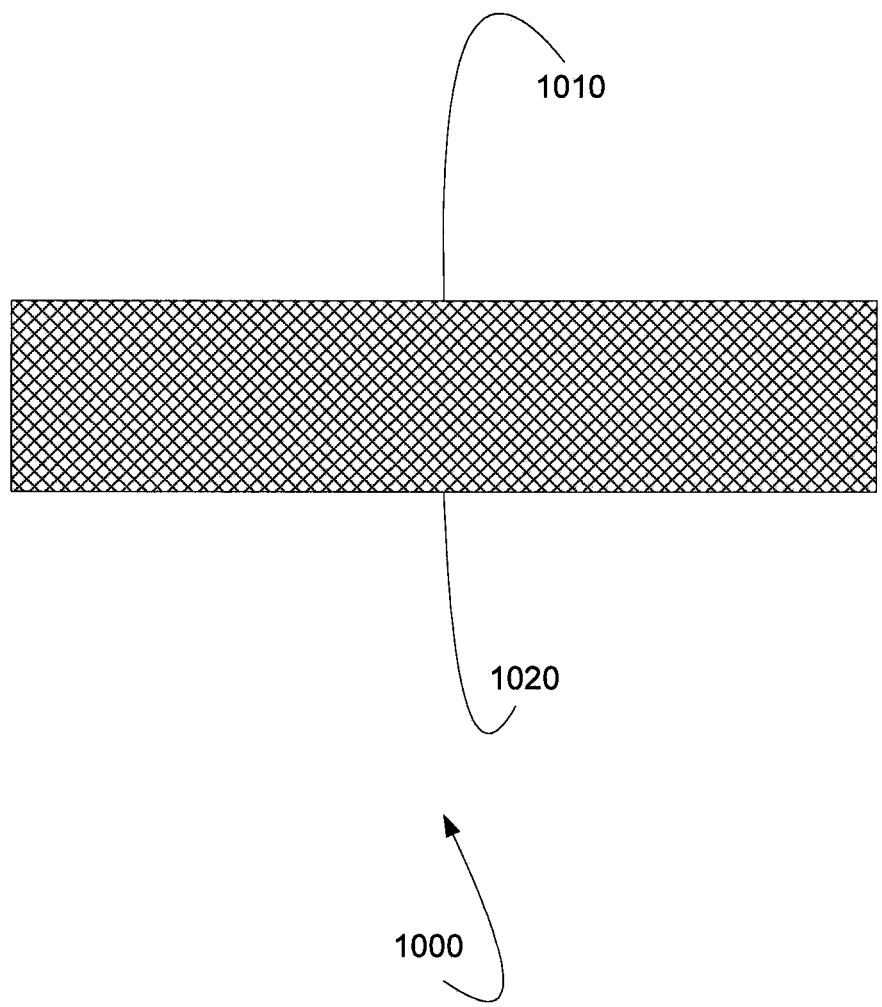
FIG. 1B is a cross-sectional view showing two opposing surfaces of a fabric.
Figure 1C:
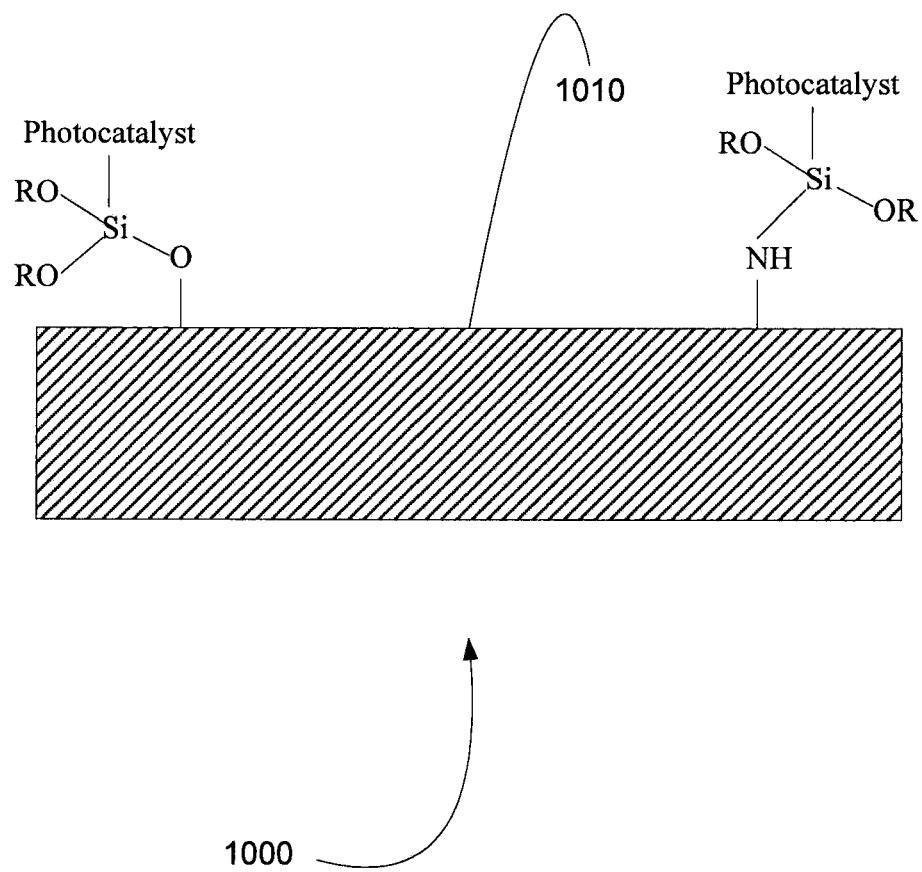
FIG. 1C shows a photocatalyst attached to the surface of the fabric of FIG. 1A via a silyl ester linkage and a photocatalyst attached to the surface of the fabric of FIG. 1A via a silyl amide linkage.

In the illustrated embodiment of FIG. 1B, Applicant's fabric 1000 comprises opposing surfaces 1010 and 1020. In certain embodiments, surfaces 1010 and 1020 are each independently treated with one or more of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189.

Figure 2:
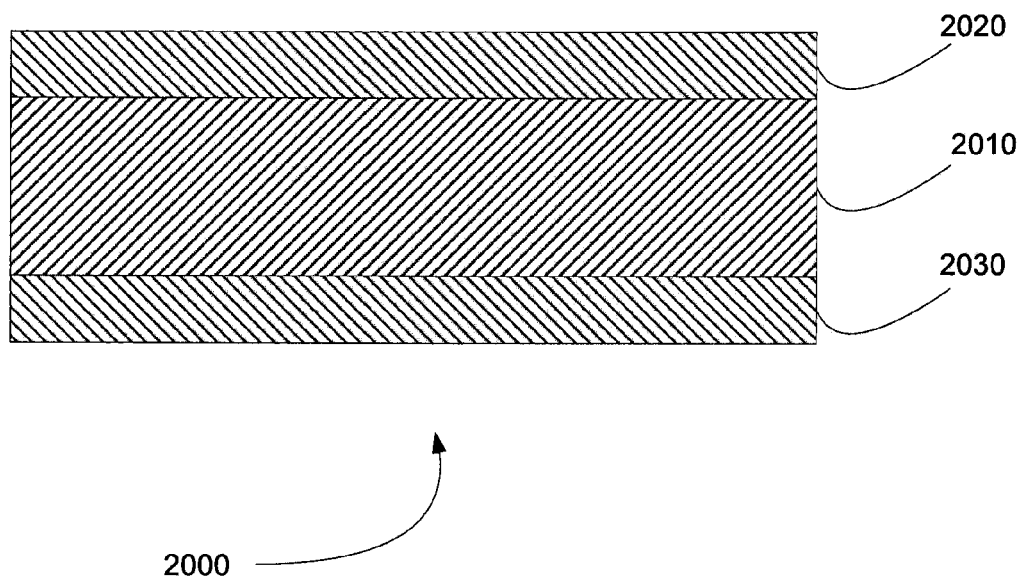
FIG. 2 is a block diagram showing a fabric laminate.

In certain embodiments, Applicant's fabric comprises a multi-layer laminate. In the illustrated embodiment of FIG. 2, fabric laminate 2000 comprises a first fabric 2010 a second fabric 2020, and third fabric 2030. One or more outer surfaces of a fabric laminate, such as fabric laminate 2000 can be treated with Applicant's coating composition, wherein that coating composition comprises one or more Photocatalyst Compositions described herein, and optionally one or more oxygen trap compounds described herein.

Referring now to FIG. 3, in certain embodiments Applicant's fabric 300 comprises a plurality of Photocatalyst Compositions, and optionally a plurality of singlet oxygen traps, chemically bonded to a surface thereof. In accord with FIG. 1B, in other embodiments a plurality of Photocatalyst Compositions, and optionally a plurality of singlet oxygen traps, are chemically bonded to more than one surface of fabric 1000.

In the illustrated embodiment of FIG. 3, fabric 300 comprises Photocatalyst Composition 310 and Photocatalyst Composition 330 chemically bonded thereto, in optional combination with singlet oxygen trap 320 and singlet oxygen trap 340 chemically bonded thereto. In certain embodiments, singlet oxygen trap 320 comprises a first structure and singlet oxygen trap 340 comprises a second structure, wherein the first structure differs from the second structure. In certain embodiments, Photocatalyst Composition 310 comprises a first structure and Photocatalyst Composition 330 comprises a second structure, wherein the first structure differs from the second structure.

In certain embodiments, Photocatalyst Composition 310 comprises one or more of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189. In certain embodiments, Photocatalyst Composition 330 comprises one or more of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189.

In certain embodiments, singlet oxygen trap 320 comprises one or more of N-substituted-2-pyridones 200A, 200B, 200C, 200D, 200E, 300A, 300B, 300C, 300D, and 400A. In certain embodiments, singlet oxygen trap 340 comprises one or more of N-substituted-2-pyridones 200A, 200B, 200C, 200D, 200E, 300A, 300B, 300C, 300D, and 400A.

Figure 4:
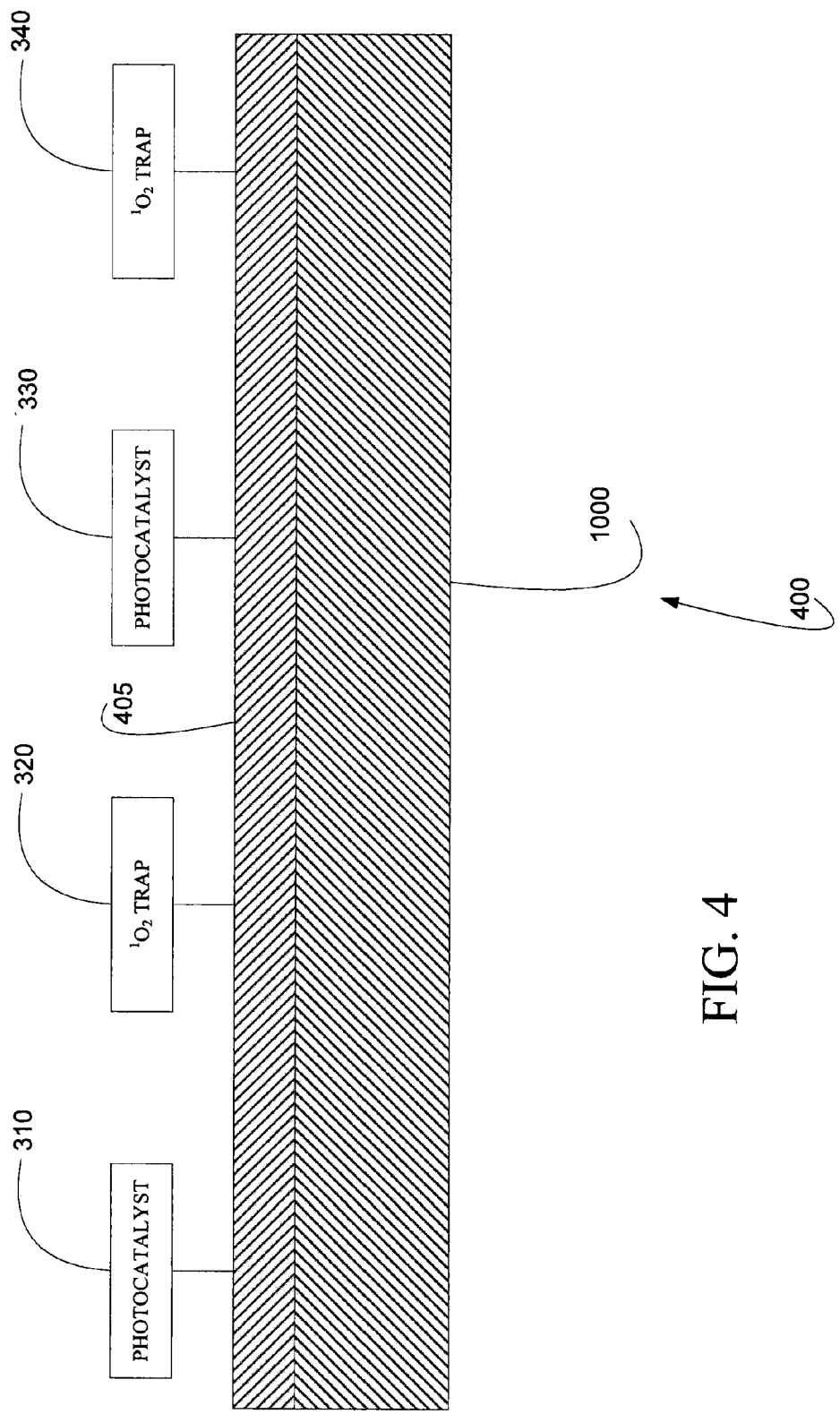
FIG. 4 illustrates a plurality of photocatalyst moieties, and optionally a plurality of singlet oxygen trap moieties, chemically bonded a pre-coating disposed on a fabric.

FIG. 4 illustrates fabric 400 wherein coating 405 is disposed on a first surface of fabric 1000. In certain embodiments, coating 405 comprises a polyurethane pre-coating as described in Example 43 hereinabove. In certain embodiments, Applicant's pre-coating 405 is treated with Applicant's coating composition which comprises a first plurality Photocatalyst Compositions 320 and a second plurality of Photocatalyst Compositions 340. In certain embodiments, Applicant's pre-coating 405 is treated with Applicant's coating composition which optionally comprises a first plurality of singlet oxygen traps 310 and a second plurality of singlet oxygen traps 330.

A pendant silyl ester group disposed on any one of the above-described Photocatalyst Compositions can react with a surface hydroxyl group to chemically bond the Photocatalyst to a surface of coating 405 via a silyl ester group. A pendant silyl ester group disposed on any one of the above-recited Photocatalyst Compositions can react with a surface amino group to chemically bond the Photocatalyst to a surface of coating 405 via a silyl amide group.

A pendant silyl ester group disposed on any one of the above-recited N-substituted-2-pyridones can react with a surface hydroxyl group to chemically bond the N-substituted-2-pyridones to a surface of coating 405 via a silyl ester group. A pendant silyl ester group disposed on any one of the above-recited N-substituted-2-pyridones can react with a surface amino group to chemically bond the N-substituted-2-pyridones to a surface of coating 405 via a silyl amide group.

Figure 5:
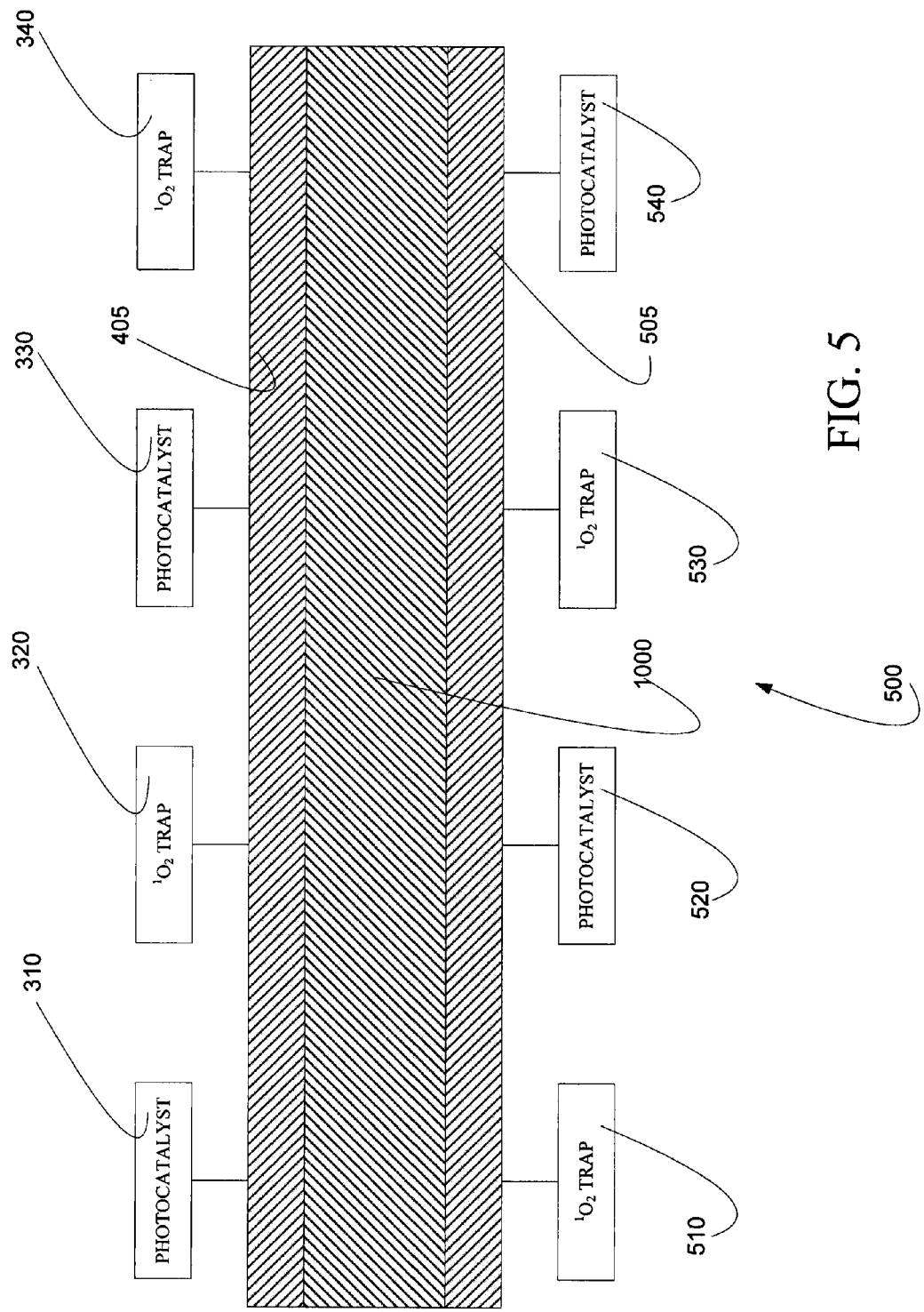
FIG. 5 illustrates a plurality of photocatalyst moieties, and optionally a plurality of singlet oxygen trap moieties, chemically bonded a first pre-coating disposed on a first surface of a fabric, and a plurality of photocatalyst moieties, and optionally a plurality of singlet oxygen trap moieties, chemically bonded a second pre-coating disposed on a second surface of the fabric.

FIG. 5 illustrates fabric 500 wherein coating 405 is disposed on a first surface of fabric 1000, and coating 505 disposed on a second surface of fabric 1000. In certain embodiments, coating 505 comprises a polyurethane pre-coating as described in Example 43 hereinabove. In certain embodiments, Applicant's pre-coating 505 is treated with Applicant's coating composition which comprises a first plurality Photocatalyst Compositions 520 and a second plurality of Photocatalyst Compositions 540. In certain embodiments, Applicant's pre-coating 505 is treated with Applicant's coating composition which optionally comprises a first plurality of singlet oxygen traps 510 and a second plurality of singlet oxygen traps 530.

In certain embodiments, singlet oxygen trap 510 comprises one or more of N-substituted-2-pyridones 200A, 200B, 200C, 200D, 200E, 300A, 300B, 300C, 300D, and 400A. In certain embodiments, singlet oxygen trap 530 comprises one or more of N-substituted-2-pyridones 200A, 200B, 200C, 200D, 200E, 300A, 300B, 300C, 300D, and 400A.

In certain embodiments, Photocatalyst Composition 520 comprises one or more of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189. In certain embodiments, Photocatalyst Composition 540 comprises one or more of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189.

A pendant silyl ester group disposed on any one of the above-described Photocatalyst Compositions can react with a surface hydroxyl group to chemically bond the Photocatalyst to a surface of coating 405 via a silyl ester group. A pendant silyl ester group disposed on any one of the above-recited Photocatalyst Compositions can react with a surface amino group to chemically bond the Photocatalyst to a surface of coating 405 via a silyl amide group.

A pendant silyl ester group disposed on any one of the above-recited N-substituted-2-pyridones can react with a surface hydroxyl group to chemically bond the N-substituted-2-pyridones to a surface of coating 405 via a silyl ester group. A pendant silyl ester group disposed on any one of the above-recited N-substituted-2-pyridones can react with a surface amino group to chemically bond the N-substituted-2-pyridones to a surface of coating 405 via a silyl amide group.

While the preferred embodiments of the present invention have been illustrated in detail, it should be apparent that modifications and adaptations to those embodiments may occur to one skilled in the art without departing from the scope of the present invention as set forth in the following claims.

We claim:

1. A fabric comprising:
a first photocatalyst to produce singlet oxygen from ambient oxygen chemically attached to a surface of said fabric via a silyl ester bond;
a second photocatalyst to produce singlet oxygen from ambient oxygen chemically attached to said surface of said fabric via a silyl amide group.

2. The fabric of claim 1, wherein said fabric is self-decontaminating with respect to odor.

3. The fabric of claim 2, wherein said fabric is self-decontaminating with respect to cigarette smoke odor.

4. The fabric of claim 1, further comprising a compound to reversibly react with singlet oxygen to form an endoperoxide.

5. The fabric of claim 4, wherein said compound is chemically attached to said first photocatalyst.

6. The fabric of claim 4, wherein two or more of said compound are attached to said first photocatalyst.

7. The fabric of claim 4, wherein said compound is chemically bound to said surface via a silyl ester bond.

8. The fabric of claim 1, wherein said fabric is self-decontaminating with respect to pathogens.

9. The fabric of claim 8, further comprising treated fabric bacteria levels for each of aerobic, anaerobic, and spore forming bacteria, wherein:
a fabric that does not comprise said first photocatalyst and said second photocatalyst comprises untreated fabric bacterial levels for each of aerobic, anaerobic, and spore forming bacteria;
said treated fabric bacteria level for each of said aerobic, anaerobic, and spore forming bacteria, is less than said untreated fabric bacteria levels for each of said aerobic, anaerobic, and spore forming bacteria, respectively.

10. An indoor accessory comprising:
a fabric, wherein said fabric comprises a surface;
a first photocatalyst to produce singlet oxygen from ambient oxygen chemically attached to said surface via a silyl ester bond;
a second photocatalyst to produce singlet oxygen from ambient oxygen chemically attached to said surface via a silyl amide group.

11. The indoor accessory of claim 10, wherein said indoor accessory is selected from the group consisting of furniture, cushions, pillows, bedding, curtains, and floor coverings.

12. The indoor accessory of claim 11, wherein said fabric is self-decontaminating with respect to odor.

13. The indoor accessory of claim 12, wherein said fabric is self-decontaminating with respect to cigarette smoke odor.

14. The indoor accessory of claim 10, wherein the fabric further comprises a compound to reversibly react with singlet oxygen to form an endoperoxide.

15. The indoor accessory of claim 14, wherein said compound is chemically bound to said fabric via a silyl ester bond.

16. The indoor accessory of claim 10, wherein said fabric is self-decontaminating with respect to pathogens.

17. The indoor accessory of claim 16, wherein said fabric further comprises treated fabric bacteria levels for each of aerobic, anaerobic, and spore forming bacteria; wherein:
a fabric that does not comprise said first photocatalyst and said second photocatalyst comprises untreated fabric bacterial levels for each of aerobic, anaerobic, and spore forming bacteria;
said treated fabric bacteria level for each of said aerobic, anaerobic, and spore forming bacteria, is less than said untreated fabric bacteria levels for each of said aerobic, anaerobic, and spore forming bacteria, respectively.

* * * * *